US006306400B1

(12) United States Patent
Bublot et al.

(10) Patent No.: US 6,306,400 B1
(45) Date of Patent: Oct. 23, 2001

(54) AVIAN RECOMBINANT LIVE VACCINE USING, AS VECTOR, THE AVIAN INFECTIOUS LARYNGOTRACHEITIS

(75) Inventors: Michel Bublot, St Genis les Olieres; Eliane Laplace, Oullins; Jean-Christophe Audonnet, Lyons, all of (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/362,831

(22) Filed: Jul. 28, 1999

Related U.S. Application Data

(63) Continuation of application No. PCT/FR98/00122, filed on Jan. 23, 1998.

(30) Foreign Application Priority Data

Jan. 31, 1997 (FR) .................................. 97 01317

(51) Int. Cl.[7] ........................ A61K 39/12; A61K 39/295
(52) U.S. Cl. ........................ 424/199.1; 424/202.1; 424/816; 435/320.1; 435/235.1
(58) Field of Search .................... 424/199.1, 229.1, 424/816, 202.1; 435/235.1, 320.1

(56) References Cited

U.S. PATENT DOCUMENTS 6,045,803 * 4/2000 Audonnet et al. ............. 424/199.1

FOREIGN PATENT DOCUMENTS 0 719 864 A2  7/1996 (EP) .
WO 92/03554  3/1992 (WO) .
WO 96/00791  1/1996 (WO) .

OTHER PUBLICATIONS

Johnson et al (Arch. Virol. 140:623–634), 1995.*
Ren et al (Virology 204:242–250), 1994.*

* cited by examiner

Primary Examiner—Mary E. Mosher
(74) Attorney, Agent, or Firm—Frommer Lawrence & Haug, LLP; William S. Frommer; Thomas J. Kowalski

(57) ABSTRACT

The avian recombinant live vaccine comprises, as vector, an ILTV virus comprising and expressing at least one heterologous nucleotide sequence, this nucleotide sequence being inserted into the insertion locus formed by the intergenic region situated between the stop codons of the ORF D and ORF E of ILTV and which, in a specific ILTV strain, is defined between nucleotides 3873 and 4260 in SEQ ID No:1. The heterologous nucleotide sequence may be under the control of a strong eukaryotic promoter, such as the CMV-IE promoter, and may be derived from the Newcastle disease virus, Marek's disease virus, the infectious bursal disease virus, the infectious bronchitis virus, the chicken anaemia virus and the chicken pneumovirosis virus. Multivalent vaccine formula comprising at least two live vaccines according to the invention. ILTV vir Sequenced part (7082 bp)

```
                    EcoRI
      1   GAATTCTAAGCTTGCTTTGTCAACCAGTTTTGTTTTCTTTTTGGGGGGAGGGTAGCACA
     61   CTCTGCCCGAGTCTCGGCATTGACTTAACAGTGATGTGAAACCCGGAAGATCGAGCATGA
    121   ACTAATAGCATTAAAGAATTGTTATCCGAGGAATAATCGTGGACGCGAATTTACTCGACC
    181   GCTAAAATCTTTCTTCTACTGAGCTGGATACGTGAAATTTGGTGAGTATAACCTCTCGGG
                                                                ORF A
    241   ATACATAGCTTTTAAATACGGGGCGTGCAATATTAAATTCTGCACTCGGGGCTGCAATGG
                                                               1▶ MetG
    301   AGCGCGGAGCTTTATTTGACAAGACCGCCAATTGCAAGGACTGGGTCTCGATCGGGACTA
      2▶ luArgGlyAlaLeuPheAspLysThrAlaAsnCysLysAspTrpValSerIleGlyThrT
                         ClaI
    361   CTGTGTGGGGCGCGATCGATGCAGATGACGGGGACGACTTAGTCTGGGATTATGAAAATA
     22▶ hrValTrpGlyAlaIleAspAlaAspAspGlyAspAspLeuValTrpAspTyrGluAsnS
                         SmaI
    421   GCCCATATCCAAGCATAGTTTCCTCACTATTCCCGGGGGAAGAAACGGACTCGGCAATTT
     42▶ erProTyrProSerIleValSerSerLeuPheProGlyGluGluThrAspSerAlaIleC
    481   GTAACTCTGTTGTTGCCGCAAACCCCTGTAGCATACCTCCTGGGCGGCAGCGTTTGGCAT
     62▶ ysAsnSerValValAlaAlaAsnProCysSerIleProProGlyArgGlnArgLeuAlaT
    541   GGCCATGCTGCTGTTTTCGTCGGCCAGACAGCTTCTCCGTCCCGCGCGTGGAAGTTAATG
     82▶ rpProCysCysCysPheArgArgProAspSerPheSerValProArgValGluValAsnA
    601   CTCGCCTTGTTGCCGCGGTTGCACTGATAATTTTCTCATTGCTTGTAGTGATCTGTGTTG
    102▶ laArgLeuValAlaAlaValAlaLeuIleIlePheSerLeuLeuValValIleCysValA
                      ORF B
    661   CGTCATATTGGGGGTAACATGTCTTCAGAGGACACATCGGGATTCCTAACGCCCCCCGCA
    122▶ laSerTyrTrpGly··1▶ MetSerSerGluAspThrSerGlyPheLeuThrProProAla
                                                       BamHI
    721   AGTGATGACGACACTGACCCTTCCGAGCCACCACCAAATTTATGGATCCTCACCAGGAC
     15▶ SerAspAspAspThrAspProSerGluProProProAsnLeuTrpAspProHisGlnAsp
    781   GATTTTCCGAGGGACGCTGATTCCCCAAACCCACTTTTCTACCCCTGGGATGACTCTGTG
     35▶ AspPheProArgAspAlaAspSerProAsnProLeuPheTyrProTrpAspAspSerVal
    841   AATAATACTGGGGATACGGGCAGTAACGAAGATGACTATGTAGATATGGGAGGGGTAGGT
     55▶ AsnAsnThrGlyAspThrGlySerAsnGluAspAspTyrValAspMetGlyGlyValGly
               BamHI
    901   GGATCCGAAGACTATGAAGACCTCGGTACGGGCGGGGACTCTGACTATGACAATGTATCT
     75▶ GlySerGluAspTyrGluAspLeuGlyThrGlyGlyAspSerAspTyrAspAsnValSer
    961   ACAGCGACCGGCGGGACGTGGTTTCCTTCCCTTACTTCTTGGTCATCAGAGGACCACGGC
     95▶ ThrAlaThrGlyGlyThrTrpPheProSerLeuThrSerTrpSerSerGluAspHisGly
   1021   CCAACTTCTCCGGAAAACCCTATGCAACAACTTCAAGTAACAATTCAGCAGGATTCAGAT
    115▶ ProThrSerProGluAsnProMetGlnGlnLeuGlnValThrIleGlnGlnAspSerAsp
   1081   CCACAGCAGGAACCCGATCCCCAGCAAGTTCCCGGTCTCCAGCAGGAACCTGACCCCCAG
    135▶ ProGlnGlnGluProAspProGlnGlnValProGlyLeuGlnGlnGluProAspProGln
   1141   CAAGATCCACGAGAGCCTCGTGATCCTCCTCCCTATAGTCCGCCCCCAGAGGACCCTTTT
    155▶ GlnAspProArgGluProArgAspProProProTyrSerProProProGluAspProPhe
   1201   GGGCTCTCGCCATTTACTAGTGGGATGGGCGGGTTTGGGCCACCGTGGCGTGGCCCCAGC
    175▶ GlyLeuSerProPheThrSerGlyMetGlyGlyPheGlyProProTrpArgGlyProSer
```

|  |  | FIG. 2A |
|---|---|---|
|  |  | FIG. 2B |
| FIG. 2A | FIG. 2 | FIG. 2C |
|  |  | FIG. 2D |
|  |  | FIG. 2E |
|  |  | FIG. 2F |

```
1261 CACCCTCGTATGATGAGGCAATGGGGGATGGACCTTTTACTACGACTGGGGGTCGGCGAC
 195▶ HisProArgMetMetArgGlnTrpGlyMetAspLeuLeuLeuArgLeuGlyValGlyAsp
1321 CTTGCTCACGCAGGCGCGGTCGTCGCCGGTCTCGAGGTCGATCTCGGCGACGCAATTGGT
 215▶ LeuAlaHisAlaGlyAlaValValAlaGlyLeuGluValAspLeuGlyAspAlaIleGly
1381 GTGCAGCAAAGTTGTGCTCAGAGGCATGTTTGTGGCATCTCTTTTGGGTTGGAGTGGCCT
 235▶ ValGlnGlnSerCysAlaGlnArgHisValCysGlyIleSerPheGlyLeuGluTrpPro
1441 TAATGTGTTGGTGGCTCTTGTATCTTATTTTGCGCATTGTCTGGGGACAGACTCCGGGAT
 255▶ ...
1501 AAGGAAGGTTGTATCCGCATCCAGTACTCCTCAATAAAAGCGTGGTGGTGCTACACGATG
                                                   XbaI
1561 TCTGTTAATTTTACAACTCCATTTTACAGGTGATCTAGAGAGACGCTGAGTGGCACTTGT
                          ORF C
1621 CCCGACGGGACCATGCAGTCGAACAGCAGCGATGAGGCCCAGTGTGATGATGTCGAGGAG
               1▶ MetGlnSerAsnSerSerAspGluAlaGlnCysAspAspValGluGlu
1681 GGATGGTCGTCCATAGCTCCAGGTGATGCACTGGATACAGATTTCATTCCAGGGCCTTGT
 17▶ GlyTrpSerSerIleAlaProGlyAspAlaLeuAspThrAspPheIleProGlyProCys
1741 GCCACGTCCATACATGGTATATCCAAGGCAGTTTATTTTTTCTGTGTGGAGTTAATCTG

37▶ AlaThrSerIleHisGlyIleSerLysAlaValTyrPhePheLeuCysGlyValAsnLeu
1801 GAGGAATGTAGTACACTCCCACAGCATGTCCAATCTCACCCATATGGACATCCTGAGCTG

57▶ GluGluCysSerThrLeuProGlnHisValGlnSerHisProTyrGlyHisProGluLeu
1861 AAATCAGGCAAATGGTACAAGAGGTTTTGCTCCGGGCTAGGCGAAATTGGAGATACAAGC

77▶ LysSerGlyLysTrpTyrLysArgPheCysSerGlyLeuGlyGluIleGlyAspThrSer
1921 CAGTGTCAGCTGACACGACTATGCTGCACTTCCGGAATGCCGGCACAGATTTTTGGGCCT

97▶ GlnCysGlnLeuThrArgLeuCysCysThrSerGlyMetProAlaGlnIlePheGlyPro
1981 TCGAGATTCAGGTCTCTGCAACAGAAGCCAACCCATATGCGGGCCCAAGATTTGCTCACT
 117▶ SerArgPheArgSerLeuGlnGlnLysProThrHisMetArgAlaGlnAspLeuLeuThr
2041 AGGCCTTGCCATATACTAGAGTTCGATGTTGGCGCTGACCTAATCAATCTTTTCTTGTAT

137▶ ArgProCysHisIleLeuGluPheAspValGlyAlaAspLeuIleAsnLeuPheLeuTyr
                                               ClaI
2101 ATGGAACCATGTTCAGGGAATCGATATTGCGTACATTTAGGATACCATAAAACTAATGCC
 157▶ MetGluProCysSerGlyAsnArgTyrCysValHisLeuGlyTyrHisLysThrAsnAla
2161 ATGCGTGTTTTGAGCGGTGGTGGGATTCTATGGGGCAGACTTCCGTGGAAGGACAACACC
 177▶ MetArgValLeuSerGlyGlyGlyIleLeuTrpGlyArgLeuProTrpLysAspAsnThr
2221 GAGGAGCACGGGTACTCGTTGCCTATGCGAGTATTTGGGATCAAATTGCCCCATAAAGTT
 197▶ GluGluHisGlyTyrSerLeuProMetArgValPheGlyIleLysLeuProHisLysVal
2281 TATGTGGCATGTCGCTGCCCTGCAACTCGGACGGAACTATTATTTGGTGAGGGGGGGGTA
```

FIG. 2B

| | FIG. 2A |
|---|---|
| | FIG. 2B |
| FIG. 2 | FIG. 2C |
| | FIG. 2D |
| | FIG. 2E |
| | FIG. 2F |

```
217▶ TyrValAlaCysArgCysProAlaThrArgThrGluLeuLeuPheGlyGluGlyGlyVal
2341 GGATTCAACGCGGAAAACTTTAAACAGTGCGGACGGTTGAAAAAAGAGTGTGAATGTCTG

237▶ GlyPheAsnAlaGluAsnPheLysGlnCysGlyArgLeuLysLysGluCysGluCysLeu
2401 CAGAAGGCTTGTTTTACTGCACAAACGGTGTTAGGTGCGGCATGTAAGTTTACTGTATAC

257▶ GlnLysAlaCysPheThrAlaGlnThrValLeuGlyAlaAlaCysLysPheThrValTyr
                                                          ORF D
2461 TCGAGCAAGGGACGAGGTCAAGAAATTCTGCTATATCAGGACCCATGAATGCTACAACGG
                                                     1▶ MetAsnAlaThrThrV
277▶ SerSerLysGlyArgGlyGlnGluIleLeuLeuTyrGlnAspPro···
2521 TAATGCCTGTAGTACTGGGTATGTTAAGTAGAGAACCCCACAGGTGTGCAGGTACACTCA
  6▶ alMetProValValLeuGlyMetLeuSerArgGluProHisArgCysAlaGlyThrLeuI
2581 TACTGTCCAGGTCCTCTCTGGAAATTGCCGTGGATTTCATGAGACCCAACACGATATTCCCA
 26▶ leLeuSerArgSerSerGlyAsnCysArgGlyPheHisGluThrGlnHisAspIleProT
               SmaI
2641 CTAACCCGGGTCTGTATCCTCTGTGTAATCATGAGCACCCTTACTATGTGACAGTTACAG
 46▶ hrAsnProGlyLeuTyrProLeuCysAsnHisGluHisProTyrTyrValThrValThrA
2701 ATGTATGCGGCAACTGTTGTTCATGGCTTGAGCGGGTTTTTGGGAGAGTAGCTGCCCCTG
 66▶ spValCysGlyAsnCysCysSerTrpLeuGluArgValPheGlyArgValAlaAlaProA
2761 CTGGTCTAAGCTCCGTATCTGTATCCATTAAAGGCTCCACCCACAGCGGGACTGACGTGA
 86▶ laGlyLeuSerSerValSerValSerIleLysGlySerThrHisSerGlyThrAspValT
2821 CAGAAGAACGTGAAGAGGACTCAGGGACACAGCAAACCTCCCACGACAAATTGCCGGAGC
106▶ hrGluGluArgGluGluAspSerGlyThrGlnGlnThrSerHisAspLysLeuProGluA
                BstBI
2881 GCAACCGCATGGGAGATCAAAATTCGAATTTGCGGGGAAGAGATCAATATTGGCCGCCTG
126▶ rgAsnArgMetGlyAspGlnAsnSerAsnLeuArgGlyArgAspGlnTyrTrpProA
2941 CCCCACACCGTAGTCATTGTCACTCGGATTTTATATTCGATGAACCTGAGCCAGAAAGTG
146▶ laProHisArgSerHisCysHisSerAspPheIlePheAspGluProGluProGluSerG
3001 GGGAAGACGTGCATAACATGCATCCTCCACGAGGTGCAGATGAGCAAACAGCCGCTTCTG
166▶ lyGluAspValHisAsnMetHisProProArgGlyAlaAspGluGlnThrAlaAlaSerV
3061 TGTCAGCGCTAATGCAAAGTCTAGCACAAGCATTGGTGAGTGCACAAGCTATTAGCAGCA
186▶ alSerAlaLeuMetGlnSerLeuAlaGlnAlaLeuValSerAlaGlnAlaIleSerSerM
3121 TGGTCTCTGGCTCTGCTTCCTCAGTGGGCGTAGAAGTAGACTGTGGGTACAGTCAGACTC
206▶ etValSerGlySerAlaSerSerValGlyValGluValAspCysGlyTyrSerGlnThrH
3181 ATATTACAGAGGGGCCGGGGAGGGAACAATTCGGTAGAGTCCCAGAAAGAGGGCCAGAGT
226▶ isIleThrGluGlyProGlyArgGluGlnPheGlyArgValProGluArgGlyProGluT
3241 ATCCTCAAGATTACTGTGATATATATGGTCCTGTAAGTAATGGGCCTGCTGGATACAGAG
246▶ yrProGlnAspTyrCysAspIleTyrGlyProValSerAsnGlyProAlaGlyTyrArgA
3301 CAGGACCACCAGATGCTCCTAGTATACAAGATAGGACCTTCCCATGCGGCAGAAGATGCG
266▶ laGlyProProAspAlaProSerIleGlnAspArgThrPheProCysGlyArgArgCysA
3361 ACGAAGCATGGCTTGCCTTAGAAGTAGGGAATATGCCTTGGATTTCTTCTGGTTCACATA
286▶ spGluAlaTrpLeuAlaLeuGluValGlyAsnMetProTrpIleSerSerGlySerHisS
3421 GTCCACCTTCTCAGTATCATAACCCTTATGGTTCACATAGTCCACCTTCCCAGTCTCATA
306▶ erProProSerGlnTyrHisAsnProTyrGlySerHisSerProProSerGlnSerHisA
3481 ACCCTTATGGTACATATAGTCCGCCTTCTCAGTCTCATAACCCTTATGGCTCATATAGTC
326▶ snProTyrGlyThrTyrSerProProSerGlnSerHisAsnProTyrGlySerTyrSerP
3541 CGCCTTCCCAGTATCATAACCCTTGTGGTACATATAGTCCGCCTTCTCAGTCTCGTAAGC
346▶ roProSerGlnTyrHisAsnProCysGlyThrTyrSerProProSerGlnSerArgLysH
```

| | FIG. 2A |
|---|---|
| | FIG. 2B |
| FIG. 2C FIG. 2 | FIG. 2C |
| | FIG. 2D |
| | FIG. 2E |
| | FIG. 2F |

```
3601 ATGACTATTCACCTCCATATCCGATACTCAAACCAAAGCCTCGATTACCCCCAGGCTTTG
 366▶ isAspTyrSerProProTyrProIleLeuLysProLysProArgLeuProProGlyPheG
3661 AAAATACTGCTGGGATGTGGCCTCGATGTCCCCCTGGGTTTGAGGGGCGTCCATACAAAT
 386▶ luAsnThrAlaGlyMetTrpProArgCysProProGlyPheGluGlyArgProTyrLysS
3721 CTGGGGGCATGGGTAACTTTCCTGGAAGTGCATGGACGGTAATAGATAGGGGTCTAACC
 406▶ erGlyGlyMetGlyAsnPheProGlySerAlaTrpThrValIleAspArgGlySerAsnG
3781 AATGGCCAGCAGACGTGCGGGGCCATTCTCAGATCAACGATGGGCCCCCACAGAGCATG
 426▶ lnTrpProAlaAspValArgGlyProPheSerAspGlnArgTrpAlaProThrGluHisG
                                                            SacI
3841 AAACGCGACGTTTTTGCGGGTATTACAGCTGAGCTCTCATCATACCCATAACTCCACTCA
 446▶ luThrArgArgPheCysGlyTyrTyrSer···
3901 TAACCCAAGGCCCATAAATCCATAACTCATAACATAAATTCATACTTTCCGGTCGTCCAG
3961 GGCACCACGTCATCAACAAGGATTGCAGATAAATAAAAATGCTCCACGTTGTCGGTGTCC
4021 GTTGTATTGTATTCTTTATTATACCTCCGTAATTTTCGAGAGTCGGGGAACATTCTAAAA
4081 ATTTTAACCGTGCAATACTACAGTGTATTTACAAGGCCGGATTGCAACAGTGAACTCATT
          SacI
4141 ACATCATTGAGCTCGCGGCGCCATCTGCTGACCAGTCCACAGAGATGGCAATCTTCAGAA
4201 ACGTAGGATGGCACCAATTCCAATACAATACCGCCATCTGTCGATAGGTGTATAGAACTG
4261 TCAAAACAAGTCGCAAGAGAAAAATTTCCCTACTGTATACTGGCGGCTTAGCAGCTGCGC
 545◀···PheLeuAspCysSerPhePheLysGlyValThrTyrGlnArgSerLeuLeuGlnAla
4321 ACAAACCACTCTGCATTCCTCTTTGCGGCACACATTTGCGTGCTGCGCCAGAACGAGTGG
 525◀CysValValArgCysGluGluLysArgCysValAsnAlaHisGlnAlaLeuValLeuPro
4381 GATTTTTTTAGAACAGGTCCCAGGATAGTACATGTCCCACAATGTTCTGGCCGGGTCTAT
 505◀IleLysLysSerCysThrGlyProTyrTyrMetAspTrpLeuThrArgAlaProAspIle
4441 TGCTTTATGATTCATGACCATGGCCTCTGGTCGCGGATACACAATTCTTGAGAACCGGTC
 485◀AlaLysHisAsnMetValMetAlaGluProArgProTyrValIleArgSerPheArgAsp
                                                           BglII
4501 GAAGAAGGTCAGTAATAAAGTTAAAGGACATTTTGCGCTACTCAGCGATAGCTCCTGAGA
 465◀PhePheThrLeuLeuLeuThrLeuProCysLysAlaSerSerLeuSerLeuGluGlnSer
4561 TCTAGTGGTATCTCTTAGTTGACTGCCAATGCTAGAGAGATAACACGGCAGGATTGGCCC
 445◀ArgThrThrAspArgLeuGlnSerGlyIleSerSerLeuTyrCysProLeuIleProGly
4621 CAGATGCATGGCTAGAGATTGACATGCGCAGTAGATGTTAGAGAAGATAGGATCGTGGGG
 425◀LeuHisMetAlaLeuSerGlnCysAlaCysTyrIleAsnSerPheIleProAspHisPro
        BstBI                                          SphI
4681 GTAAATCCTTTCATCTTCGAACTGATGCCAAAGCATCCATACAAGTGTCTCATCGCATGC
 405◀TyrIleArgGluAspGluPheGlnHisTrpLeuMetTrpValLeuThrGluAspCysAla
4741 AAAAAGTAGCTCTTCAAATGAGCAGTTCGCCAAATATACAGCTCGTGAAATTTTTGCCAA
 385◀PheLeuLeuGluGluPheSerCysAsnAlaLeuTyrValAlaArgSerIleLysAlaLeu
4801 CCTGGCTATATCCGGACGCGATGTCCAGCGGCCTTTCAGTGAAGCTGCGCGCCCACAAAA
 365◀ArgAlaIleAspProArgSerThrTrpArgGlyLysLeuSerAlaAlaArgGlyCysPhe
4861 CTGCTTCCACGAAGTGAATGCAGCATCTGCTGCAAGGTCAGATGATCCCGAAGACAAAAA
 345◀GlnLysTrpSerThrPheAlaAlaAspAlaAlaLeuAspSerSerGlySerSerLeuPhe
       ClaI
4921 TGCTGGAAAGCAGATTCCTCTATCACGATCGATATCATCACAATCATCATCATCCACTGC
 325◀AlaProPheCysIleGlyArgAspArgAspIleAspAspCysAspAspAspAspValAla
4981 CCGGTTTACCATGTCTAAAAGACATTTCTGATTTTCTAATCTTAACTCTTCAGTAATGCA
 305◀ArgAsnValMetAspLeuLeuCysLysGlnAsnGluLeuArgLeuGluGluThrIleCys
```

```
5041 CTTTCCGAGACCGCCAAATGCAGTTGCGGCCTTTTCAAAATATTGGGCCGGTGTTACGTT
 285◄ LysGlyLeuGlyGlyPheAlaThrAlaAlaLysGluPheTyrGlnAlaProThrValAsn
5101 TCGCAACTCCTTCGTTTCGGTCCGTGATGACGTTGGGCATCGGACAAAGTCTCTCCAAAT
 265◄ ArgLeuGluLysThrGluThrArgSerSerThrProCysArgValPheAspArgTrpIle
       BstBI
5161 CGGTCTTCGAAGTTCATCCCGATTTCTTTCCCAAGACCTGCGCGAATGCTTCAACGAAAC
 245◄ ProArgArgLeuGluAspArgAsnArgGluTrpSerArgArgSerHisLysLeuSerVal
5221 AGTAAAGATAGGCGCCCTATATCGCTTTTCTGGTGTACCTGCACGGCGCCTGGGTCTAGG
 225◄ ThrPheIleProAlaArgTyrArgLysGluProThrGlyAlaArgArgArgProArgPro
5281 GGGGATGCCTCTTCGGACTTGGATATGCGCACGGCCTCTCATAAACTTATTTCGAGGGCT
 205◄ ProIleGlyArgArgValGlnIleHisAlaArgGlyArgMetPheLysAsnArgProSer
5341 ACTGACCCGCCTTATGGAAGACCGTACGCTCATACCTGACTGGTTCTCGTAACGGGAACG
 185◄ SerValArgArgIleSerSerArgValSerMetGlySerGlnAsnGluTyrArgSerArg
       BstBI
5401 AGGCTCGCCATTCGAATAGCGACGGCGCCCCCTGTCACGTGAATCACGGACTCGTTTGGA
 165◄ ProGluGlyAsnSerTyrArgArgArgGlyArgAspArgSerAspArgValArgLysSer
                                                       BglII
5461 GCTACCGCGCCCAGATGACCGGGATCTGGAGCTACTTTCTGTAGAATGAGATCTGCGGCG
 145◄ SerGlyArgGlySerSerArgSerArgSerSerSerGluThrSerHisSerArgArgArg
5521 AATACAATGTGCTTCGTGGCGGGATTCTGACCTCGAGCGTGAACGGCCATCCAGGCGATC
 125◄ IleCysHisAlaGluHisArgSerGluSerArgSerArgSerArgGlyAspLeuArgAsp
5581 TTTTGTCCTTTCCGTTGCTGATCTCGCTTCGCTATGAGTACTTGTATTGGAAGATGATCT
 105◄ LysThrArgGluThrAlaSerArgAlaGluSerHisThrSerThrAsnSerSerSerArg
5641 GGAACGTGTCTCACGCCTATCTTTATTTATTCCAGATTTCTCCGGTCTCCCCATCGCAGT
  85◄ SerArgThrGluArgArgAspLysAsnIleGlySerLysGluProArgGlyMetAlaThr
5701 CAGTGGGTTGATGTACCGCGTGCACGTCAAAAAAAATGAAACCGCATACACAACGGTTGA
  65◄ LeuProAsnIleTyrArgThrCysThrLeuPhePheSerValAlaTyrValValThrSer
       SacI
5761 GACTTCTACGGACTCAGAACAGGTGTCGAGCTCGGAGCAGGTGCTGAGAGGTAAGCTGAC
  45◄ ValGluValSerGluSerCysThrAspLeuGluSerCysThrSerLeuProLeuSerVal
5821 AGTAATCTGGCACGCTGTTTGCGAGCTAATCCACTTGGCTTTTGAATGGTCTGGGCCACT
  25◄ ThrIleGlnCysAlaThrGlnSerSerIleTrpLysAlaLysSerHisAspProGlySer
       ORF E
5881 CCCAGTATACGTCATAACACATACACTGGAACCCACAAACTACAATTGCGGTCCAGTAGT
   5◄ GlyThrTyrThrMet                                 BamHI
5941 TGGTGCGAAATATTCACGCAGACATAATAATCTGCGAGAACTTCTGCGGATCCGACATGT
6001 AACTTAATCCCGTAATGTAGTGCGGCATACCGTCTAAACCGCAAACATCCGCTTAGTAGA
6061 ACACGCCCTAAAATCACCCACGAGTATACTTTGTACATTCTGACCGCCAGATGTTACTCC
6121 TTTCAAACAATGATACTCAGCCGTTAGAACTAGGGCTGTCTTCAAATGGACCAAATTCAG
6181 ACACAATACCGCACAACGTGTTTTAACATTTTATTGCCGTTCAAGGCCCGAACAATTTGT
                                                    287◄ ...ProGlyPheLeuLysAs
6241 TTTGTATCTTCTGTTCGTATTTAAATGCAATTATTACAATGCTCGCAATCGCAGCCACGC
 280◄ nGlnIleLysGlnGluTyrLysPheAlaIleIleValIleSerAlaIleAlaAlaValCy
6301 ACAATGCACGCAAGACTAAGCTCGAAGCAATATTGGCAAGGCATGAAGTCAAGATACTGG
 260◄ sLeuAlaArgLeuValLeuSerSerAlaIleAsnAlaLeuCysSerThrLeuIleSerPr
6361 GAGGTTTCGATGCGGAGACTTTAGTCTTTGCCGGAGTCGTGTAACCCATCAGTGATAAGA
 240◄ oProLysSerAlaSerValLysThrLysAlaProThrThrTyrGlyMetLeuSerLeuLe
       XbaI
6421 GTTCTAGAACCGCTGAGACAATTACATATACCCAAGCACTAATTTTTACGTGTTCATGTA
 220◄ uGluLeuValAlaSerValIleValTyrValTrpAlaSerIleLysValHisGluHisLe
```

```
6481 AAATATATGCACACGGATCATAGCAAATCCGCAATGTCATGGTGGACATAATAAGCGATG
 200◀uIleTyrAlaCysProAspTyrCysIleArgLeuThrMetThrSerMetIleLeuSerAl
6541 CTAAATATAAACCGATCTCGAGTGTTTTCAGTAGTAAGACCCCTGGATTACAGACGCAAA
 180◀aLeuTyrLeuGlyIleGluLeuThrLysLeuLeuLeuValGlyProAsnCysValCysPh
6601 ATCCTAGAGGGTCTGCTACGTAGTTCAAGCTTTTGCAATCTCGGAGATGTTCAAATTCCC
 160◀eGlyLeuProAspAlaValTyrAsnLeuSerLysCysAspArgLeuHisGluPheGluAr
6661 TCAAAAACCGTTGCATCTTTGTGTATGGCACCCGTAATATCAGCCTCGAAGTAAACGCTG
 140◀gLeuPheArgGlnMetLysThrTyrProValArgLeuIleLeuArgSerThrPheAlaTh
6721 TCCAGTAGTTAAGATGATATGCATCCATCGCAATGCGTTCTCGCGGCAGACATAGCCCGA
 120◀rTrpTyrAsnLeuHisTyrAlaAspMetAlaIleArgGluArgProLeuCysLeuGlyPh
6781 ACATTCGCCTCTGGCGACGGGTCAGCAAGTAACATATGTACAATACCGTCGAAATGAATG
 100◀eMetArgArgGlnArgArgThrLeuLeuTyrCysIleTyrLeuValThrSerIlePheAl
6841 CAACTCTGATCTGGGAAAACCATATGTAAAGCAGACAGTCTGCCACTTCCATGACGAATA
  80◀aValArgIleGlnSerPheTrpIleTyrLeuLeuCysAspAlaValGluMetValPheVa
6901 CTGTTCTTTGGCCGGTGGGATCAAGACGAGAAATGAGTACAGTCTCATTTTCAAAATAAG
  60◀lThrArgGlnGlyThrProAspLeuArgSerIleLeuValThrGluAsnGluPheTyrAl
6961 CTCCTTTAACACATCTCGTCTGGTGGTTCTCGTAGTTGTTTAGACGCTGTGTATATTTTG
  40◀aGlyLysValCysArgThrGlnHisAsnGluTyrAsnAsnLeuArgGlnThrTyrLysTh
                                                            EcoRI
7021 TGAGGACATAAACTAGTGAAGAATTAAATGTAGCGGGGGTTGGTGAACAGGATTGAATT
  20◀rLeuValTyrValLeuSerSerAsnPheThrAlaProProGlnHisValProAsnPheGl
     (COL F)
7081 CC
   0◀u
```

| | FIG. 2A |
|---|---|
| | FIG. 2B |
| FIG. 2 | FIG. 2C |
| | FIG. 2D |
| | FIG. 2E |
| | FIG. 2F |

FIG. 2F

```
   1 TGCTACCTGATGTACAAGCAAAAGGCACAACAAAAGACCTTGTTATGGCTTGGGAATAAT
  61 ACCCTTGATCAGATGAGAGCCACTACAAAAATATGAATACAAACGAGAGGCGGAGGTATC
 121 CCCAATAGCAATTTGCGTGTAAATTCTGGCAACCTGTTAATTAGAAGAATTAAGAAAAAA
 181 CCACTGGATGTAAGTGACAAACAAGCAATACACGGGTAGAACGGTCGGAGAAGCCACCCC
 241 TCAATCGGGAATCAGGCCTCACAACGTCCTTTCTACCGCATCATCAATAGCAGACTTCGG
 301 TCATGGACCGTGCAGTTAGCAGAGTTGCGCTAGAGAATGAAGAAAGAGAAGCAAAGAATA
     1▶MetAspArgAlaValSerArgValAlaLeuGluAsnGluGluArgGluAlaLysAsnT
 361 CATGGCGCTTTGTATTCCGGATTGCAATCTTACTTTTAATAGTAACAACCTTAGCCATCT
    20▶hrTrpArgPheValPheArgIleAlaIleLeuLeuLeuIleValThrThrLeuAlaIles
 421 CTGCAACCGCCCTGGTATATAGCATGGAGGCTAGCACGCCTGGCGACCTTGTTGGCATAC
    40▶erAlaThrAlaLeuValTyrSerMetGluAlaSerThrProGlyAspLeuValGlyIleP
 481 CGACTATGATCTCTAAGGCAGAAGAAAGATTACATCTGCACTCAGTTCTAATCAAGATG
    60▶roThrMetIleSerLysAlaGluGluLysIleThrSerAlaLeuSerSerAsnGlnAspV
 541 TAGTAGATAGGATATATAAGCAGGTGGCCCTTGAGTCTCCATTGGCGTTGCTAAACACTG
    80▶alValAspArgIleTyrLysGlnValAlaLeuGluSerProLeuAlaLeuLeuAsnThrG
 601 AATCTGTAATTATGAATGCAATAACGTCTCTCTCTTATCAAATCAATGGAGCTGCAAATA
   100▶luSerValIleMetAsnAlaIleThrSerLeuSerTyrGlnIleAsnGlyAlaAlaAsnA
                                                      BspHI
 661 ATAGCGGGTGTGGGGCACCTGTTCATGACCCAGATTATATCGGGGGGATAGGCAAAGAAC
   120▶snSerGlyCysGlyAlaProValHisAspProAspTyrIleGlyGlyIleGlyLysGluL
 721 TTATTGTGGATGACGCTAGTGATGTCACATCATTCTATCCCTCTGCGTTCCAAGAACACC
   140▶euIleValAspAspAlaSerAspValThrSerPheTyrProSerAlaPheGlnGluHisL
 781 TGAACTTTATCCCGGCACCTACTACAGGATCAGGTTGCACTCGGATACCCTCATTCGACA
   160▶euAsnPheIleProAlaProThrThrGlySerGlyCysThrArgIleProSerPheAspI
 841 TAAGCGCTACCCACTACTGTTACACTCACAATGTGATATTATCTGGTTGCAGAGATCACT
   180▶leSerAlaThrHisTyrCysTyrThrHisAsnValIleLeuSerGlyCysArgAspHisS
 901 CACACTCATATCAGTACTTAGCACTTGGCGTGCTTCGGACATCTGCAACAGGGAGGGTAT
   200▶erHisSerTyrGlnTyrLeuAlaLeuGlyValLeuArgThrSerAlaThrGlyArgValP
 961 TCTTTTCTACTCTGCGTTCCATCAATTTGGATGACAGCCAAAATCGGAAGTCTTGCAGTG
   220▶hePheSerThrLeuArgSerIleAsnLeuAspAspSerGlnAsnArgLysSerCysSerV
1021 TGAGTGCAACTCCCTTAGGTTGTGATATGCTGTGCTCTAAAATCACAGAGACTGAGGAAG
   240▶alSerAlaThrProLeuGlyCysAspMetLeuCysSerLysIleThrGluThrGluGluG
                                                      ClaI
1081 AGGATTATAGTTCAATTACGCCTACATCGATGGTGCACGGAAGGTTAGGGTTTGACGGTC
   260▶luAspTyrSerSerIleThrProThrSerMetValHisGlyArgLeuGlyPheAspGlyG
1141 AATACCATGAGAAGGACTTAGACGTCATAACTTTATTTAAGGATTGGGTGGCAAATTACC
   280▶lnTyrHisGluLysAspLeuAspValIleThrLeuPheLysAspTrpValAlaAsnTyrP
1201 CAGGAGTGGGGGGTGGGTCTTTTATTAACAACCGCGTATGGTTCCCAGTCTACGGAGGGC
   300▶roGlyValGlyGlyGlySerPheIleAsnAsnArgValTrpPheProValTyrGlyGlyL
1261 TAAAACCCAATTCGCCTAGTGACACCGCACAAGAAGGGAGATATGTAATATACAAGCGCT
   320▶euLysProAsnSerProSerAspThrAlaGlnGluGlyArgTyrValIleTyrLysArgT
1321 ACAATGACACATGCCCAGATGAACAAGATTACCAGATTCGGATGGCTAAGTCTTCATATA
   340▶yrAsnAspThrCysProAspGluGlnAspTyrGlnIleArgMetAlaLysSerSerTyrL
1381 AGCCTGGGCGGTTTGGTGGAAAACGCGTACAGCAGGCCATCTTATCTATCAAGGTGTCAA
   360▶ysProGlyArgPheGlyGlyLysArgValGlnGlnAlaIleLeuSerIleLysValSerT
1441 CATCTTTGGGCGAGGACCCGGTGCTGACTGTACCGCCTAATACAATCACACTCATGGGGG
   380▶hrSerLeuGlyGluAspProValLeuThrValProProAsnThrIleThrLeuMetGlyA
1501 CCGAACGGAGAGTTCTCACAGTAGGGACATCTCATTTCTTGTACCAGCGAGGGTCTTCAT
   400▶laGluArgArgValLeuThrValGlyThrSerHisPheLeuTyrGlnArgGlySerSerT
```

FIG. 10A

| FIG. 10 | FIG. 10A |
|---|---|
|  | FIG. 10B |

```
1561 ACTTCTCTCCTGCTTTATTATACCCTATGACAGTCAACAACAAAACGGCTACTCTTCATA
 420▶ yrPheSerProAlaLeuLeuTyrProMetThrValAsnAsnLysThrAlaThrLeuHisS
1621 GTCCTTACACATTCAATGCTTTCACTAGGCCAGGTAGTGTCCCTTGTCAGGCATCAGCAA
 440▶ erProTyrThrPheAsnAlaPheThrArgProGlySerValProCysGlnAlaSerAlaA
1681 GATGCCCCAACTCATGTGTCACTGGAGTTTATACTGATCCGTATCCCTTAGTCTTCCATA
 460▶ rgCysProAsnSerCysValThrGlyValTyrThrAspProTyrProLeuValPheHisA
1741 GGAACCATACCTTGCGGGGGGTATTCGGACAATGCTTGATGATGAACAAGCAAGACTTA
 480▶ rgAsnHisThrLeuArgGlyValPheGlyThrMetLeuAspAspGluGlnAlaArgLeuA
                   PstI
1801 ACCCTGTATCTGCAGTATTTGATAACATATCCCGCAGTCGCATAACCCGGGTAAGTTCAA
 500▶ snProValSerAlaValPheAspAsnIleSerArgSerArgIleThrArgValSerSerS
1861 GCCGTACTAAGGCAGCATACACGACATCGACATGTTTTAAAGTTGTCAAGACCAATAAAA
 520▶ erArgThrLysAlaAlaTyrThrThrSerThrCysPheLysValValLysThrAsnLysT
1921 CATATTGCCTCAGCATTGCAGAAATATCCAATACCCTCTTCGGGGAATTCAGGATCGTTC
 540▶ hrTyrCysLeuSerIleAlaGluIleSerAsnThrLeuPheGlyGluPheArgIleValP
1981 CTTTACTAGTTGAGATTCTCAAGGATGATGGGATTTAAGAAGCCAGGTCTGGCCAGTTGA
 560▶ roLeuLeuValGluIleLeuLysAsp
2041 GTCAACTGCGAGAGGGTCGGAAAGATGACATTGTGTCACCTTTTTTTTGTAATGCCAAGG
2101 ATCAAACTGGATACCGGCGCGAGCCCGAATCCTATGCTGCCAGTCAGCCATAATCAGATA
2161 GTACTAATATGATTAGTCTTAATCTTGTCGATAGTAACTTGGTTAAGAAAAAATATGAGT
2221 GGTAGTGAGATACACAGCTAAACAACTCACGAGAGATAGCACGGGTAGGACATGGCGAGC
2281 TCCGGTCCCGAAGGGCAGAGCATCAGATTATCCTACCAGAGTCACATCTGTCCTCACCA
2341 TTGGTCAAGCACAAACTGCTCTATTACTGGAAATTAACTGGCGTACCGCTTCCTGACGAA
2401 TGTGACTTCGACCACCTCATTATCAGCCGACAATGGAAGAAAATACTTGAATCGGCCACT
2461 CCTGACACTGAGAGGATGATAAAGCTCGGGCGGGCAGTACACCAGACTCTCGACCACCGC
2521 C
```

EcoRI
(UL53)

```
   1 GAATTCAATCCTGTTCACCAACCCCCGCTACATTTAATTCTTCACTAGTTTATGTCCTC
   1▶ GluPheAsnProValHisGlnProProAlaThrPheAsnSerSerLeuValTyrValLeu
  61 ACAAAATATACACAGCGTCTAAACAACTACGAGAACCACCAGACGAGATGTGTTAAAGGA
  21▶ ThrLysTyrThrGlnArgLeuAsnAsnTyrGluAsnHisGlnThrArgCysValLysGly
 121 GCTTATTTTGAAAATGAGACTGTACTCATTTCTCGTCTGATCCCACTGGCCAAAGAACAG
  41▶ AlaTyrPheGluAsnGluThrValLeuIleSerArgLeuIleProLeuAlaLysGluGln
 181 TATTCGTCATGGAAGTGGCAGACTGTCTCTTTACATATGGTTTTCCCAGATCAGAGTTGC
  61▶ TyrSerSerTrpLysTrpGlnThrValSerLeuHisMetValPheProAspGlnSerCys
 241 ATTTCCACGGTTATTGTACATATGTTACTTGCTGACCCGTGCCAGAGGCGAATGTTCGGC
  81▶ IleSerThrValIleValHisMetLeuLeuAlaAspProCysGlnArgArgMetPheGly
 301 TCTGTCTGCCGCGAGAACGCATTGCGATTGGATGCATATCATCTAAACTACTGGACAGCG
 101▶ SerValCysArgGluAsnAlaLeuArgLeuAspAlaTyrHisLeuAsnTyrTrpThrAla
 361 TTTACTTCGAGGCTGATATTACGGGTGCCATACACAAAGATGCAACGGTTTTTGAGGGAA
 121▶ PheThrSerArgLeuIleLeuArgValProTyrThrLysMetGlnArgPheLeuArgGlu
 421 TTTGAACATGTCCGAGATTGCAAAAGCTTGAACTACGTAGCAGACCCTCTAGGCTTTTGC
 141▶ PheGluHisValArgAspCysLysSerLeuAsnTyrValAlaAspProLeuGlyPheCys
 481 ATCTGTAATCCAGGGGTCTTAGTACTGAAAACACTCGAGATCGGTTTATATTTAGCATCG
 161▶ IleCysAsnProGlyValLeuValLeuLysThrLeuGluIleGlyLeuTyrLeuAlaSer
 541 CTTATTATGTCCACCATGACATTGCGGATTTGCTATGATCCGTGTGCATATATTTTACAT
 181▶ LeuIleMetSerThrMetThrLeuArgIleCysTyrAspProCysAlaTyrIleLeuHis
 601 GAACACGTAAAAATTAGTGCTTGGGTATATGTAATTGTCTCAGCGGTTCTAGAACTCTTA
 201▶ GluHisValLysIleSerAlaTrpValTyrValIleValSerAlaValLeuGluLeuLeu
 661 TCACTGATGGGTTACACGACTCCGGCAAAGACTAAAGTCTCCGCATCGAAACCTCCCAGT
 221▶ SerLeuMetGlyTyrThrThrProAlaLysThrLysValSerAlaSerLysProProSer
 721 ATCTTGACTTCATGCCTTGCCAATATTGCTTCGAGCTTAGTCTTGCGTGCATTGTGCGTG
 241▶ IleLeuThrSerCysLeuAlaAsnIleAlaSerSerLeuValLeuArgAlaLeuCysVal
 781 GCTGCGATTGCGAGCATTGTAATAATTGCATTTAAATACGAACAGAAGATACAAAACAAA
 261▶ AlaAlaIleAlaSerIleValIleIleAlaPheLysTyrGluGlnLysIleGlnAsnLys
 841 TTGTTCGGGCCTTGAACGGCAATAAAATGTTAAAACACGTTGTGCGGTGTTGTGTCTGAA
 281▶ LeuPheGlyPro•••
 901 TTTGGTCCATTTGAAGACAGCCCTAGTTCTAACGGCTGAGTATCATTGTTTGAAAGGAGT
 961 AACATCTGGCGGTCAGAATGTACAAAGTATACTCGTGGGTGATTTTAGGGCGTGTTCTAC
1021 TAAGCGGATGTTTGCGGTTTAGACGGCATGCCGCACTACATTACGGGATTAAGTTACATG
         BamHI
1081 TCGGATCCGCAGAAGTTCTCGCAGATTATTATGTCTGCGTGAATATTTCGCACCAACTAC
1141 TGGATCGCAATTGTAGTTTGTGGGTTCCAGTGTATGTGTTATGACGTATACTGGGAGTGG
1201 CCCAGACCATTCAAAAGCCAAGTGGATTAGCTCGCAAACAGCGTGCCAGATTACTGTCAG
1261 CTTACCTTTCAGCACCTGCTCCGAGCTTGACACCTGTTCTGAGTCCGTAGAAGTCTCAAC
1321 CGTTGTGTATGCGGTTTCATTTTTTTGACGTGCACGCGGTACATCAACCCACTGACTGC
1381 GATGGAGACCGGAGAAATCTGGAAGAAATAAAGATAGCGTGAGACACGTTCAGAGCATCT
1441 TCAATACAAGTACTCATAGCGAAGCGAGATCAGCAACGGCCCGGACAAAGATCGCCCTG
                                                              BglII
1501 GATGGCCGTTCACGCTGAGGTCAGAATCCCGCCACGAAGCACATTGTATTCGCCGCAGAT
1561 CTCATTCTACAGAAAGTAGCTCCAGATCCCGGTTCATCTGGGCGCGGTACGTCCAAACGA
```

| FIG. 18A |
|---|

| FIG. 18 | FIG. 18A |
|---|---|
| | FIG. 18B |

UL54

```
1621 GTCCGTGATTCAAGTGACAGGGGGCGCCGTCGCTGTTCGAATGGCGAGGCCTCGTTCCCG
    1▶ MetAlaArgProArgSerAr
1681 TTACGAGAACCAGTCAGGTATGAGCGTACGGTCTTCCATAAGGCGGGTCAGTAGCCCTCG
    7▶ gTyrGluAsnGlnSerGlyMetSerValArgSerSerIleArgArgValSerSerProAr
1741 AAATAAGTTTATGAGAGGCCGTGCGCATATCCAAGTCCGAAGAGGCATCCCCCCTAGACC
   27▶ gAsnLysPheMetArgGlyArgAlaHisIleGlnValArgArgGlyIleProProArgPr
1801 CAGGCGCCGTGCAGGTACACCAGAAAAGCGATATAGGGCGCCTATCTTTACTGTTTCGTT
   47▶ oArgArgArgAlaGlyThrProGluLysArgTyrArgAlaProIlePheThrValSerLe
1861 GAAGCATTCGCGCAGGTCTTGGGAAAGAAATCGGGATGAACTTCGAAGACCGATTTGGAG
   67▶ uLysHisSerArgArgSerTrpGluArgAsnArgAspGluLeuArgArgProIleTrpAr
1921 AGACTTTGTCCGATGCCCAACGTCATCACGGACCGAAACGAAGGAGTTGCGAAACGTAAC
   87▶ gAspPheValArgCysProThrSerSerArgThrGluThrLysGluLeuArgAsnValTh
1981 ACCGGCCCAATATTTTGAAAAGGCCGCAACTGCATTTGGCGGTCTCGGAAAGTGCATTAC
  107▶ rProAlaGlnTyrPheGluLysAlaAlaThrAlaPheGlyGlyLeuGlyLysCysIleTh
2041 TGAAGAGTTAAGATTAGAAAATCAGAAATGTCTTTTAGACATGGTAAACCGGGCAGTGGA
  127▶ rGluGluLeuArgLeuGluAsnGlnLysCysLeuLeuAspMetValAsnArgAlaValAs
```
ClaI
```
2101 TGATGATGATTGTGATGATATCGATCGTGATAGAGGAATCTGCTTTCCAGCATTTTTGTC
  147▶ pAspAspAspCysAspAspIleAspArgAspArgGlyIleCysPheProAlaPheLeuSe
2161 TTCGGGATCATCTGACCTTGCAGCCGATGCTGCATTCACTTCGTGGAAGCAGTTTTGTGG
  167▶ rSerGlySerSerAspLeuAlaAlaAspAlaAlaPheThrSerTrpLysGlnPheCysGl
2221 GCGCGCAGCTTCACTGAAAGGCCGCTGGACATCGCGTCCGGATATAGCCAGGTTGGCAAA
  187▶ yArgAlaAlaSerLeuLysGlyArgTrpThrSerArgProAspIleAlaArgLeuAlaLy
2281 AATTTCACGAGCTGTATATTTGGCGAACTGCTCATTTGAAGAGCTACTTTTTGCATGCGA
  207▶ sIleSerArgAlaValTyrLeuAlaAsnCysSerPheGluGluLeuLeuPheAlaCysAs
2341 TGAGACACTTGTATGGATGCTTTGGCATCAGTTCGAAGATGAAAGGATTTACCCCCACGA
  227▶ pGluThrLeuValTrpMetLeuTrpHisGlnPheGluAspGluArgIleTyrProHisAs
2401 TCCTATCTTCTCTAACATCTACTGCGCATGTCAATCTCTAGCCATGCATCTGGGCCAAT
  247▶ pProIlePheSerAsnIleTyrCysAlaCysGlnSerLeuAlaMetHisLeuGlyProIl
```
BglII
```
2461 CCTGCCGTGTTATCTCTCTAGCATTGGCAGTCAACTAAGAGATACCACTAGATCTCAGGA
  267▶ eLeuProCysTyrLeuSerSerIleGlySerGlnLeuArgAspThrThrArgSerGlnGl
2521 GCTATCACTGAGTAGCGCAAAATGTCCTTTAACTTTATTACTGACCTTCTTCGACCGGTT
  287▶ uLeuSerLeuSerSerAlaLysCysProLeuThrLeuLeuLeuThrPhePheAspArgPh
2581 CTCAAGAATTGTGTATCCGCGATCAGAGGCCATAGTCATGAATCATAAAGCAATAGACCC
  307▶ eSerArgIleValTyrProArgSerGluAlaIleValMetAsnHisLysAlaIleAspPr
2641 GGCCAGAACATTGTGGACATGTACTATCCTGGGACCTGTTCTAAAAAAATCCCACTCGT
  327▶ oAlaArgThrLeuTrpAspMetTyrTyrProGlyThrCysSerLysLysIleProLeuVa
2701 TCTGCGCAGCACGCAAATGTGTGCCGCAAAGAGGAATGCAGAGTGGTTTGTGCGCAGCTC
  347▶ lLeuArgSerThrGlnMetCysAlaAlaLysArgAsnAlaGluTrpPheValArgSerSe
2761 TAAGCCGCAGTATACAGTAGGGAAATTTTCTCTTGCGACTTGTTTGACAGTTCTATACAC
  367▶ rLysProGlnTyrThrValGlyLysPheSerLeuAlaThrCysLeuThrValLeuTyrTh
2821 CTATCGACACATGGCGGTATTGTATTGGAATTGGTGCCATCCTACGTTTCTGAAGATTGC
  387▶ rTyrArgHisMetAlaValLeuTyrTrpAsnTrpCysHisProThrPheLeuLysIleAl
```
SacI
```
2881 CATCTCTGTGACTGGTCAGCAGATGGCGCCGCGAGCTCAATGATGTAAGCGTTCACTGTT
  407▶ aIleSerValThrGlyGlnGlnMetAlaProArgAlaGln···
2941 GCAATCCGGCCTTGTAAATACACTGTAGTATTAGCACGGTTGAAAATTTTTAGAATGTTC
3001 CCCGACTCTCGAAAATTAACGGAGGTATAATAAAGAACACAATACAACGGACACCGACAA
3061 CGTGGAGCATTTTTATTTAGTCTGCAAATCCTTGGTTGATGAACGTGGTGCCCTGG
```

AVIAN RECOMBINANT LIVE VACCINE USING, AS VECTOR, THE AVIAN INFECTIOUS LARYNGOTRACHEITIS

CROSS-REFERENCE TO RELATED APPLICATIONS

This is a continuation of copending International Application PCT/FR98/00122 having an international filing date of Jan. 23, 1998.

STATEMENT REGARDING FEDERALLY SPONSORED RESEARCH OR DEVELOPMENT

Not applicable.

FIELD OF THE INVENTION

The present invention relates to vaccines for avian use based on infectious laryngotracheitis virus (ILTV) into which there has been inserted, by genetic recombination, at least one heterologous nucleotide sequence in particular encoding and expressing an antigenic polypeptide from an avian pathogenic agent, under conditions ensuring immunization leading to effective protection of the vaccinated animal against the said pathogenic agent.

BACKGROUND OF THE INVENTION

The infectious laryngotracheitis virus (ILTV) is an alphaherpesvirus (B. Roizman, *Arch. Virol.* 1992. 123. 425–449) which causes a major respiratory pathology (infectious laryngotracheitis or ILT) in chicken (L. E. Hanson and T. J. Bagust, *Diseases of Poultry* 9th edn 1991. pp 485–495. Ames, Iowa State University Press). The vaccines currently available against this condition contain an attenuated strain which can be administered by various routes including the intranasal, conjunctival and cloacal routes, in drinking water and by aerosol (L. E. Hanson and T. J. Bagust (1991).

Studies of the molecular biology of the ILTV virus have made it possible to characterize the viral genome (M. A. Johnson et al., *Arch. Virol.* 1991. 119. 181–198) and to identify some of the virus genes (A. M. Griffin, *J. Gen. Virol.* 1989. 70. 3085–3089) including the genes encoding thymidine kinase (UL23) (A. M. Griffin and M. E. G. Boursnell, *J. Gen. Virol.* 1990. 71. 841–850; C. L. Keeler et al., *Avian Dis.* 1991. 35. 920–929), the glycoprotein gB (UL27) (A. M. Griffin, *J. Gen. Virol.* 1991. 72. 393–398; K. Kongsuwan et al., *Virology* 1991. 184. 404–410; D. J. Poulsen et al., *Virus Genes* 1991. 5. 335–347), the glycoprotein gC (UL44) (D. H. Kingsley et al., *Virology* 1994. 203. 336–343), the capsid protein p40 (UL26) (A. M. Griffin, *Nucl. Acids Res.* 1990. 18. 3664), the protein homologous to the ICP4 protein of herpes simplex (HSV-1) (M. A. Johnson et al., *Virus Research* 1995. 35. 193–204), the proteins homologous to the proteins ICP27 (UL54), glycoprotein gK (UL53) and DNA helicase (UL52) from HSV-1 (M. A. Johnson et al., *Arch. Virol.* 1995. 140. 623–634), ribonucleotide reductase (A. M. Griffin, (1989); and WO-A-90/02802), the UL1 to UL5 genes (W. Fuchs and T. C. Mettentleiter, *J. Gen. Virol.* 1996. 77. 2221–2229), the genes present in the short unique sequence of the genome (U$_s$) (M. A. Johnson et al., *DNA Sequence—The Journal of Sequencing and Mapping* 1995. Vol. 5. pp 191–194; K. Kongsuwan et al., *Arch. Virol.* 1995. 140. 27–39; K. Kongsuwan et al., *Virus Research* 1993. 29. 125–140; K. Kongsuwan et al., *Virus Gene* 1993. 7. 297–303; M. A. Wild et al., *Virus Genes* 1996. 12. 107–116; WO-A-92/03554; and WO-A-95/08622).

BRIEF SUMMARY OF THE INVENTION

The aim of the present invention is to develop an avian vaccine based on recombinant ILTV virus expressing a heterologous gene, this virus being capable of replicating and inducing immunity in the vaccinated host while preserving good safety.

Another aim of the invention is to provide such a vaccine which is at the same time particularly effective against ILT.

Another aim of the invention is to provide such a vaccine which can be used in mass vaccination by the mucosal route, for example by the aerosol route or in drinking water, such that the replication of the virus at the mucosal level makes it possible to induce mucosal and systemic immunity. Such a mucosal immunity will be particularly effective for combating respiratory diseases as well as other diseases for which the route of entry of the pathogenic agent is mucosal.

Another aim of the invention is to provide such a vaccine which can be used both in adults and in young animals.

A specific aim is to provide such a vaccine which can be used in mass vaccination, by the mucosal route, of any young animals such as one-day old chicks.

Another aim of the invention is to provide a vaccine against ILT which has an increased efficacy compared with the parental strain and which may even possibly allow the insertion and expression of a heterologous gene.

BRIEF DESCRIPTION OF THE DRAWINGS

FIG. 2 shows the DNA sequence of SEQ ID NO: 1 and the translation products of ORFs A (SEQ ID NO: 2), B (SEQ ID NO: 3), C (SEQ ID NO: 4), D (SEQ ID NO: 5), E (SEQ ID NO: 6) and F (SEQ ID NO: 7) of the vaccinal strain T-20 from Select Laboratories.

FIG. 10 shows the DNA sequence of the NDV HN gene (SEQ ID NO: 8) and the expression product thereof (SEQ ID NO: 9).

FIG. 18 shows a DNA sequence of strain SA-2 from the ECORI site at position 1696 of the Genbank sequence, accession No. L34065, (SEQ ID NO: 10) and translation products thereof UL53 (SEQ ID NO: 11) and UL54 (SEQ ID NO: 12) SA-2.

DETAILED DESCRIPTION OF THE INVENTION

Figure 1:
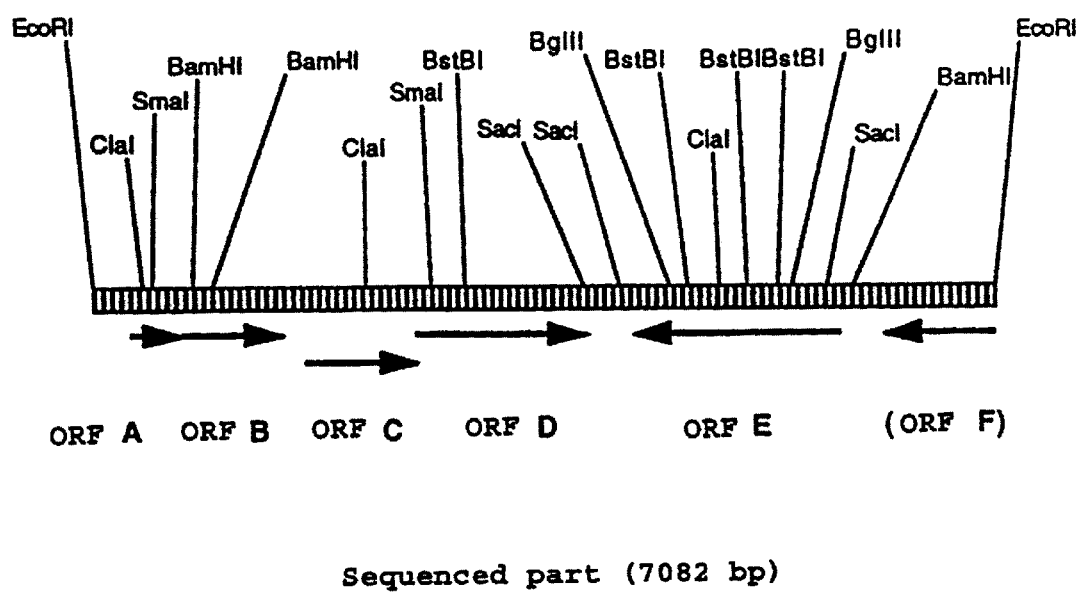
FIG. 1 shows a restriction map of the cloned fragment (SEQ ID NO:1) and positions of the ORFs (SEQ ID NOs:2–7).

During their studies on the ILTV virus, the inventors found a genomic region which proved entirely appropriate as site for insertion of heterologous genes. This made it possible to develop a recombinant live vaccine based on an ILTV vector into which is inserted at least one sequence encoding an avian immunogen, in particular the HN and F proteins from the Newcastle disease virus (NDV), and/or the gB glycoprotein from Marek's disease virus (MDV), and/or the VP2 protein from the infectious bursal disease virus (IBDV), and/or the S and M proteins from the infectious bronchitis virus (IBV). Such a vaccine, incorporating a sequence encoding NDV, MDV and IBV proteins, provides satisfactory protection of the animals against Newcastle disease, against Marek's disease, against infectious bursal disease and against infectious bronchitis respectively.

The subject of the present invention is therefore an avian recombinant live vaccine comprising, as vector, the ILTV comprising at least one heterologous nucleotide sequence in particular encoding and expressing an antigenic polypeptide from an avian pathogenic agent, inserted into the insertion locus formed by the intergenic region situated between the "stop" codons of the ORF-D and ORF-E of the ILTV and which, in a specific ILTV strain, is defined between nucleotides 3873 and 4260 in the sequence SEQ ID NO:1

While the specific sequence described in the application (SEQ ID NO:1) is obtained from the vaccinal strain of ILTV T-20 12-8-66 (LT BLEN vaccine) obtained from Select Laboratories (10026 Main Street P.O. Box 6 Berlin, Md. 21811, USA), it is quite obvious that persons skilled in the art will be able to use the other ILTV strains, taking into account the information given in the present text on the vaccinal strain.

The ORF-E corresponds to the UL54 gene described in the article by M. A. Johnson et al. (*Arch. Virol.* 1995. 140. 623–634) for the Australian vaccinal strain SA-2. The nucleotide sequence of the UL54 gene of the SA-2 strain is slightly different from that of the T-20 strain, which causes differences between the amino acid sequences of the genes of these two strains, and in particular the C-terminal part (different STOP codons). This article does not suggest in any manner that the sequence downstream of the UL54 gene can be used as insertion locus.

The sequence designated by the reference SEQ ID NO:10 reproduces for this SA-2 strain part of the sequence equivalent to SEQ ID NO: 1 (in the opposite direction). The intergenic region serving as insertion locus in accordance with the invention is partly comprised in SEQ ID NO:10 between nucleotides 2808 and 3116 (last nucleotide of this sequence).

Heterologous sequence is understood to mean a sequence which is not derived from the insertion locus, that is to say both a sequence not originating from the ILTV and a sequence derived from another genomic region of this virus, or alternatively originating from another ILTV strain, particularly a virulent strain.

Insertion into the insertion region is understood to mean in particular simple insertion or insertion after total or partial deletion of the insertion locus.

One or more expression cassettes may be inserted, each comprising at least one sequence to be expressed.

To express the inserted sequence, the use of a strong eukaryotic promoter such as the CMV immediate early (IE) promoter, the Rous sarcoma virus (RSV) LTR and the SV40 virus early promoter is preferred.

CMV immediate early (IE) promoter is understood in particular to mean the fragment given in the examples as well as its subfragments which retain the same promoter activity.

The CMV IE promoter may be the human promoter (HCMV IE) or the murine promoter (MCMV IE) or alternatively a CMV IE promoter of another origin, for example from monkeys, rats, guinea pigs or pigs.

Other promoters of viral or cellular origin can also be used. Among the promoters of viral origin, there may also be mentioned the promoters of genes of the ILTV (genes considered as early-immediate (ICP4, ICP27 and the like), early (thymidine kinase, DNA helicase, ribonucleotide reductase and the like), or late (gB, gD, gC, gK and the like)), of Marek's disease virus (MDV) (gB, gC, pp38, pp14, ICP4 and Meq genes and the like) or of the turkey herpesvirus (gB, gC and ICP4 genes and the like).

The nucleotide sequence inserted into the ILTV vector so as to be expressed may be any sequence encoding an antigenic polypeptide, from an avian pathogenic agent, capable, once expressed under the favourable conditions offered by the invention, of providing immunization leading to effective protection of the animal vaccinated against the pathogenic agent. It will therefore be possible to insert, under the conditions of the invention, the nucleotide sequences encoding antigens of interest for a given disease.

This nucleotide sequence inserted into the ILTV vector may also encode an immunomodulatory polypeptide, especially a cytokine.

Remarkably, it will be possible for the vaccines according to the invention to be used for accination in ovo of one-day-old or older chicks and of adults. It will be possible to use various routes of dministration: the parenteral route, or the mucosal routes such as the oronasal (drinking water, aerosol), conjunctival (eye drop) or cloacal route, with a preference for the routes allowing mass mucosal vaccination (drinking water, aerosol).

The invention proves particularly useful both for protection against respiratory pathologies and against systemic pathologies by blocking the natural routes of entry of the pathogenic agent.

The invention may in particular be used for the insertion of a nucleotide sequence appropriately encoding an antigenic protein from the NDV virus, and in particular the HN glycoprotein or the F glycoprotein. A recombinant live vaccine is thus obtained providing, in addition to protection against infectious laryngotracheitis, satisfactory protection against Newcastle disease.

The recombinant vaccine against Newcastle disease will preferably contain from 10 to $10^4$ PFU/dose.

Other preferred cases of the invention are the insertion of nucleotide sequences encoding antigens from other avian pathogenic agents and in particular, but with no limitation being implied, antigens from Marek's disease, in particular gB, gC, gD and gH+gL genes (WO-A-90/02803), from the infectious bursal disease virus, in particular VP2 gene, from the infectious bronchitis virus (IBV), in particular S and M genes (M. Binns et al., *J. Gen. Virol.* 1985, 66. 719–726; M. Boursnell et al., *Virus Research* 1984. 1. 303– 313), from the chicken anaemia virus (CAV), in particular VP1 (52 kDa) +VP2 (24 kDa) (N. H. M. Noteborn et al., *J. Virol.* 1991. 65. 3131–3139), from the ILTV, in particular the genes coding for gB (A. M. Griffin, *J. Gen. Virol.* 1991. 72. 393–398), or for gD (M. A. Johnson et al., DNA Sequence—The Journal of Sequencing and Mapping 1995. Vol. 5. pp 191–194. Harwood Academic Publishers GmbH), or for gp60 (K. K. Kongsuwan et al., *Virus Genes* 1993. 7. 297–303), and from the infectious "swollen head syndrome" virus (or chicken pneumovirosis or turkey rhinotracheitis virus (TRTV); pneumovirus), in particular the fusion glycoprotein F (Q. Yu et al., *J. Gen. Virol.* 1991. 72. 75–81), or the attachment glycoprotein G (R. Ling et al., J. Gen. Virol. 1992. 73.

1709–1715; K. Juhasz and J. Easton, *J. Gen. Virol* 1994. 75. 2873–2880). The doses will be preferably the same as those for the Newcastle vaccine.

Within the framework of the present invention, it is of course possible to insert more than one heterologous sequence into the same ILTV, in particular into this locus. It is possible in particular to insert therein sequences derived from the same virus or from different viruses, which also comprises the insertion of sequences from ILTV and from another avian virus. It is also possible to associate therewith sequences encoding immunomodulators, and in particular cytokines.

For example, the CMV IE promoter is associated with another promoter so that their 5' ends are adjacent (which implies transcriptions in opposite directions), which makes it possible to insert, into the insertion zone, two nucleotide sequences, one under the control of the CMV IE promoter, the other under that of the associated promoter. This construct is remarkable by the fact that the presence of the CMV IE promoter, and in particular of its activating (enhancer) part, activates the transcription induced by the associated promoter. The associated promoter may be in particular a promoter of a gene from the ILTV or from the MDV or HVT virus.

An advantageous case of the invention is a vaccine comprising a nucleotide sequence encoding NDV HN and a nucleotide sequence encoding NDV F or an antigen for another avian disease, especially those mentioned above, one of the genes being under the control of the CMV IE promoter, and the other under the control of the associated promoter.

It is also possible to assemble two CMV IE romoters of different origins with their 5' ends adjacent.

The expression of several heterologous genes inserted into the insertion locus may also be made possible by insertion between the open reading frames of these genes of a sequence called "IRES" (Internal Ribosome Entry Site) obtained especially from a picornavirus such as the swine vesicular disease virus (SVDV; B.-F. Chen et al.,*J. Virology*, 1993, 67, 2142–2148), the encephalomyocarditis virus (EMCV; R. J. Kaufman et al., *Nucleic Acids Research,* 1991, 19, 4485–4490), the foot-and-mouth disease virus (FMDV; N. Luz and E. Beck, *J. Virology,* 1991, 65, 6486–6494), or alternatively from another origin. The content of the 3 articles cited is incorporated by reference. The cassette for expression of two genes would therefore have the following minimum structure: promoter—gene 1—IRES—gene 2—polyadenylation signal. The recombinant live vaccine according to the invention may therefore comprise, inserted into the insertion locus, an expression cassette comprising in succession a promoter, two or more genes separated in pairs by an IRES, and a polyadenylation signal.

In addition to the insertion into the locus according to the invention, it is possible to carry out one or more other insertions, one or more mutations, or one or more deletions elsewhere in the genome; if the parental strain is virulent, it is possible, for example, to inactivate (by deletion, insertion or mutation) genes involved in the virulence, such as the thymidine kinase gene, the ribonucleotide reductase gene, the gE gene and the like. In any case, the insertion into a locus other than that described in the invention makes it possible to express other genes.

The subject of the present invention is also a vaccine against ILT, comprising a recombinant ILTV into which there has been inserted upstream of the genes encoding major ILTV immunogens, preferably the genes coding for gB (A. M. Griffin, *J. Gen. Virol.* 991. 72. 393–398), or for gD (M. A. Johnson et al., *DNA Sequence—The Journal of Sequencing and Mapping* 1995. Vol. 5. pp 191–194. Harwood Academic Publishers GmbH), or for gp6O (K. K. Kongsuwan et al., *Virus Genes* 1993. 7. 297–303), an exogenous promoter, in particular a strong promoter as described above. This makes it possible to increase the level of expression of one or more of these genes and thus to lead to a vaccine having increased efficacy against ILT. It is of course possible to combine this with a construction as described above comprising the insertion of a heterologous sequence into the insertion locus.

The subject of the present invention is also a multivalent vaccine formula comprising, as a mixture or to be mixed, a vaccine as defined above with another vaccine, and especially another avian recombinant live vaccine as defined above, these vaccines comprising different inserted sequences, especially from different pathogens.

The subject of the present invention is also a method for preparing the vaccines according to the invention, as evident from the description.

The subject of the present invention is also a method of avian vaccination comprising the administration of a recombinant live vaccine or of a multivalent vaccine formula as defined above. Its subject is in particular such a method for the vaccination in ovo of one-day-old or older chicks and of adults. Various routes of administration of the vaccine may be used (see above) with a preference for the routes allowing mass vaccination by the mucosal route (aerosol, drinking water), the dose of vaccine being chosen preferably between $10^1$ and $10^4$ per animal.

The subject of the present invention is also an ILTV comprising at least one heterologous nucleotide sequence as described above, inserted into the insertion locus as defined above.

The subject of the present invention is also all or part of the sequence SEQ ID No:1. Part of the sequence is understood to mean not only the characterized ORFs taken separately and fragments thereof, but also the intergenic region situated between ORFs D and E, and the fragments situated on each side of this intergenic region, which may, where appropriate, include part of this intergenic region, it being possible for these fragments to serve as flanking arm for a homologous recombination, a technique perfectly known to persons skilled in the art. In general, but with no limitation being implied, the flanking arms may have from 100 to 1500 base pairs.

The invention will now be described in greater detail by means of the non-limiting exemplary embodiments, taken with reference to the drawing, in which:

EXAMPLES

All the constructions of plasmids were carried out using the standard molecular biology techniques described by Sambrook J. et al. (*Molecular Cloning: A Laboratory Manual.* 2nd Edition. Cold Spring Harbor Laboratory, Cold Spring Harbor, N.Y. 1989). All the restriction fragments used for the present invention were isolated using the "Geneclean" kit (BIO101 Inc. La Jolla, Calif.).

The virus used as parent virus may be chosen from the vaccinal strains described in J. R. Andreasen et al. (*Avian Diseases* 1990. 34. 646–656) or the strain T-20 12-8-66 vaccine LT BLEN obtained from Select laboratories 10026 Main Street P.O. Box 6 Berlin, Md. 21811, USA. It is also possible to use virulent strains such as the Lutticken strain (see above), the strain N-71851 (ATCC VR-783) or the strain 83-2 from USDA, which may be attenuated by known techniques, for example that described in WO-A-95/08622.

Example 1

Culture of the ILTV

The ILTV (strain T20 from Select Laboratories) is cultured on primary chicken kidney cells (CKC); these cells are cultured in MEM medium supplemented with 3% foetal calf serum (FCS) in 75 cm$^2$ culture flasks (2×10$^5$ cells/cm$^2$) one or two days before inoculation.

On the day of inoculation, a flask of 1000 doses of freeze-dried vaccine is resuspended in 10 ml of MEM medium supplemented with 1% FCS; about 0.5 ml of this solution is then deposited on the CKC culture. On the next day, the medium is changed, and the day after, when the cytopathogenic effect (CPE) becomes generalized, the culture flasks are frozen at −70° C.

The culture of the ILTV can also be carried out on immortalized chicken liver cells, and in particular on the LMH line (W. M. Schnitzlein et al., *Avian Diseases* 1994. 38. 211–217).

Example 2

Preparation of the ILTV Genomic DNA

After 2 freeze/thaw cycles, the ILTV culture (2 flasks of 75 cm$^2$) is harvested and centrifuged at low speed (5000 rpm in a 20 rotor, Beckman JA21 centrifuge, for 5 minutes) to remove the large cell debris. The supernatant is then ultracentrifuged (100,000 rpm, TLA100.3 rotor, Beckman TL100 centrifuge, for 1 hour). The pellet is then taken up in 1.6 ml of TEN-SDS (10 mM Tris pH 8.0; 1 mM EDTA; 0.5 M NaCl; 0.5% sodium dodecyl sulphate), and 35 µl of a proteinase K solution at 20 mg/ml are then added; the solution is incubated for 3 to 4 hours on a water bath at 37° C., and the DNA is then extracted 3 times with phenol/chloroform and once with chloroform, then it is precipitated with ethanol at −20° C. After centrifugation, the pellet is rinsed with 70% ethanol, dried and resuspended in 200 µl of TE (10 mM Tris pH 8.0; 1 mM EDTA). The nucleic acid concentration is then assayed in a spectrophotometer (OD$_{260}$). The DNA can be directly digested with the appropriate restriction enzymes so that it can then be cloned into the plasmid pBlue Script II SK$^+$; likewise, it can also be used in the transfection experiments for obtaining a recombinant virus.

Example 3

Isolation and Purification of the Recombinant ILTV

The donor plasmid composed of a cassette for expressing a polypeptide inserted between two flanking regions of the insertion locus is digested with a restriction enzyme allowing the linearization of the plasmid, then it is extracted with a phenol/chloroform mixture, precipitated with absolute ethanol, and taken up in sterile water. 24-Hour primary CKC cells are then transfected with the following mixture: 0.2 to 1 µg of linearized donor plasmid +2 to 5 µg of ILTV viral DNA (prepared as in Example 2) in 300 µl of OptiMEM (Gibco BRL Cat#041-01985H) and 100 µg of LipofectAMINE diluted in 300 µl of medium (final volume of the mixture =600 µl). These 600 µl are then diluted in 3 ml (final volume) of medium and plated on 5×10$^6$ CKC. The mixture is left in contact with the cells for 5 hours, then removed and replaced with 5 ml of culture medium. The cells are then left in culture for 3 to 8 days at +37° C., then, when the cytopathogenic effect has appeared, they are frozen at −70° C. After thawing and optionally sonicating, this viral population is cloned at limiting dilution in microplates (96 well) in order to isolate a homogeneous recombinant virus population. These plates are left in culture for 1 to 3 days, then the supernatant is harvested in an empty 96-well plate and the plate containing the supernatants is placed at 4° C. or at −70° C. The cells remaining in the other plates are then fixed with 95% acetone for 20 to 30 minutes at −20° C., or for 5 minutes at room temperature. An indirect immunofluorescence (IIF) reaction is carried out with a monoclonal antibody directed against the polypeptide expressed in order to seek out the plaques expressing this polypeptide. Another cloning is then carried out in the same manner (at limiting dilution in 96-well plates) from the supernatant present in the wells of the plates placed at 4° C. or at −70° C. and corresponding to the wells having positive plaques in IIF. In general, 4 successive isolation cycles (limiting dilution, harvesting of the supernatant, monitoring of the cells by IIF, limiting dilution from the supernatant and the like) are sufficient to obtain recombinant viruses whose entire progeny exhibits a specific fluorescence. The genomic DNA of these recombinant viruses is characterized at the molecular level by conventional PCR and Southern blotting techniques using the appropriate oligonucleotides and DNA probes.

The isolation of the recombinant virus may also be carried out by hybridization with a probe specific for the inserted expression cassette. For that, the viral population harvested after transfection is diluted and deposited on CKC cells (cultured in a Petri dish) so as to obtain isolated plaques. After 1 hour of contact at 37° C., the infection medium is removed and replaced with 5 ml of MEM medium containing 1% agarose, maintained superfused at 42° C. When the agarose has solidified, the dishes are incubated for 48 to 72 hours at 37° C. in a CO$_2$ incubator until plaques appear. The agarose layer is then removed and the viral plaques are transferred onto a sterile nitrocellulose membrane having the same diameter as the Petri dish which served for the culture. This membrane is itself transferred onto another nitrocellulose membrane so as to obtain a reverse "copy" of the first transfer. The plaques transferred onto this latter copy are then hybridized, according to the customary techniques known to persons skilled in the art, with a digoxigenin-labelled DNA fragment of the expression cassette (DNA Labelling Kit, Boehringer Mannheim, CAT #1175033). After hybridization, washes and contacting with the revealing substrate, the nitrocellulose membrane is placed in contact with an autoradiographic film. The images of positive hybridization on this membrane indicate the plaques which contain the recombinant ILTVs which have inserted the expression cassette. The plaques corresponding to these positive plaques are sterilely cut out from the first nitrocellulose membrane, placed in an Eppendorf tube containing 0.5 ml of MEM medium and sonicated to release the virions from the membrane. The medium contained in the Eppendorf tube is then diluted in MEM medium and the dilutions thus obtained serve to infect new cultures of CKC cells.

Example 4

Cloning and Characterization of an ILTV Genomic Region

The DNA extracted from the ILTV virus was digested with the restriction enzyme EcoRI for 2 hours at 37° C. The restriction enzyme was then removed by extraction with phenol/chloroform, followed by precipitation with ethanol.

The fragments resulting from this digestion were then ligated (overnight at 14° C.) with the plasmid pBlueScriptII SK+(pBS SK+; Stratagene) digested with EcoRI and treated with alkaline phosphatase; the analysis of the clones obtained after transformation of E. coli DH5α bacteria and culture on dishes of ampicillin-supplemented medium made it possible to identify EcoRI—EcoRI inserts of different sizes, including a fragment of about 7 kb (plasmid pEL133).

Complete sequencing of the insert present in pEL133 (see FIG. 1) made it possible to identify five complete open reading frames (ORFs) of at least 120 amino acids (ORFs A, B, C, D and E), and part of another ORF (ORF F). The restriction map of this cloned and sequenced genomic region is shown in FIG. 1; the 7082 bp sequence (SEQ ID NO:1) is shown in FIG. 2. The position and the amino acid sequence of the ORFs A, B, C, D, E and F are also shown in FIGS. 1 and 2 respectively.

The sequence between the STOP codons of the ORFs D and E (position from 3873 to 4260 on SEQ ID NO: 1) can be used to insert cassettes for expressing polypeptides into the ILTV genome. This sequence is called insertion locus. The insertion may be made with or without deletion in the intergenic region (see Example 5).

Example 5

Construction of the Donor Plasmid pEL168 for Insertion into the Intergenic Region Between the ORFs D and E The plasmid pBlueScript II SK+ (pPB SK+; Stratagene) was digested with the enzymes XhoI and HindII, and then treated with DNA polymerase (Klenow fragment) in the presence of dNTP in order to make the ends blunt. After ligation and transformation of E. coli bacteria, the clone pEL166 (2957 bp) was obtained.

The plasmid pEL166 was digested with the enzymes ScaII and XbaI and then treated with DNA polymerase (Klenow fragment) in the presence of dNTP in order to make the ends blunt. After ligation and transformation of the E. coli bacteria, the clone pEL167 (2944 bp) was obtained.

The oligonucleotides EL005 (SEQ ID NO:13) and EL006 (SEQ ID NO:14) served as primer for a first polymerase chain reaction with Taq polymerase (PCR). The oligonucleotides EL007 (SEQ ID NO:15) and EL008 (SEQ ID NO:16) served as primer for a second polymerase chain reaction with Taq polymerase (PCR).

EL005 (SEQ ID NO:13): 5' TGCCGGAGCGCAACCG-CATGG 3'

EL006 (SEQ ID NO: 14): 5' GACACCGAATTCG-TAAGCTTTCCCCGGGCAGTCGA-CAACGTGGAGCATTTTTATTTATC 3'

EL007 (SEQ ID NO:15): 5' GTGTTATCTCTCTAGCAT-TGGC 3'

EL008 (SEQ ID NO:16): 5' AGTTCTGAATTCGTGTC-CGTTGTATTGTATTC 3'

The PCRs were carried out in the presence of PCR buffer, dNTP, DNA from the plasmid pEL133, Taq polymerase, and for the first PCR, EL005 and EL006 oligonucleotides, and for the second PCR, EL007 and EL008 oligonucleotides.

For the two PCRs, 25 cycles were performed (30 seconds at 94° C.; 30 seconds at 60° C. and 30 seconds at 72° C.). The products of the two PCRs were purified by phenol/chloroform extraction, followed by purification using ethanol. The product of the first PCR (EL005/EL006) was then digested with the restriction enzymes BstBI and EcoRI for 2 h at 37° C. to give a 1132 bp BstBI-EcoRI DNA fragment which was eluted after agarose gel electrophoresis. The product of the second PCR (EL007/EL008) was then digested with the restriction enzymes BglII and EcoRI for 2 h at 37° C. to give a 550 bp BglII-EcoRI DNA fragment which was eluted after agarose gel electrophoresis. The plasmid pEL167 was digested with the enzymes ClaI and BamHI. The two PCR fragments BstBI-EcoRI (1132 bp) and BglII-EcoRI (550 bp) were ligated overnight at 14° C. with the plasmid pEL167 digested with ClaI and BamHI. After transformation of the E. coli bacteria and culture on dishes of medium supplemented with ampicillin, the clone pEL168 (4589 bp), comprising a polylinker EcoRI—HindIII—SmaI—SalI was obtained (see scheme for obtaining pEL168 in FIG. 3).

Example 6

Construction of the Donor Plasmid pEL169 for the Insertion of a Cassette for Expressing the IBDV VP2 Gene Under the Control of the HCMV IE Promoter into the Intergenic Site Between the ORFs D and E, and Isolation of vILTV 13

Figure 4:
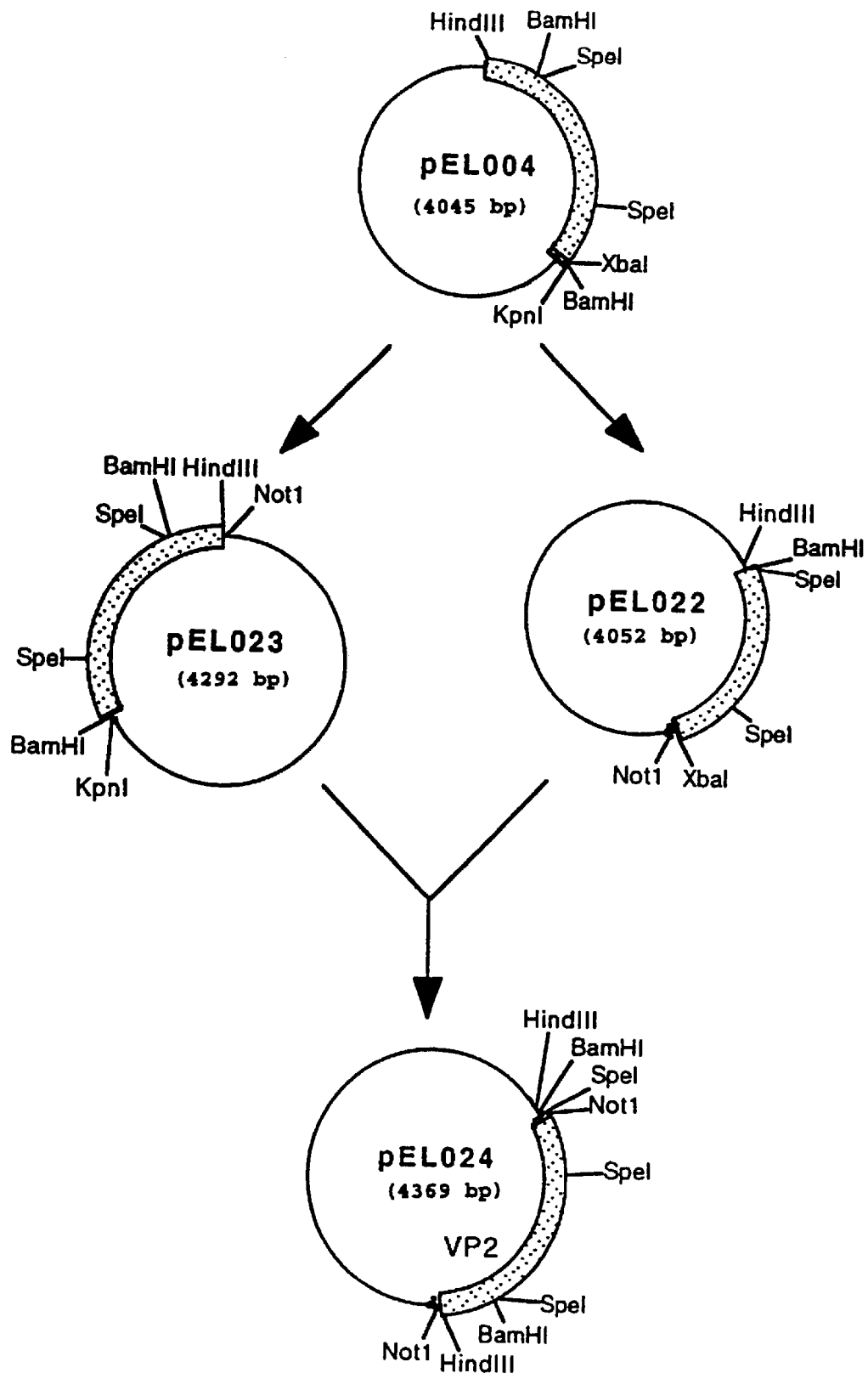
FIG. 4 shows the scheme for obtaining plasmid pEL024.

6.1—Cloning of the VP2 Gene From the Infectious Bursal Disease Virus (IBDV) and Construction of a Cassette for Expressing VP2 Under the Control of the HCMV IE Promoter The plasmid pEL004 (see FIG. 6; =plasmid pGH004 described in French patent application 92,13109) containing the IBDV VP2 gene in the form of a BamHI-HindIII cassette was digested with BamHI and XbaI in order to isolate the BamHI-XbaI fragment (truncated VP2 gene) of 1104 bp. This fragment was cloned into the vector pBS SK+, previously digested with XbaI and BamHI to give the 4052 bp plasmid pEL022 (FIG. 4). The vector pBS-SK+ was digested with EcoRV and XbaI, then self-ligated to give pBS-SK* (modified). The plasmid pEL004 was digested with KpnI and HindIII in order to isolate the 1387 bp KpnI-HindIII fragment containing the complete IBDV VP2 gene. This fragment was cloned into the vector pBS-SK*, previously digested with KpnI and HindIII, to give the 4292 bp plasmid pEL023 (FIG. 4). The plasmid pEL022 was digested with BamHI and NotI in order to isolate the 1122 bp BamHI-NotI fragment (fragment A). The plasmid pEL023 was digested with BamHI and NotI in order to isolate the 333 bp BamHI-NotI fragment (fragment B). The fragments A and B were ligated together with the vector pBS-SK+, previously digested with NotI and treated with alkaline phosphatase, to give the 4369 bp plasmid pEL024 (FIG. 4).

Figure 5:
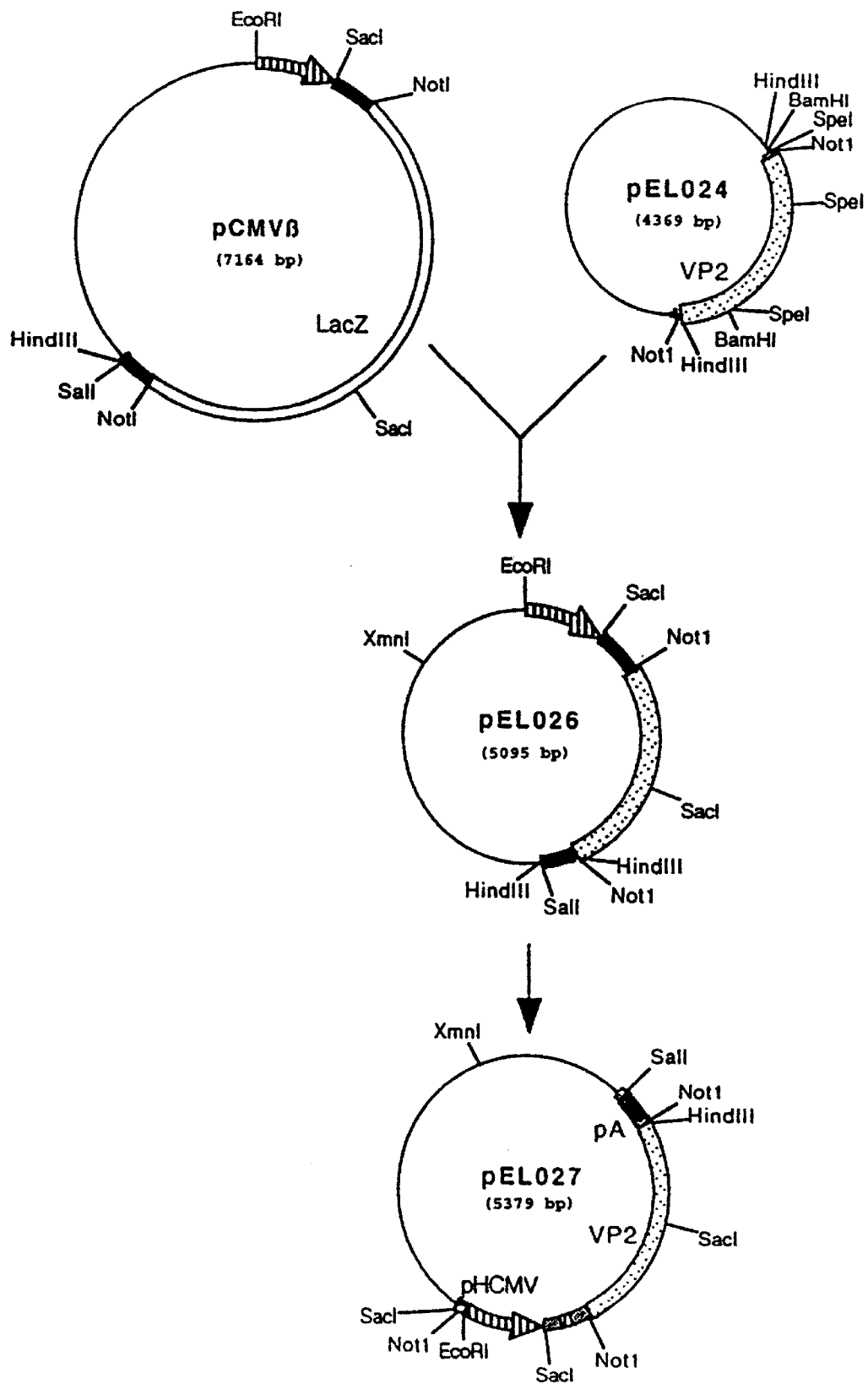
FIG. 5 shows the scheme for obtaining plasmid pEL027.

The plasmid pEL024 was digested with NotI in order to isolate the 1445 bp NotI-NotI fragment. This fragment was ligated with the plasmid pCMVβ (Clontech Cat#6177-1, FIG. 5), previously digested with NotI, to give the 5095 bp plasmid pEL026 (FIG. 5).

The plasmid pEL026 was digested with EcoRI, SalI and XmnI in order to isolate the 2428 bp EcoRI-SalI fragment. This fragment was ligated with the vector pBP-SK+, previously digested with EcoRI and SalI, to give the 5379 bp plasmid pEL027 (FIG. 5).

6.2—Construction of the donor plasmid pEL169

Figure 6:
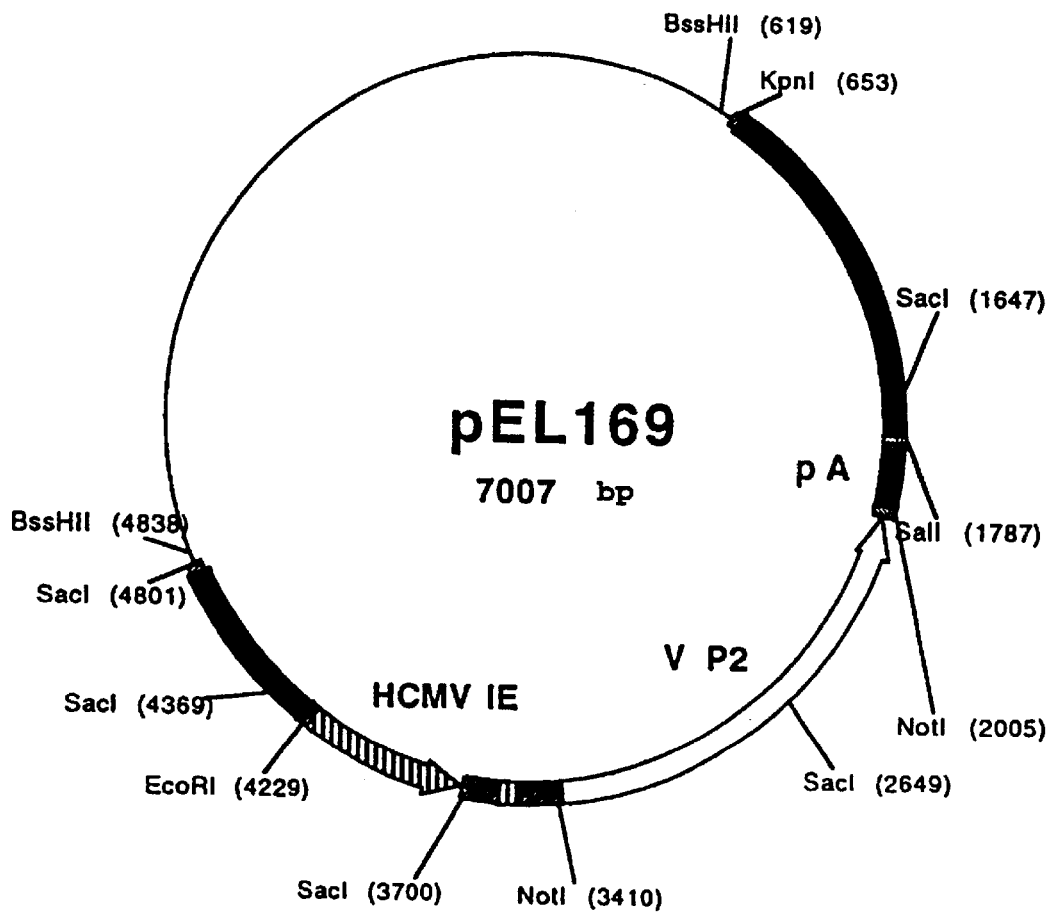
FIG. 6 shows a diagram of plasmid pEL169.

The plasmid pEL027 was digested with EcoRI, SalI and XmnI in order to isolate the 2428 bp EcoRI-SalI fragment. This fragment was ligated into the plasmid pEL168 (see Example 5 and FIG. 3), previously digested with EcoRI and SalI, to give the 7007 bp plasmid pEL169 (FIG. 6).

6.3—Isolation and Purification of the Recombinant vILTV13 Virus

The vILTV13 virus was isolated and purified after cotransfection of the DNA from the plasmid pEL169 previously linearized with the enzyme KpnI, and of the viral DNA, as described in Example 3. This recombinant contains a cassette HCMV-IE/IBDV VP2 in the intergenic site between the ORFs D and E of the ILTV virus (see Example 5).

Example 7

Construction of the Donor Plasmid pEL170 for the Insertion of a Cassette for Expressing the IBDV VP2 Gene Under the Control of the MCMV IE Promoter into the Intergenic Site Between the ORFs D and E and Isolation of vILTV14

Figure 7:
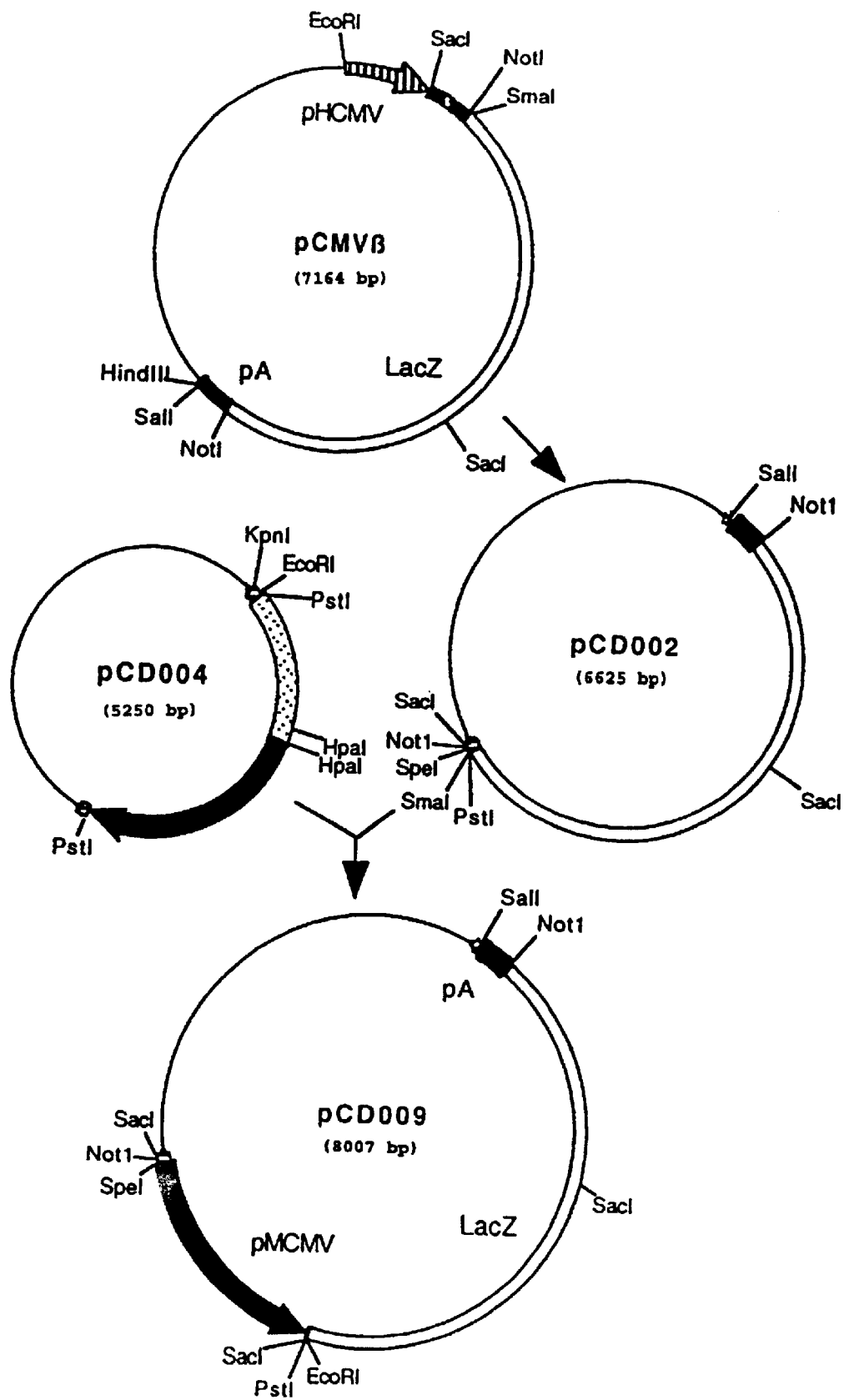
FIG. 7 shows the scheme for obtaining plasmid pCD009.

7.1—Construction of pEL070 Containing a Cassette for Expressing the IBDV VP2 Gene Under the Control of the MCMV (Mouse CytoMegaloVirus) Immediate Early (IE) Promoter The plasmid pCMVβ (Clontech Cat#6177-1, FIG. 7) was digested with SalI and SmaI in order to isolate the 3679 bp SalI-SmaI fragment containing the lacZ gene as well as the polyadenylation signal of the SV40 virus late gene. This fragment was inserted into the vector pBS-SK+, previously digested with SalI and EcoRV, to give the 6625 bp plasmid pCD002 (FIG. 7). This plasmid contains the lacZ reporter gene but no promoter is situated upstream of this gene.

The MCMV virus, Smith strain was obtained from the American Type Culture Collection, Rockville, Md., USA (ATCC No. VR-194). This virus was cultured on Balb/C mouse embryo cells and the viral DNA from this virus was prepared as described by Ebeling A. et al. (J. Virol. 1983. 47. 421–433). This viral genomic DNA was digested with PstI in order to isolate the 2285 bp PstI-PstI fragment. This fragment was cloned into the vector pBS-SK+, previously digested with PstI and treated with alkaline phosphatase, to give the plasmid pCD004 (FIG. 7). The plasmid pCD004 was digested with HpaI and PstI in order to isolate the 1389 bp HpaI-PstI fragment which contains the promoter/activating region of the murine cytomegalovirus Immediate-Early gene (Murine CytoMegaloVirus =MCMV) (Dorsch-Häsler K. et al. Proc. Natl. Acad. Sci. USA 1985. 82. 8325–8329, and patent application WO-A-87/03905). This fragment was cloned into the plasmid pCD002, previously digested with PstI and SmaI, to give the 8007 bp plasmid pCD009 (FIG. 7).

A double-stranded oligonucleotide was obtained by hybridization of the following two oligonucleotides:
MB070 (SEQ ID NO:17) 5' CGAATTCACTAGTGTGT-GTCTGCAGGCGGCCGCGTGTGTGTCGACGGTAC 3'
MB071 (SEQ ID NO:18) 5' CGTCGACACACACGCGGC-CGCCTGCAGACACACACTAGTGAATTCGAGCT 3'

Figure 8:
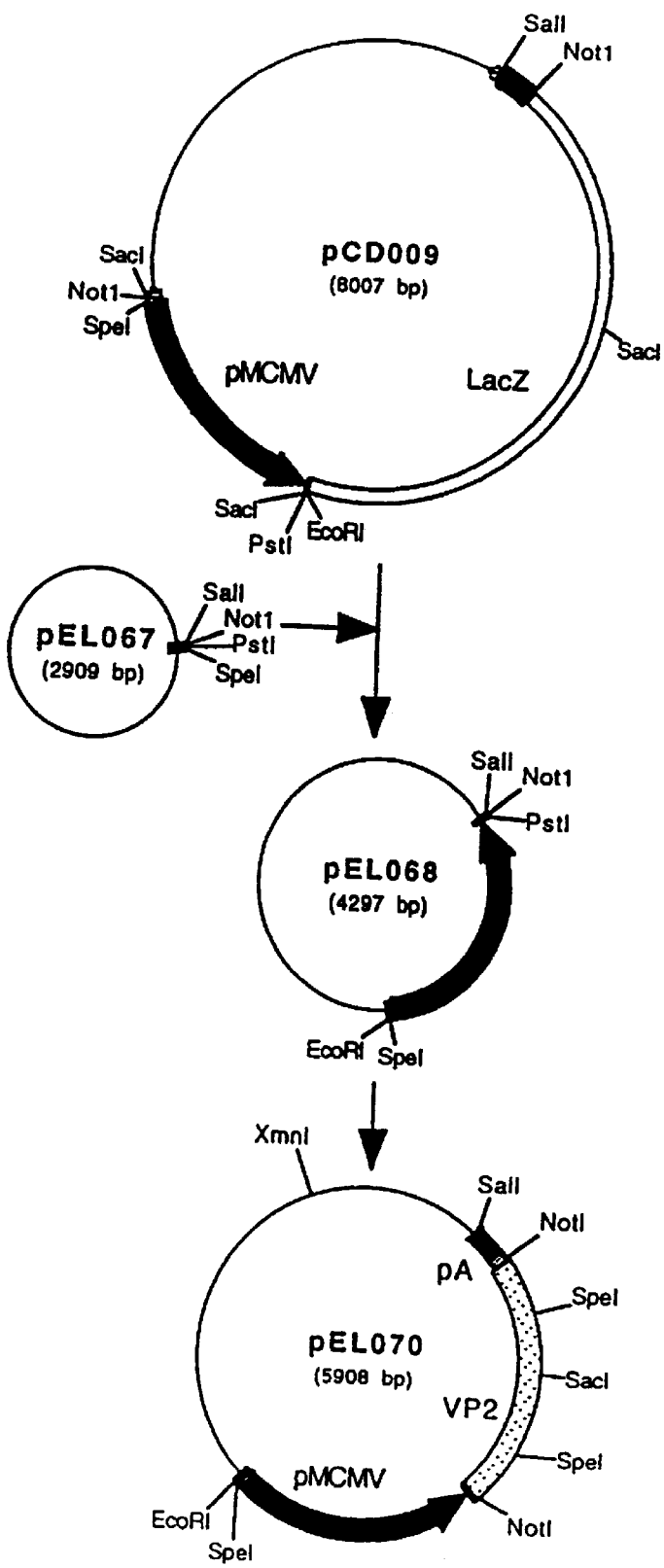
FIG. 8 shows the scheme for obtaining plasmid pEL070.

This double-stranded oligonucleotide was ligated with the vector pBS-SK+, previously digested with KpnI and SacI, to give the plasmid pEL067 (FIG. 8). The plasmid pCD009 was digested with PstI and SpeI in order to isolate the 1396 bp PstI-SpeI fragment. This fragment was ligated with the plasmid pEL067, previously digested with PstI and SpeI, to give the 4297 bp plasmid pEL068 (FIG. 8). The plasmid pEL024 (see Example 6, paragraph 6.1 and FIG. 5) was digested with HindIII and NotI in order to isolate the 1390 bp HindIII-NotI fragment (fragment A). The plasmid pEL027 (see Example 6, paragraph 6.1 and FIG. 5) was digested with HindIII and SalI in order to isolate the 235 bp HindIII-SalI fragment (fragment B). The fragments A and B were ligated together with the plasmid pEL068, previously digested with NotI and SalI, in order to give the 5908 bp plasmid pEL070 (FIG. 8). This plasmid therefore contains an expression cassette consisting of the MCMV IE promoter, the VP2 gene and the SV40 polyA signal.

7.2—Construction of the Donor Plasmid pEL170

Figure 9:
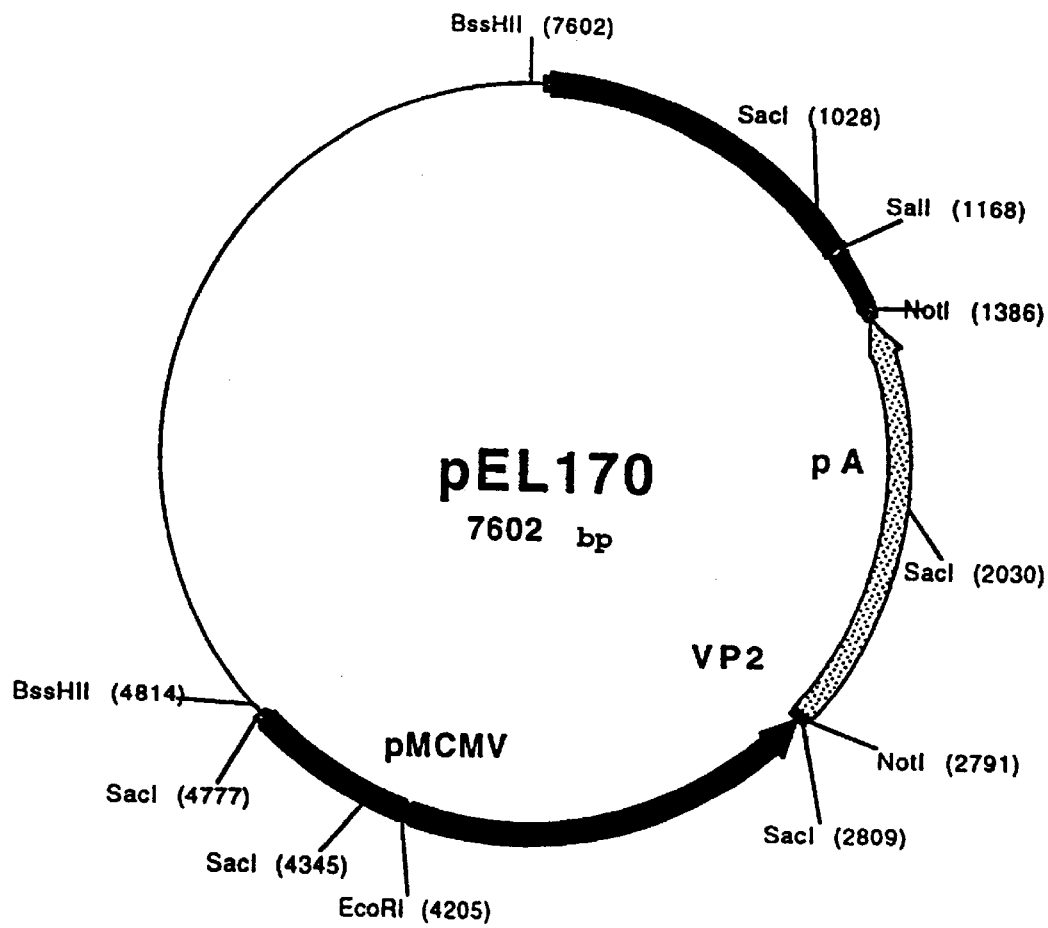
FIG. 9 shows a diagram of plasmid pEL070.

The plasmid pEL070 was digested with EcoRI, SalI and XmnI in order to isolate the 3035 bp EcoRI-SalI fragment. This fragment was ligated into the plasmid pEL168 (see Example 5 and FIG. 3), previously digested with EcoRI and SalI, in order to give the 7602 bp plasmid pEL170 (FIG. 9). This plasmid allows the insertion of the expression cassette MCMV-IE/IBDV-VP2 into the intergenic site between the ORFs D and E of the ILTV.

7.3—Isolation and Purification of the vILTV14 Recombinant Virus

The vILTV14 virus was isolated and purified after cotransfection of the DNA from the plasmid pEL170 previously linearized with the enzyme BssHII and of the viral DNA, as described in Example 3. This recombinant contains a cassette MCMV-IE/IBDV VP2 in the intergenic site between the ORFs D and E of the ILTV (see Example 5).

Example 8

Construction of the Donor Plasmid pEL171 for the Insertion of a Cassette for Expressing the NDV HN Gene into the Intergenic Site Between the ORFs D and E and Isolation of vILTV15

8.1—Cloning of the Newcastle disease virus (NDV) HN gene

Figure 11:
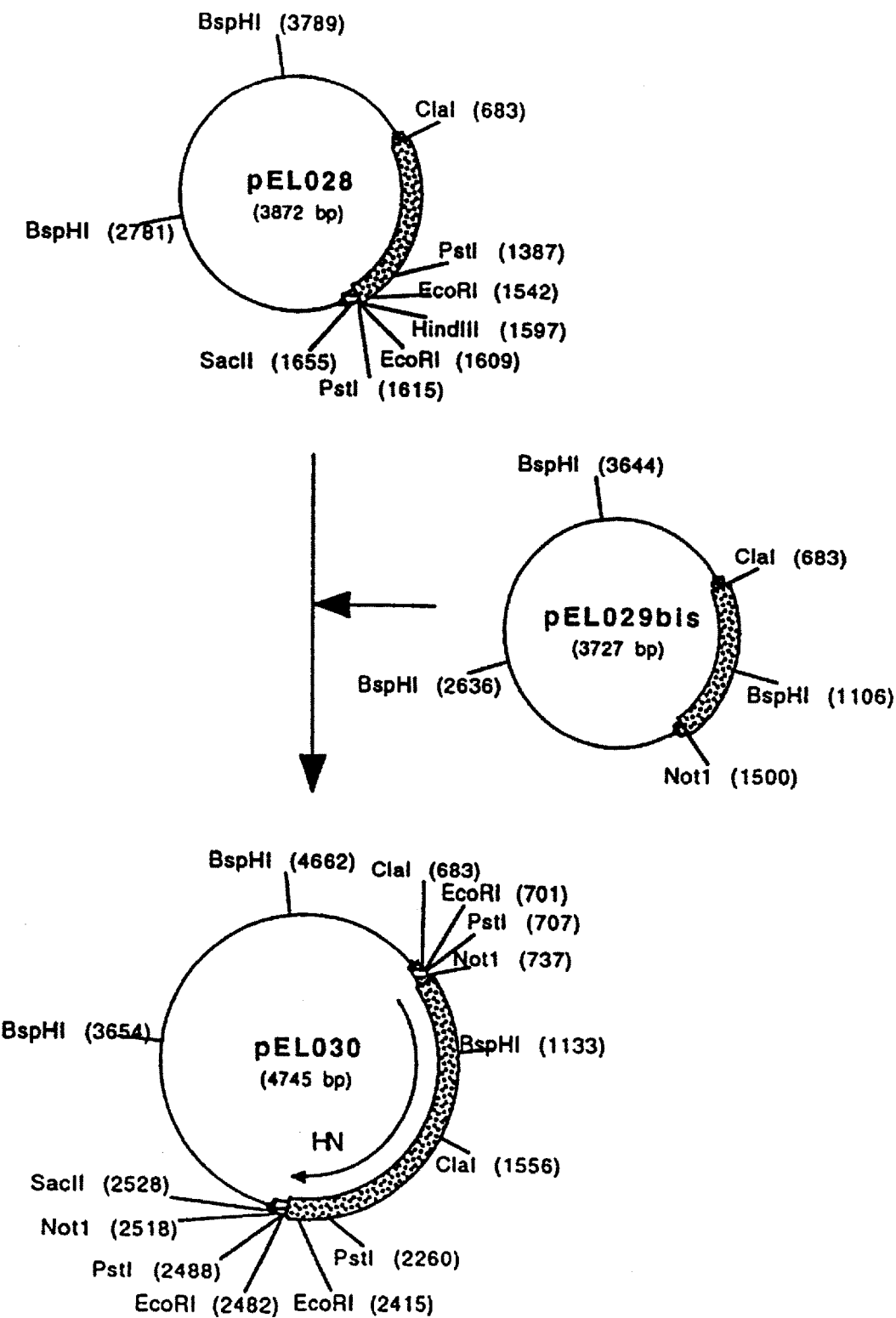
FIG. 11 shows the scheme for obtaining plasmid pEL030.

The constitution of a DNA library complementary to the genome of the Newcastle disease virus (NDV), Texas strain, was made as described by Taylor J. et al. (J. Virol. 1990. 64. 1441–1450). A clone pBR322 containing the end of the fusion gene (F), the entire haemagglutinine-euraminidase (HN) gene and the beginning of the polymerase gene was identified as pHN01. The sequence of the NDV HN gene contained on this clone is presented in FIG. 10 (SEQ ID NO:8). The plasmid pHN01 was digested with SphI and XbaI in order to isolate the 2520 bp SphI-XbaI fragment. This fragment was ligated with the vector pUC19, previously digested with SphI and XbaI, in order to give the 5192 bp plasmid pHN02. The plasmid pHN02 was digested with ClaI and PstI in order to isolate the 700 bp ClaI-PstI fragment (fragment A). A PCR was carried out with the following oligonucleotides:
EL071 (SEQ ID NO:19) 5' CAGACCAAGCTTCT-TAAATCCC 3'
EL073 (SEQ ID NO:20) 5' GTATTCGGGACAATGC 3'
and the template pHN02 in order to produce a 270 bp PCR fragment. This fragment was digested with HindIII and PstI in order to isolate a 220 bp HindIII-PstI fragment (fragment B). The fragments A and B were ligated together with the vector pBS-SK+, previously digested with ClaI and HindIII, in order to give the 3872 bp plasmid pEL028 (FIG. 11). The plasmid pHN02 was digested with BsphI and ClaI in order to isolate the 425 bp BsphI-ClaI fragment (fragment C). A PCR was carried out with the following oligonucleotides:
EL074 (SEQ ID NO:21) 5' GTGACATCACTAGCGT-CATCC 3'
EL075 (SEQ ID NO:22) 5' CCGCATCATCAGCGGCCGC-GATCGGTCATGGACAGT 3'
and the template pHN02 in order to produce a 465 bp PCR fragment. This fragment was digested with BsphI and NotI in order to isolate the 390 bp BsphI-NotI fragment (fragment D). The fragments C and D were ligated together with the vector pBS-SK+, previously digested with ClaI and NotI, in order to give the 3727 bp plasmid pEL029bis (FIG. 11). The plasmid pEL028 was digested with ClaI and SacII in order to isolate the 960 bp ClaI-SacII fragment (fragment E). The plasmid pEL029bis was digested with ClaI and NotI in order to isolate the 820 bp ClaI-NotI fragment (fragment F). The fragments E and F were ligated together with the vector pBS-SK+, previously digested with NotI and SacII, in order to give the 4745 bp plasmid pEL030 (FIG. 11).

Figure 12:
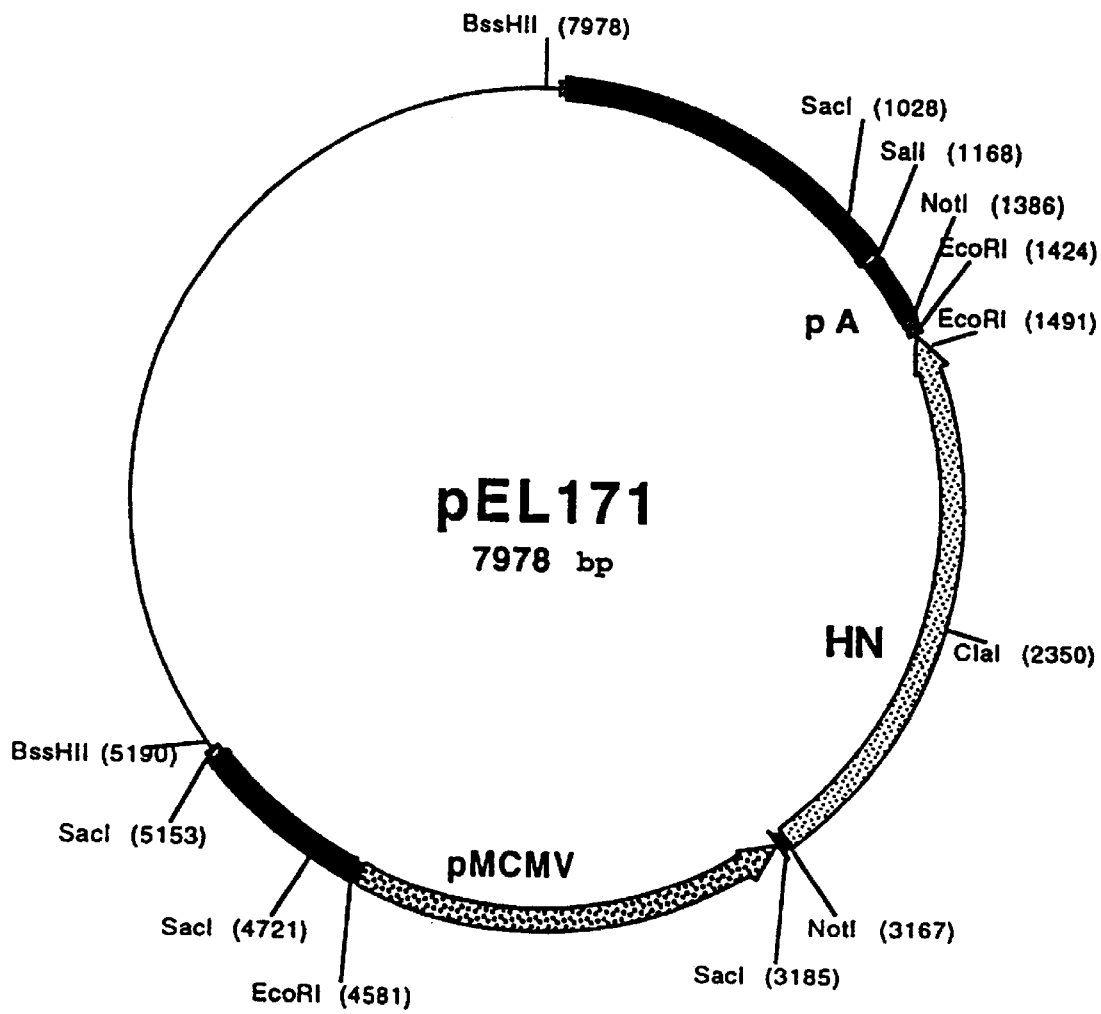
FIG. 12 shows a diagram of plasmid pEL171.

8.2—Construction of the Plasmid pEL171 Containing a Cassette for Expressing NDV HN in the Intergenic Site Between the ORFs D and E The plasmid pEL030 was digested with NotI in order to isolate the 1780 bp NotI-NotI fragment (entire NDV HN gene). This fragment was inserted into the NotI sites of the plasmid pEL170 (Example 7, FIG. 9) in place of the 1405 bp NotI-NotI fragment containing the gene encoding the IBDV VP2 protein; this cloning made it possible to isolate the 7978 bp plasmid pEL171 (FIG. 12). This plasmid allows the insertion of the expression cassette MCMV-IE/NDV-HN into the intergenic site between the ORFs D and E of the ILTV virus.

8.3—Isolation and Purification of the Recombinant Virus vILTV15

The virus vILTV15 was isolated and purified after cotransfection of the DNA from the plasmid pEL171 previously linearized with the enzyme BssHII and of the viral DNA, as described in Example 3. This recombinant contains a cassette MCMV-IE/NDV HN in the intergenic site between the ORFs D and E of the ILTV (see Example 5).

Example 9

Construction of the Donor Plasmid pEL172 for the Insertion of a Cassette for Expressing the NDV F Gene into the Intergenic Site Between the ORFs D and E and Isolation of vILTV16

9.1—Cloning of the Newcastle Disease Virus (NDV) F Gene

Figure 13:
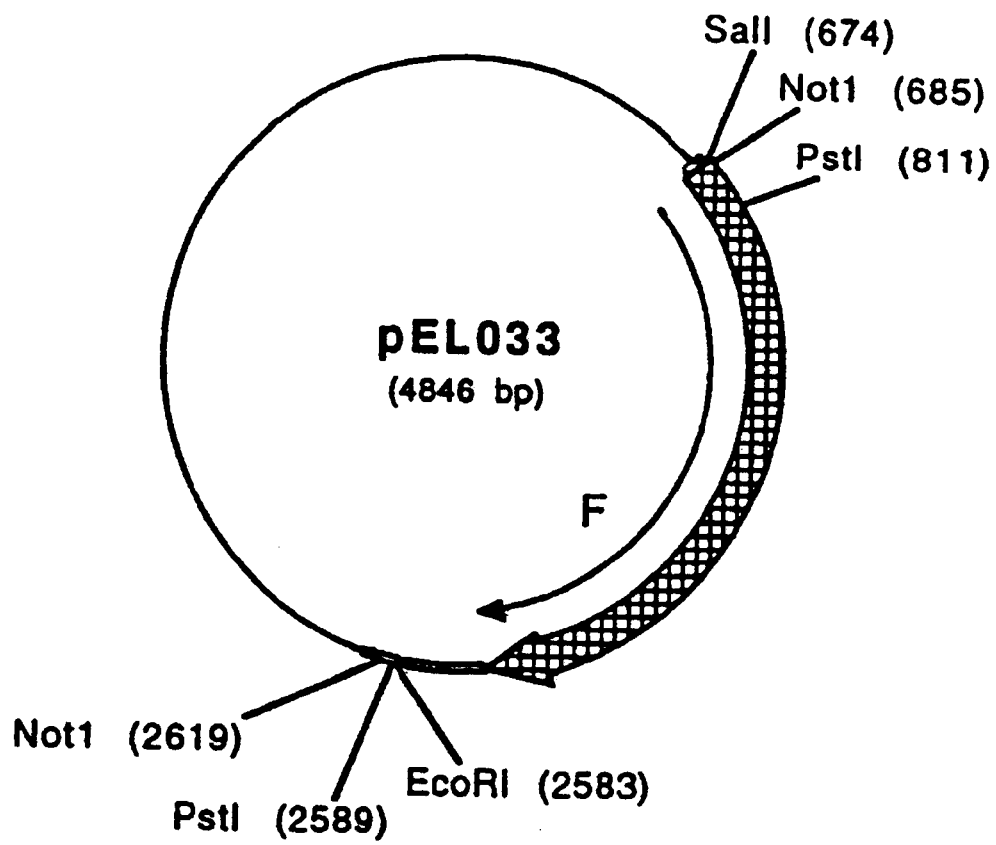
FIG. 13 shows a diagram of plasmid pEL033.

A clone derived from the DNA library complementary to the Newcastle disease virus genome (see Example 8, paragraph 8.1) and containing the entire fusion (F) gene was called pNDV81. This plasmid has been previously described and the sequence of the NDV F gene present on this close has been published (Taylor J. et al J. Virol. 1990. 64. 1441–1450). The plasmid pNDV81 was digested with NarI and PstI in order to isolate the 1870 bp NarI-PstI fragment (fragment A). A PCR was carried out with the following oligonucleotides:
EL076 (SEQ ID NO:23): TGACCCTGTCTGGGATGA 3'
EL077 (SEQ ID NO:24): 5' GGATCCCGGTCGACACAT-TGCGGCCGCAAGATGGGC 3'
and the template pNDV81 in order to produce a 160 bp fragment. This fragment was digested with PstI and SalI in order to isolate the 130 bp PstI-SalI fragment (fragment B). The fragments A and B were ligated together with the vector pBS-SK+, previously digested with ClaI and SalI, in order to give the 4846 bp plasmid pEL033 (FIG. 13).

Figure 14:
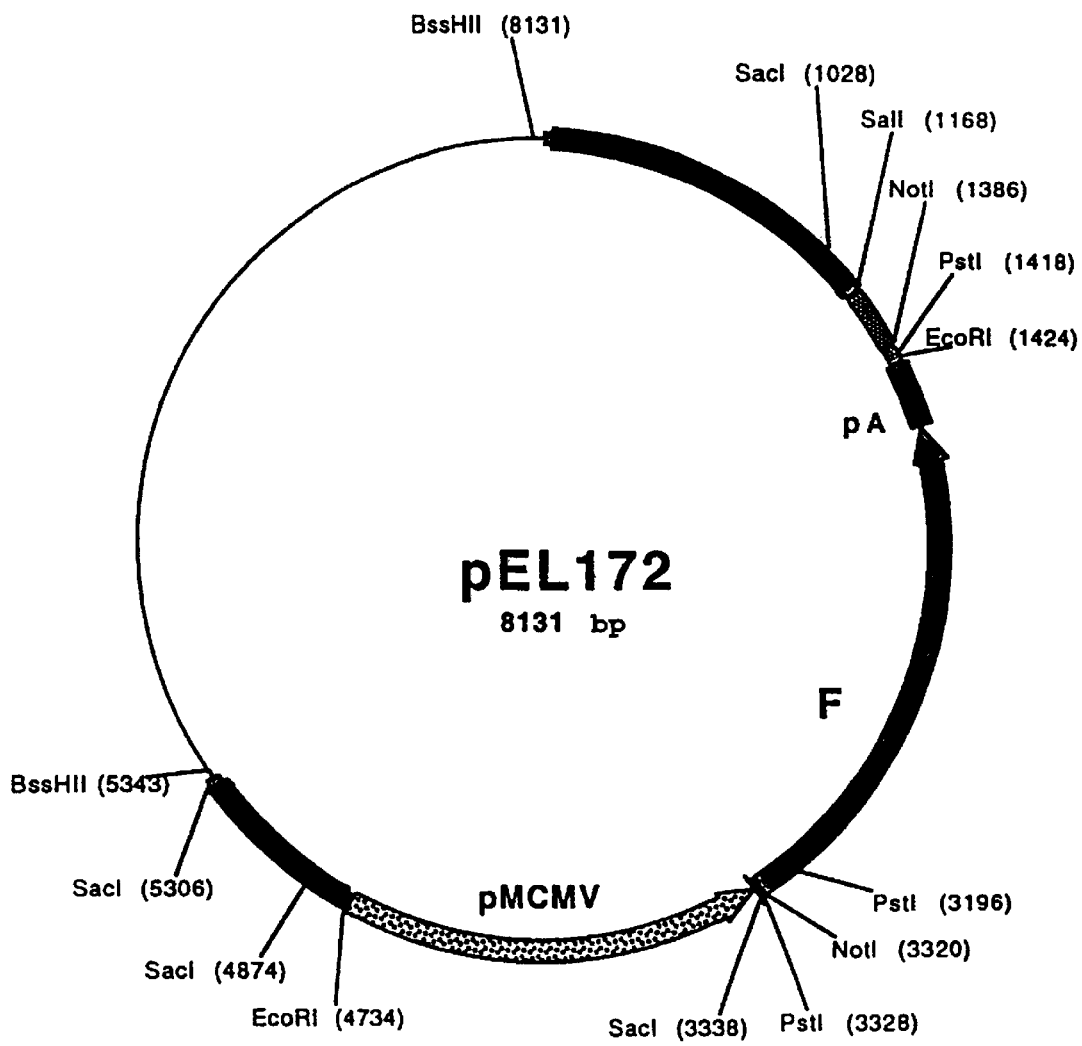
FIG. 14 shows a diagram of plasmid pEL172.

9.2—Construction of the Plasmid pEL172 Containing a Cassette for Expressing the NDV F Gene in the Intergenic Site Between the ORFs D and E The plasmid pEL033 was digested with NotI in order to isolate the 1935 bp NotI-NotI fragment (entire F gene). This fragment was inserted into the NotI sites of the plasmid pEL170 (Example 7, FIG. 9) in place of the 1405 bp NotI-NotI fragment containing the gene encoding the IBDV VP2 protein; this cloning made it possible to isolate the 8131 bp plasmid pEL172 (FIG. 14). This plasmid allows the insertion of the expression cassette MCMV-IE/NDV-F into the intergenic site between the ORFs D and E of the ILTV virus.

9.3—Isolation and Purification of the Recombinant Virus vILTV16

The vILTV16 virus was isolated and purified after cotransfection of the DNA from the plasmid pEL172 previously linearized with the enzyme BssHII and of the viral DNA, as described in Example 3. This recombinant contains a cassette MCMV-IE/NDV F in the intergenic site between the ORFs D and E of the ILTV virus (see Example 5).

Example 10

Figure 15:
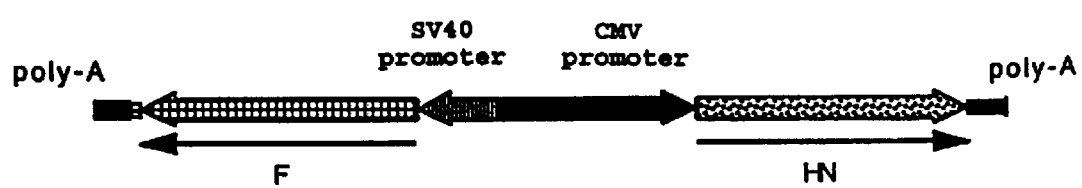
FIG. 15 shows the double expression cassette.

Construction of a Donor Plasmid for the Insertion of a Double Cassette for Expressing the NDV HN and F Genes into the Intergenic Site Between the ORFs D and E and Isolation of a Recombinant ILTV Virus A double cassette for expressing two genes, for example the NDV virus HN and F genes, may be constructed. Such a construct is schematically represented in FIG. 15. In this constuct, the 5' end of the two promoters are adjacent so that the transcription of the two genes occurs in opposite directions. One of the two promoters is preferably a CMV IE promoter and the other promoter (called associated promoter) is the SV40 promoter (present in the pSVbeta plasmid, Clontech Laboratories, Palo Alto, Calif. 94303–4607, USA). In this configuration, the associated promoter is activated by the activating region of the CMV IE promoter.

Figure 3:
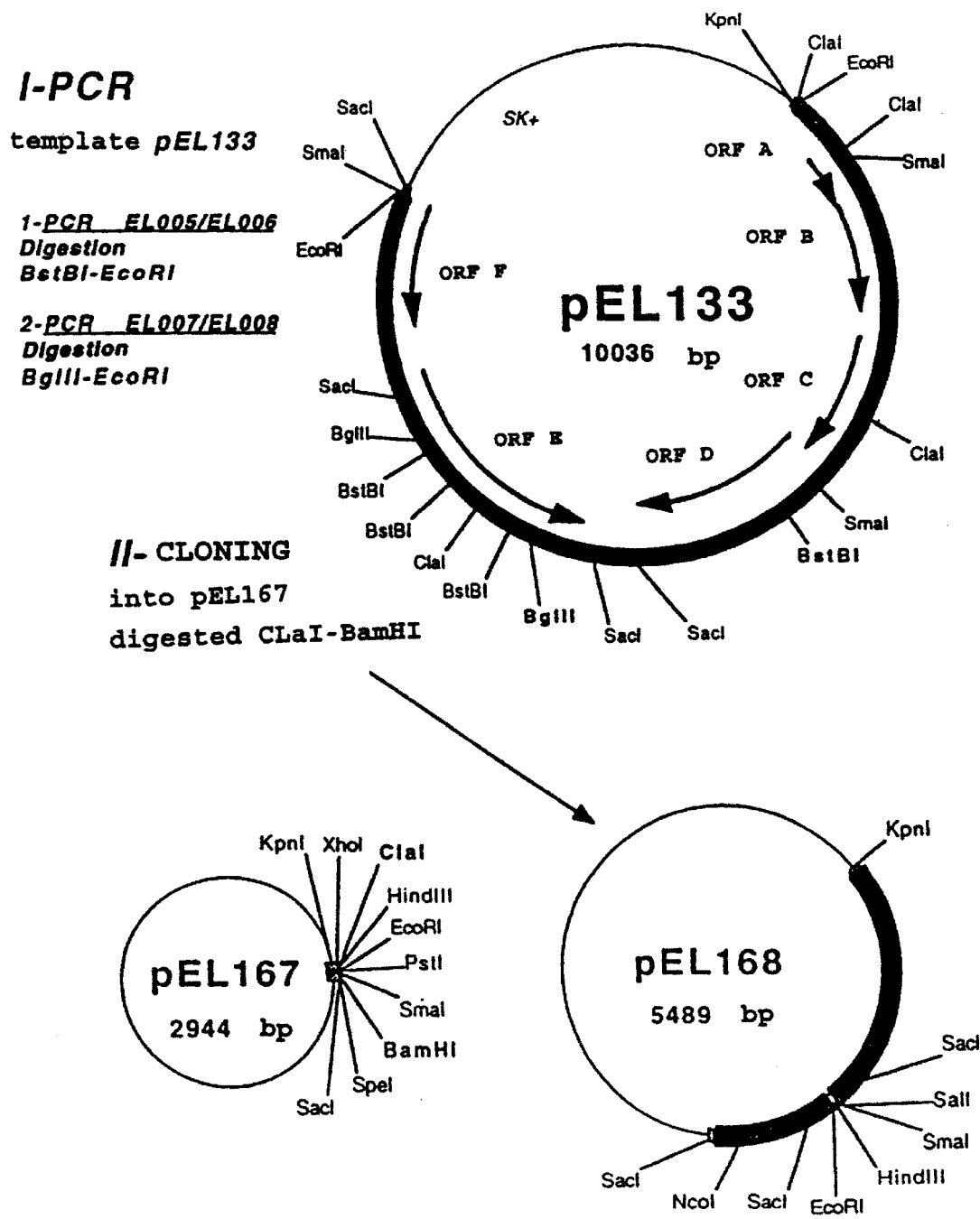
FIG. 3 shows the scheme for obtaining plasmid pEL168.

This double expression cassette may then be inserted into the donor plasmid described above (pEL168 described in Example 5 and represented in FIG. 3). The isolation of the recombinant viruses is carried out in the same manner as above (see Example 3).

Example 11

Construction of the Donor Plasmid pEL181 for the Insertion of a Cassette for Expressing the MDV gB Gene into the Intergenic Site Between the ORFs D and E and Isolation of vILTV17

11.1—Cloning of the Marek's Disease Virus gB Gene

Figure 16:
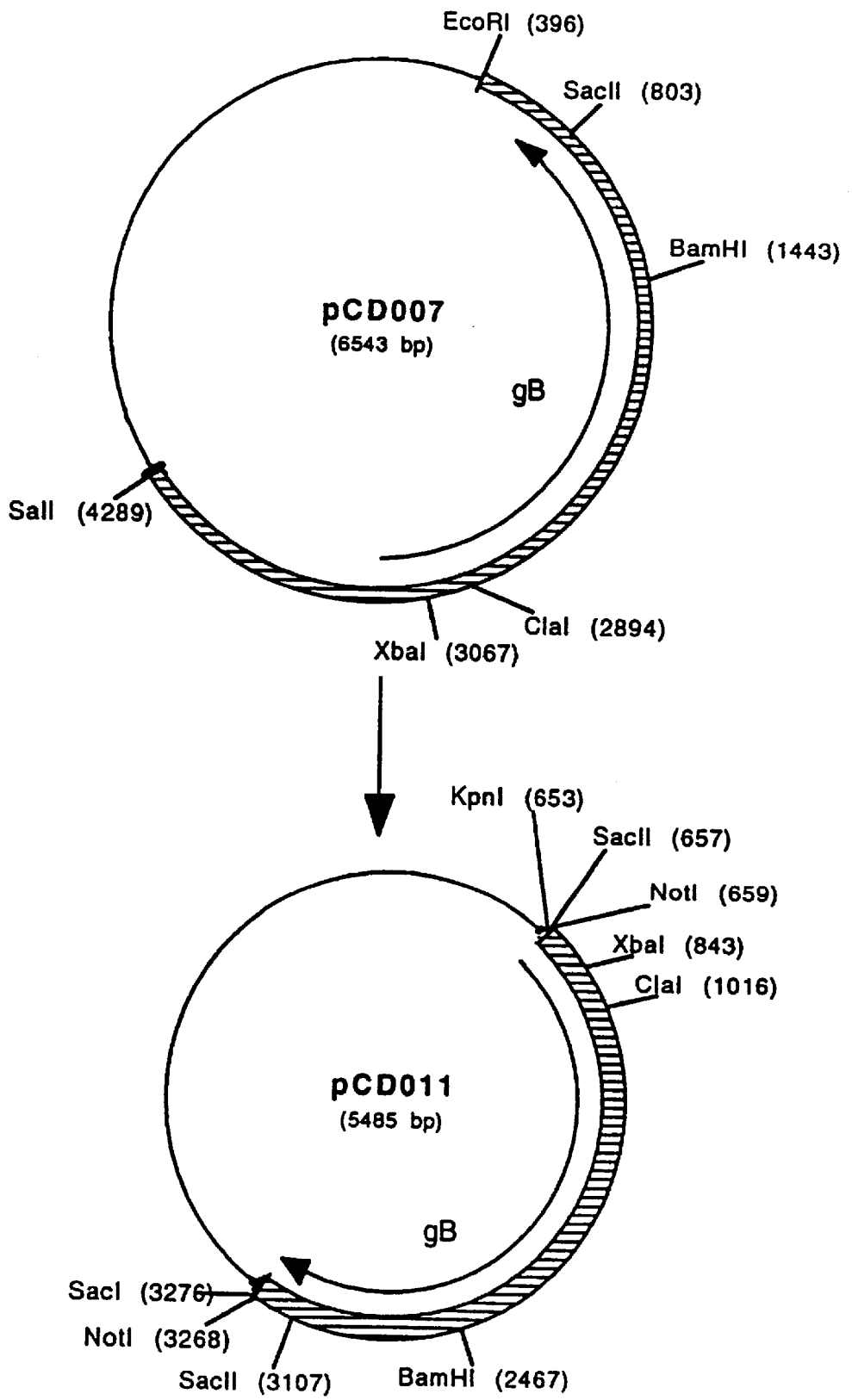
FIG. 16 shows the scheme for obtaining plasmid pCD011.

The 3.9 kbp EcoRI-SalI fragment of the genomic DNA from the MDV virus strain RB1B containing the MDV gB gene (sequence published by Ross N. et al. J. Gen. Virol. 1989. 70. 1789–1804) was ligated with the vector pUC13, previously digested with EcoRI and SalI, in order to give the 6543 bp plasmid pCD007 (FIG. 16). This plasmid was digested with SacI and XbaI in order to isolate the 2260 bp SacI-XbaI fragment (central part of the gB gene=fragment A). A PCR was carried out with the following oligonucleotides:
CD001 (SEQ ID NO:25): 5' GACTGGTACCGCGGCCG-CATGCACTTTTTAGGCGGAATTG 3'
CD002 (SEQ ID NO:26) 5' TTCGGGACATTTTCGCGG 3'
and the template pCD007 in order to produce a 222 bp PCR fragment. This fragment was digested with KpnI and XbaI in order to isolate a 190 bp KpnI-XbaI fragment (5' end of the gB gene=fragment B). Another PCR was carried out with the following oligonucleotides:
CD003 (SEQ ID NO:27): 5' TATATGGCGTTAGTCTCC 3'

CD004 (SEQ ID NO:28) 5' TTGCGAGCTCGCGGC-
CGCTTATTACACAGCATCATCTTCTG 3'
and the template pCD007 in order to produce a 195 bp PCR fragment. This fragment was digested with SacI and SacII in order to isolate the 162 bp SacI-SacII fragment (3' end of the gB gene=fragment C). The fragments A, B and C were ligated together with the vector pBS-SK+, previously digested with KpnI and SacI, in order to give the 5485 bp plasmid pCD011 (FIG. 16).

Figure 17:
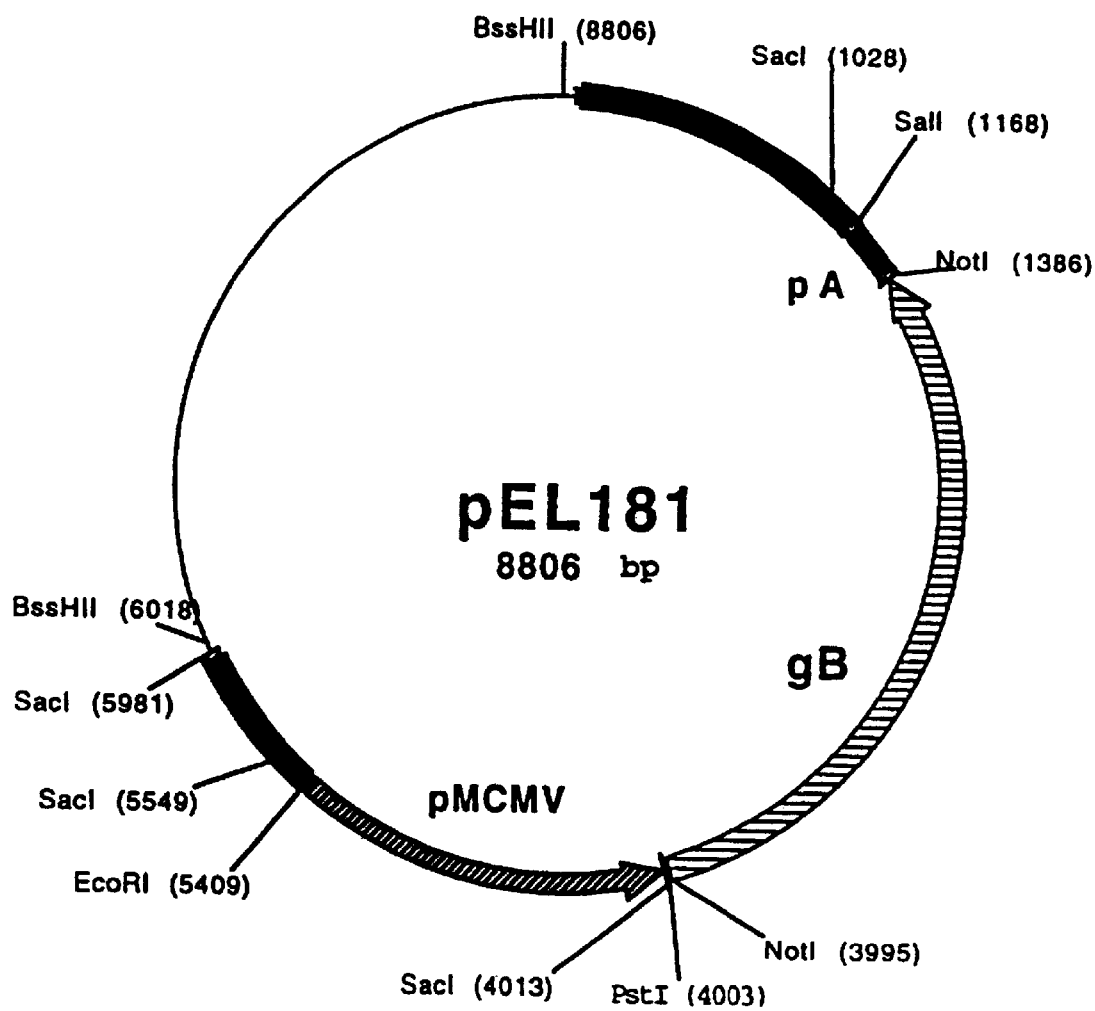
FIG. 17 shows a diagram of plasmid pEL181.

11.2—Construction of the Plasmid pEL181 Containing a Cassette for Expressing the MDV gB Gene in the Intergenic Site Between the ORFs D and E of the ILTV The plasmid pCD011 was digested with NotI in order to isolate the 2608 bp NotI-NotI fragment (entire MDV gB gene). This fragment was inserted into the NotI sites of the plasmid pEL170 (Example 7, FIG. 9) in place of the 1405 bp NotI-NotI fragment containing the gene encoding the IBDV VP2 protein; this cloning made it possible to isolate the 8806 bp plasmid pEL181 (FIG. 17). This plasmid allows the insertion of the expression cassette MCMV-IE/MDV-gB into the intergenic site between the ORFs D and E of the ILTV virus.

11.3—Isolation and Purification of the Recombinant Virus vILTV17

The vILTV17 virus was isolated and purified after cotransfection of the DNA from the plasmid pEL181 previously linearized with the enzyme BssHII and of the viral DNA, as described in Example 3. This recombinant contains a cassette MCMV-IE/MDV gB in the intergenic site between the ORFs D and E of the ILTV (see Example 5).

Example 12

Construction of a Donor Plasmid for the Insertion of a Cassette for Expressing IBV Gene(s) into the Intergenic Site Between the ORFs D and E and Isolation of the Recombinant ILTV Virus According to the same strategy as that described above for the insertion of single cassettes (Examples 6, 7, 8, 9 and 11) or for the insertion of double cassettes (Example 10) into the site described above (Example 5), it is possible to prepare recombinant ILTV viruses expressing, at a high level, the Membrane (M) or Spike (S) proteins, or part of Spike (S1 or S2), or Nucleocapsid (N) of the avian infectious bronchitis virus (IBV). In particular, a double expression cassette was prepared with the S gene under the control of the CMV IE promoter and the M gene under the control of the associated promoter.

Example 13

Construction of Donor Plasmids for the Insertion of Cassettes for Expressing a Gene or Genes of Other Avian Pathogenic Agents or of an Immunomodulatory Peptide into the Site Described and Isolation of the Recombinant ILTV Viruses According to the same strategy as that described above for the insertion of single cassettes (Examples 6, 7, 8, 9 and 11) or for the insertion of double cassettes (Example 10) into the site described above (Example 5), it is possible to prepare recombinant ILTV viruses expressing, at a high level, immunogenes from CAV (and especially a double cassette for expressing genes encoding VP1 and VP2), from the chicken pneumovirosis virus, or other avian pathogenic agents, or alternatively immunomodulatory peptides and especially cytokines.

Example 14

Production of Vaccines

The recombinant viruses obtained according to the invention are produced on embryonated eggs. The viral solution harvested is then diluted in a stabilizing solution for freeze-drying, distributed at the rate of 1000 vaccinal doses per vial, and finally freeze-dried.

What is claimed is:

1. A modified ILTV virus comprising and expressing at least one heterologous nucleotide sequence, wherein the nucleotide sequence is inserted into the insertion locus formed by the intergenic region situated between the stop codons of the ORF D and ORF E of ILTV and which, in a specific ILTV strain, is defined between nucleotides 3873 and 4260 in SEQ ID NO: 1.

2. The modified ILTV virus according to claim 1, wherein the heterologous nucleotide sequence(s) is(are) inserted by simple insertion, or after total or partial deletion of the insertion locus.

3. The modified ILTV virus according to claim 1, wherein, to express the heterologous nucleotide sequence, the vector further comprises a strong eukaryotic promoter.

4. The modified ILTV virus according to claim 3, wherein the strong promoter is selected from the group consisting of: CMV immediate-early promoter, the Rous sarcoma virus (RSV) LTR promoter, and the SV40 virus early promoter.

5. The modified ILTV virus according to claim 1, which comprises at least two nucleotide sequences inserted into the insertion locus under the control of different eukaryotic promoters.

6. The modified ILTV virus according to claim 5, wherein the eukaryotic promoters are CMV immediate-early promoters of different animal origins.

7. The modified ILTV virus according to claim 5, which comprises a first nucleotide sequence under the control of a first promoter which is a CMV immediate early promoter and a second nucleotide sequence under the control of a second promoter, wherein the first and second promoters are arranged so that their 5' ends are adjacent.

8. The modified ILTV virus according to claim 1, which comprises, inserted into the insertion locus, an expression cassette comprising in succession: a promoter, two or more coding sequences separated in pairs by an IRES, and a polyadenylation signal.

9. The modified ILTV virus according to claim 1, wherein the heterologous nucleotide sequence encodes an antigenic polypeptide from an avian pathogenic agent.

10. The modified ILTV virus according to claim 9, wherein the heterologous nucleotide sequence encodes an antigen from an avian pathogenic agent selected from the group consisting of the Newcastle disease virus (NDV), the infectious bursal disease virus (IBDV), Marek's disease virus (MDV), the infectious bronchitis virus (IBV), the chicken anaemia virus (CAV), and the chicken pneumovirosis virus.

11. The modified ILTV virus according to claim 10, wherein the heterologous nucleotide sequence is selected from the group of nucleotide sequences encoding the NDV virus F and HN polypeptides.

12. The modified ILTV virus according to claim 10, wherein the heterologous nucleotide sequence is selected from the group of nucleotide sequences encoding the MDV polypeptides gB, gC, gD, and gH+gL.

13. The modified ILTV virus according to claim 10, which comprises at least one nucleotide sequence selected from the group of sequences encoding: the IBDV VP2 antigen; the S antigen of IBV; part of S, and the M and N antigens of the IBV; the CAV VP1 and VP2 antigens; and, the chicken pneumovirosis virus G and F antigens.

14. The modified ILTV virus according to claim 1, wherein the heteterologous nucleotide sequence comprises a nucleotide sequence encoding an immunomodulatory polypeptide.

15. The modified ILTV virus according to claim 14, wherein the immunomodulatory polypeptide is a cytokine.

16. The modified ILTV virus according to claim 4, wherein the strong promoter is murine or human CMV immediate-early promoter.

17. The modified ILTV virus according to claim 10, which comprises the nucleotide sequences encoding the NDV virus F and HN polypeptides.

18. The modified ILTV virus according to claim 4, wherein the CMV immediate-early promoter is of murine or human origin.

19. A multivalent vaccine, comprising, as a mixture or to be mixed, at least two modified ILTV viruses according to any one of claims 1–15, 17 and 18, the viruses comprising different heterologous nucleotide sequences.

20. A vaccine comprising a modified live ILTV virus according to any one of claims 1–15, 17 and 18.

* * * * *

UNITED STATES PATENT AND TRADEMARK OFFICE
CERTIFICATE OF CORRECTION

PATENT NO. : 6,306,400 B1  
DATED : October 23, 2001  
INVENTOR(S) : Michel Bublot et al.

It is certified that error appears in the above-identified patent and that said Letters Patent is hereby corrected as shown below:

<u>Title page,</u>  
Item [75], Inventors, change "Lyons" to -- Lyon --.  
Item [73], Assignee, change "Lyons" to -- Lyon --.

<u>Column 50,</u>  
Line 57, change "heteterologous" to -- heterologous --.

Signed and Sealed this

Sixth Day of August, 2002

*Attest:*

JAMES E. ROGAN  
*Attesting Officer*  *Director of the United States Patent and Trademark Office*

SEQUENCE LISTING

<160> NUMBER OF SEQ ID NOS: 28

<210> SEQ ID NO 1
<211> LENGTH: 7082
<212> TYPE: DNA
<213> ORGANISM: Infectious Laryngotracheitis Virus
<220> FEATURE:
<221> NAME/KEY: gene
<222> LOCATION: (1)..(7, 10)
<223> OTHER INFORMATION: T-20 12-8-66 (LT BLEN Vaccine)

<400> SEQUENCE: 1

```
gaattctaag cttgctttgt cgaaccagtt ttgttttctt tttgggggga gggtagcaca      60
ctctgcccga gtctcggcat tgacttaaca gtgatgtgaa acccggaaga tcgagcatga     120
actaatagca ttaaagaatt gttatccgag gaataatcgt ggacgcgaat ttactcgacc     180
gctaaaatct ttcttctact gagctggata cgtgaaattt ggtgagtata acctctcggg     240
atacatagct tttaaatacg gggcgtgcaa tattaaattc tgcactcggg gctgcaatgg     300
agcgcggagc tttatttgac aagaccgcca attgcaagga ctgggtctcg atcgggacta     360
ctgtgtgggg cgcgatcgat gcagatgacg gggacgactt agtctgggat tatgaaaata     420
```

-continued

```
gcccatatcc aagcatagtt tcctcactat tcccggggga agaaacggac tcggcaattt      480
gtaactctgt tgttgccgca aaccoctgta gcatacctcc tgggcggcag cgtttggcat      540
ggccatgctg ctgttttcgt cggccagaca gcttctccgt cccgcgcgtg gaagttaatg      600
ctcgccttgt tgccgcggtt gcactgataa ttttctcatt gcttgtagtg atctgtgttg      660
cgtcatattg ggggtaacat gtcttcagag gacacatcgg gattcctaac gccccccgca      720
agtgatgacg acactgaccc ttccgagcca ccaccaaatt tatgggatcc tcaccaggac      780
gattttccga gggacgctga ttccccaaac ccactttcct accoctggga tgactctgtg      840 aataatactg gggatacggg cagtaacgaa gatgactatg tagatatggg aggggtaggt      900
ggatccgaag actatgaaga cctcggtacg ggcggggact ctgactatga caatgtatct      960
acagcgaccg gcgggacgtg gtttccttcc cttacttctt ggtcatcaga ggaccacggc     1020
ccaacttctc cggaaaaccc tatgcaacaa cttcaagtaa caattcagca ggattcagat     1080
ccacagcagg aacccgatcc ccagcaagtt cccggtctcc agcaggaacc tgaccoccag     1140 caagatccac gagagcctcg tgatcctcct ccctatagtc cgcccccaga ggaccctttt     1200
gggctctcgc catttactag tgggatgggc gggtttgggc caccgtggcg tggccccagc     1260
caccctcgta tgatgaggca atgggggatg gaccttttac tacgactggg ggtcggcgac     1320
cttgctcacg caggcgcggt cgtcgccggt ctcgaggtcg atctcggcga cgcaattggt     1380
gtgcagcaaa gttgtgctca gaggcatgtt tgtggcatct cttttgggtt ggagtggcct     1440
taatgtgttg gtggctcttg tatcttattt tgcgcattgt ctggggacag actccgggat     1500
aaggaaggtt gtatccgcat ccagtactcc tcaataaaag cgtggtggtg ctacacgatg     1560
tctgttaatt ttacaactcc attttacagg tgatctagag agacgctgag tggcacttgt     1620
cccgacggga ccatgcagtc gaacagcagc gatgaggccc agtgtgatga tgtcgaggag     1680
ggatggtcgt ccatagctcc aggtgatgca ctggatacag atttcattcc agggccttgt     1740
gccacgtcca tacatggtat atccaaggca gtttattttt ttctgtgtgg agttaatctg     1800
gaggaatgta gtacactccc acagcatgtc caatctcacc catatggaca tcctgagctg     1860
aaatcaggca aatggtacaa gaggttttgc tccgggctag gcgaaattgg agatacaagc     1920
cagtgtcagc tgacacgact atgctgcact tccggaatgc cggcacagat ttttgggcct     1980
tcgagattca ggtctctgca acagaagcca acccatatgc gggcccaaga tttgctcact     2040
aggccttgcc atatactaga gttcgatgtt ggcgctgacc taatcaatct tttcttgtat     2100
atggaaccat gttcagggaa tcgatattgc gtacatttag gataccataa aactaatgcc     2160
atgcgtgttt tgagcggtgg tgggattcta tggggcagac ttccgtggaa ggacaacacc     2220
gaggagcacg ggtactcgtt gcctatgcga gtatttggga tcaaattgcc ccataaagtt     2280
tatgtggcat gtcgctgccc tgcaactcgg acggaactat tatttggtga gggggggta      2340 ggattcaacg cggaaaactt taaacagtgc ggacggttga aaaagagtg tgaatgtctg      2400 cagaaggctt gttttactgc acaaacggtg ttaggtgcgg catgtaagtt tactgtatac     2460
tcgagcaagg gacgaggtca agaaattctg ctatatcagg acccatgaat gctacaacgg     2520
taatgcctgt agtactgggt atgttaagta gagaaccccca caggtgtgca ggtacactca     2580
tactgtccag gtcctctgga aattgccgtg gatttcatga gacccaacac gatattccca     2640 ctaaccoggg tctgtatcct ctgtgtaatc atgagcaccc ttactatgtg acagttacag     2700
atgtatgcgg caactgttgt tcatggcttg agcgggtttt tgggagagta gctgcccctg     2760
```

-continued

```
ctggtctaag ctccgtatct gtatccatta aaggctccac ccacagcggg actgacgtga    2820
cagaagaacg tgaagaggac tcagggacac agcaaacctc ccacgacaaa ttgccggagc    2880
gcaaccgcat gggagatcaa aattcgaatt tgcggggaag agatcaatat tggccgcctg    2940
ccccacaccg tagtcattgt cactcggatt ttatattcga tgaacctgag ccagaaagtg    3000
gggaagacgt gcataacatg catcctccac gaggtgcaga tgagcaaaca gccgcttctg    3060
tgtcagcgct aatgcaaagt ctagcacaag cattggtgag tgcacaagct attagcagca    3120
tggtctctgg ctctgcttcc tcagtgggcg tagaagtaga ctgtgggtac agtcagactc    3180
atattacaga ggggccgggg agggaacaat tcggtagagt cccagaaaga gggccagagt    3240
atcctcaaga ttactgtgat atatatggtc ctgtaagtaa tgggcctgct ggatacagag    3300
caggaccacc agatgctcct agtatacaag ataggacctt cccatgcggc agaagatgcg    3360
acgaagcatg gcttgcctta gaagtaggga atatgcttg gatttcttct ggttcacata     3420
gtccaccttc tcagtatcat aacccttatg gttcacatag tccaccttcc cagtctcata    3480
acccttatgg tacatatagt ccgccttctc agtctcataa cccttatggc tcatatagtc    3540
cgccttccca gtatcataac ccttgtggta catatagtcc gccttctcag tctcgtaagc    3600
atgactattc acctccatat ccgatactca aaccaaagcc tcgattaccc ccaggctttg    3660
aaaatactgc tgggatgtgg cctcgatgtc ccctgggtt tgagggcgt ccatacaaat      3720 ctggggcat gggtaacttt cctggaagtg catggacggt aatagatagg gggtctaacc     3780
aatggccagc agacgtgcgg gggccattct cagatcaacg atgggccccc acagagcatg    3840
aaacgcgacg ttttgcggg tattacagct gagctctcat catacccata actccactca     3900
taacccaagg cccataaatc cataactcat aacataaatt catactttcc ggtcgtccag    3960
ggcaccacgt catcaacaag gattgcagat aaataaaaat gctccacgtt gtcggtgtcc    4020
gttgtattgt attctttatt atacctccgt aattttcgag agtcggggaa cattctaaaa    4080
attttaaccg tgcaatacta cagtgtattt acaaggccgg attgcaacag tgaactcatt    4140
acatcattga gctcgcggcg ccatctgctg accagtccac agagatggca atcttcagaa    4200
acgtaggatg gcaccaattc caatacaata ccgccatctg tcgataggtg tatagaactg    4260
tcaaaacaag tcgcaagaga aaatttccc tactgtatac tggcggctta gcagctgcgc     4320
acaaaccact ctgcattcct ctttgcggca cacatttgcg tgctgcgcca gaacgagtgg    4380 gatttttta gaacaggtcc caggatagta catgtcccac aatgttctgg ccgggtctat     4440
tgctttatga ttcatgacca tggcctctgg tcgcggatac acaattcttg agaaccggtc    4500
gaagaaggtc agtaataaag ttaaggaca ttttgcgcta ctcagcgata gctcctgaga     4560
tctagtggta tctcttagtt gactgccaat gctagagaga taacacggca ggattggccc    4620
cagatgcatg gctagagatt gacatgcgca gtagatgtta gagaagatag gatcgtgggg    4680
gtaaatcctt tcatcttcga actgatgcca aagcatccat acaagtgtct catcgcatgc    4740
aaaaagtagc tcttcaaatg agcagttcgc caaatataca gctcgtgaaa ttttttgccaa   4800 cctggctata tccggacgcg atgtccagcg gcctttcagt gaagctgcgc gcccacaaaa    4860
ctgcttccac gaagtgaatg cagcatctgc tgcaaggtca gatgatcccg aagacaaaaa    4920
tgctggaaag cagattcctc tatcacgatc gatatcatca caatcatcat catccactgc    4980
ccggtttacc atgtctaaaa gacatttctg atttctaat cttaactctt cagtaatgca     5040 cttttccgaga ccgccaaatg cagttgcggc cttttcaaaa tattgggccg tgttacgtt    5100 tcgcaactcc ttcgtttcgg tccgtgatga cgttgggcat cggacaaagt ctctccaaat    5160
```

-continued cggtcttcga agttcatccc gatttctttc ccaagacctg cgcgaatgct tcaacgaaac 5220
agtaaagata ggcgccctat atcgcttttc tggtgtacct gcacggcgcc tgggtctagg 5280
ggggatgcct cttcggactt ggatatgcgc acggcctctc ataaacttat ttcgagggct 5340
actgacccgc cttatggaag accgtacgct catacctgac tggttctcgt aacgggaacg 5400
aggctcgcca ttcgaatagc gacggcgccc cctgtcacgt gaatcacgga ctcgtttgga 5460
gctaccgcgc ccagatgacc gggatctgga gctactttct gtagaatgag atctgcggcg 5520
aatacaatgt gcttcgtggc gggattctga cctcgagcgt gaacggccat ccaggcgatc 5580
ttttgtcctt tccgttgctg atctcgcttc gctatgagta cttgtattgg aagatgatct 5640
ggaacgtgtc tcacgcctat ctttatttat tccagatttc tccggtctcc ccatcgcagt 5700
cagtgggttg atgtaccgcg tgcacgtcaa aaaaaatgaa accgcataca caacggttga 5760
gacttctacg gactcagaac aggtgtcgag ctcggagcag gtgctgagag gtaagctgac 5820
agtaatctgg cacgctgttt gcgagctaat ccacttggct tttgaatggt ctgggccact 5880
cccagtatac gtcataacac atacactgga acccacaaac tacaattgcg gtccagtagt 5940
tggtgcgaaa tattcacgca gacataataa tctgcgagaa cttctgcgga tccgacatgt 6000
aacttaatcc cgtaatgtag tgcggcatac cgtctaaacc gcaaacatcc gcttagtaga 6060
acacgcccta aaatcaccca cgagtatact ttgtacattc tgaccgccag atgttactcc 6120
tttcaaacaa tgatactcag ccgttagaac tagggctgtc ttcaaatgga ccaaattcag 6180
acacaatacc gcacaacgtg ttttaacatt ttattgccgt tcaaggcccg aacaatttgt 6240
tttgtatctt ctgttcgtat ttaaatgcaa ttattacaat gctcgcaatc gcagccacgc 6300
acaatgcacg caagactaag ctcgaagcaa tattggcaag gcatgaagtc aagatactgg 6360
gaggtttcga tgcggagact ttagtctttg ccggagtcgt gtaacccatc agtgataaga 6420
gttctagaac cgctgagaca attacatata cccaagcact aatttttacg tgttcatgta 6480
aaatatatgc acacggatca tagcaaatcc gcaatgtcat ggtggacata ataagcgatg 6540
ctaaatataa accgatctcg agtgttttca gtagtaagac ccctggatta cagacgcaaa 6600
atcctagagg gtctgctacg tagttcaagc ttttgcaatc tcggagatgt tcaaattccc 6660
tcaaaaaccg ttgcatcttt gtgtatggca cccgtaatat cagcctcgaa gtaaacgctg 6720
tccagtagtt aagatgatat gcatccatcg caatgcgttc tcgcggcaga catagcccga 6780
acattcgcct ctggcgacgg gtcagcaagt aacatatgta caataccgtc gaaatgaatg 6840
caactctgat ctgggaaaac catatgtaaa gcagacagtc tgccacttcc atgacgaata 6900
ctgttctttg gccggtggga tcaagacgag aaatgagtac agtctcattt tcaaaataag 6960
ctcctttaac acatctcgtc tggtggttct cgtagttgtt tagacgctgt gtatattttg 7020
tgaggacata aactagtgaa gaattaaatg tagcgggggg ttggtgaaca ggattgaatt 7080
cc 7082

<210> SEQ ID NO 2
<211> LENGTH: 126
<212> TYPE: PRT
<213> ORGANISM: Infectious Laryngotracheitis Virus

<400> SEQUENCE: 2

Met Glu Arg Gly Ala Leu Phe Asp Lys Thr Ala Asn Cys Lys Asp Trp
1 5 10 15

Val Ser Ile Gly Thr Thr Val Trp Gly Ala Ile Asp Ala Asp Asp Gly

-continued

```
                      20                    25                    30
Asp Asp Leu Val Trp Asp Tyr Glu Asn Ser Pro Tyr Pro Ser Ile Val
            35                    40                    45

Ser Ser Leu Phe Pro Gly Glu Glu Thr Asp Ser Ala Ile Cys Asn Ser
     50                    55                    60

Val Val Ala Ala Asn Pro Cys Ser Ile Pro Pro Gly Arg Gln Arg Leu
 65                    70                    75                    80

Ala Trp Pro Cys Cys Cys Phe Arg Arg Pro Asp Ser Phe Ser Val Pro
                85                    90                    95

Arg Val Glu Val Asn Ala Arg Leu Val Ala Ala Val Ala Leu Ile Ile
                100                   105                   110

Phe Ser Leu Leu Val Ile Cys Val Ala Ser Tyr Trp Gly
            115                   120                   125

<210> SEQ ID NO 3
<211> LENGTH: 254
<212> TYPE: PRT
<213> ORGANISM: Infectious Laryngotracheitis Virus

<400> SEQUENCE: 3

Met Ser Ser Glu Asp Thr Ser Gly Phe Leu Thr Pro Pro Ala Ser Asp
 1               5                  10                  15

Asp Asp Thr Asp Pro Ser Glu Pro Pro Asn Leu Trp Asp Pro His
                20                  25                  30

Gln Asp Asp Phe Pro Arg Asp Ala Asp Ser Pro Asn Pro Leu Phe Tyr
            35                    40                    45

Pro Trp Asp Asp Ser Val Asn Asn Thr Gly Asp Thr Gly Ser Asn Glu
     50                    55                    60

Asp Asp Tyr Val Asp Met Gly Val Gly Ser Glu Asp Tyr Glu
 65                    70                    75                    80

Asp Leu Gly Thr Gly Gly Asp Ser Asp Tyr Asp Asn Val Ser Thr Ala
                85                    90                    95

Thr Gly Gly Thr Trp Phe Pro Ser Leu Thr Ser Trp Ser Ser Glu Asp
                100                   105                   110

His Gly Pro Thr Ser Pro Gly Asn Pro Met Gln Gln Leu Gln Val Thr
            115                   120                   125

Ile Gln Gln Asp Ser Asp Pro Gln Gln Glu Pro Asp Pro Gln Gln Val
    130                   135                   140

Pro Gly Leu Gln Gln Glu Pro Asp Pro Gln Gln Asp Pro Arg Glu Pro
145                   150                   155                   160

Arg Asp Pro Pro Tyr Ser Pro Pro Glu Asp Pro Phe Gly Leu
                165                   170                   175

Ser Pro Phe Thr Ser Gly Met Gly Gly Phe Gly Pro Trp Arg Gly
            180                   185                   190

Pro Ser His Pro Arg Met Met Arg Gln Trp Gly Met Asp Leu Leu Leu
        195                   200                   205

Arg Leu Gly Val Gly Asp Leu Ala His Ala Gly Ala Val Val Ala Gly
    210                   215                   220

Leu Glu Val Asp Leu Gly Asp Ala Ile Gly Val Gln Gln Ser Cys Ala
225                   230                   235                   240

Gln Ala His Val Cys Gly Ile Ser Phe Gly Leu Glu Trp Pro
                245                   250

<210> SEQ ID NO 4
<211> LENGTH: 291
```

```
<212> TYPE: PRT
<213> ORGANISM: Infectious Laryngotracheitis Virus

<400> SEQUENCE: 4

Met Gln Ser Asn Ser Ser Asp Glu Ala Gln Cys Asp Val Glu Glu
  1               5                  10                  15

Gly Trp Ser Ser Ile Ala Pro Gly Asp Ala Leu Asp Thr Asp Phe Ile
                 20                  25                  30

Pro Gly Pro Cys Ala Thr Ser Ile His Gly Ile Ser Lys Ala Val Tyr
             35                  40                  45

Phe Phe Leu Cys Gly Val Asn Leu Glu Glu Cys Ser Thr Leu Pro Gln
         50                  55                  60

His Val Gln Ser His Pro Tyr Gly His Pro Glu Leu Lys Ser Gly Lys
 65                  70                  75                  80

Trp Tyr Lys Arg Phe Cys Ser Gly Leu Gly Glu Ile Gly Asp Thr Ser
                 85                  90                  95

Gln Cys Gln Leu Thr Arg Leu Cys Cys Thr Ser Gly Met Pro Ala Gln
            100                 105                 110

Ile Phe Gly Pro Ser Arg Phe Arg Ser Leu Gln Lys Pro Thr His
            115                 120                 125

Met Arg Ala Gln Asp Leu Leu Thr Ala Pro Cys His Ile Leu Glu Phe
    130                 135                 140

Asp Val Gly Ala Asp Leu Ile Asn Leu Phe Leu Tyr Met Glu Pro Cys
145                 150                 155                 160

Ser Gly Asn Arg Tyr Cys Val His Leu Gly Tyr His Lys Thr Asn Ala
                165                 170                 175

Met Arg Val Leu Ser Gly Gly Ile Leu Trp Gly Arg Leu Pro Trp
            180                 185                 190

Lys Asp Asn Thr Glu Glu His Gly Tyr Ser Leu Pro Met Arg Val Phe
        195                 200                 205

Gly Ile Lys Leu Pro His Lys Val Tyr Val Ala Cys Arg Cys Pro Ala
    210                 215                 220

Thr Arg Thr Glu Leu Leu Phe Gly Glu Gly Val Gly Phe Asn Ala
225                 230                 235                 240

Glu Asn Phe Lys Gln Cys Gly Arg Leu Lys Lys Glu Cys Glu Cys Leu
                245                 250                 255

Gln Lys Ala Cys Phe Thr Ala Gln Thr Val Leu Gly Ala Ala Cys Lys
            260                 265                 270

Phe Thr Val Tyr Ser Ser Lys Gly Arg Gly Gln Glu Ile Leu Leu Tyr
            275                 280                 285

Gln Asp Pro
    290

<210> SEQ ID NO 5
<211> LENGTH: 455
<212> TYPE: PRT
<213> ORGANISM: Infectious Laryngotracheitis Virus

<400> SEQUENCE: 5

Met Asn Ala Thr Thr Val Met Pro Val Val Leu Gly Met Leu Ser Arg
  1               5                  10                  15

Glu Pro His Arg Cys Ala Gly Thr Leu Ile Leu Ser Arg Ser Ser Gly
                 20                  25                  30

Asn Cys Arg Gly Phe His Glu Thr Gln His Asp Ile Pro Thr Asn Pro
             35                  40                  45
```

```
Gly Leu Tyr Pro Leu Cys Asn His Glu His Pro Tyr Tyr Val Thr Val
 50                  55                  60

Thr Asp Val Cys Gly Asn Cys Cys Ser Trp Leu Glu Arg Val Phe Gly
 65                  70                  75                  80

Arg Val Ala Ala Pro Ala Gly Leu Ser Ser Val Ser Val Ser Ile Lys
                 85                  90                  95

Gly Ser Thr His Ser Gly Thr Asp Val Thr Glu Glu Arg Glu Glu Asp
                100                 105                 110

Ser Gly Thr Gln Gln Thr Ser His Asp Lys Leu Pro Glu Arg Asn Arg
            115                 120                 125

Met Gly Asp Gln Asn Ser Asn Leu Arg Gly Arg Asp Gln Tyr Trp Pro
    130                 135                 140

Pro Ala Pro His Arg Ser His Cys His Ser Asp Phe Ile Phe Asp Glu
145                 150                 155                 160

Pro Glu Pro Glu Ser Gly Glu Asp Val His Asn Met His Pro Pro Arg
                165                 170                 175

Gly Ala Asp Glu Gln Thr Ala Ala Ser Val Ser Ala Leu Met Gln Ser
                180                 185                 190

Leu Ala Gln Ala Leu Val Ser Ala Gln Ala Ile Ser Ser Met Val Ser
            195                 200                 205

Gly Ser Ala Ser Ser Val Gly Val Glu Val Asp Cys Gly Tyr Ser Gln
    210                 215                 220

Thr His Ile Thr Glu Gly Pro Gly Arg Glu Gln Phe Gly Arg Val Pro
225                 230                 235                 240

Glu Arg Gly Pro Glu Tyr Pro Gln Asp Tyr Cys Asp Ile Tyr Gly Pro
                245                 250                 255

Val Ser Asn Gly Pro Ala Gly Tyr Arg Ala Gly Pro Pro Asp Ala Pro
                260                 265                 270

Ser Ile Gln Asp Arg Thr Phe Pro Cys Gly Arg Arg Cys Asp Glu Ala
            275                 280                 285

Trp Leu Ala Leu Glu Val Gly Asn Met Pro Trp Ile Ser Ser Gly Ser
    290                 295                 300

His Ser Pro Pro Ser Gln Tyr His Asn Pro Tyr Gly Ser His Ser Pro
305                 310                 315                 320

Pro Ser Gln Ser His Asn Pro Tyr Gly Thr Tyr Ser Pro Pro Ser Gln
                325                 330                 335

Ser His Asn Pro Tyr Gly Ser Tyr Ser Pro Ser Gln Tyr His Asn
                340                 345                 350

Pro Cys Gly Thr Tyr Ser Pro Pro Ser Gln Ser Arg Lys His Asp Tyr
            355                 360                 365

Ser Pro Pro Tyr Pro Ile Leu Lys Pro Lys Pro Arg Leu Pro Pro Gly
    370                 375                 380

Phe Gly Asn Thr Ala Gly Met Trp Pro Arg Cys Pro Pro Gly Phe Glu
385                 390                 395                 400

Gly Arg Pro Tyr Lys Ser Gly Met Gly Asn Phe Pro Gly Ser Ala
                405                 410                 415

Trp Thr Val Ile Asp Arg Gly Ser Asn Gln Trp Pro Ala Asp Val Arg
            420                 425                 430

Gly Pro Phe Ser Asp Gln Arg Trp Ala Pro Thr Glu His Glu Thr Arg
    435                 440                 445

Arg Phe Cys Gly Tyr Tyr Ser
450                 455
```

<210> SEQ ID NO 6
<211> LENGTH: 544
<212> TYPE: PRT
<213> ORGANISM: Infectious Laryngotracheitis Virus

<400> SEQUENCE: 6

```
Met Thr Tyr Thr Gly Ser Gly Pro Asp His Ser Lys Ala Lys Trp Ile
  1               5                  10                  15

Ser Ser Gln Thr Ala Cys Gln Ile Thr Val Ser Leu Pro Leu Ser Thr
                 20                  25                  30

Cys Ser Glu Leu Asp Thr Cys Ser Glu Ser Val Glu Val Ser Thr Val
             35                  40                  45

Val Tyr Ala Val Ser Phe Phe Leu Thr Cys Thr Arg Tyr Ile Asn Pro
     50                  55                  60

Leu Thr Ala Met Gly Arg Pro Glu Lys Ser Gly Ile Asn Lys Asp Arg
 65                  70                  75                  80

Arg Glu Thr Arg Ser Arg Ser Ser Asn Thr Ser Thr His Ser Glu
                 85                  90                  95

Ala Arg Ser Ala Thr Glu Arg Thr Lys Asp Arg Leu Asp Gly Arg Ser
            100                 105                 110

Arg Ser Arg Ser Glu Ser Arg His Glu Ala His Cys Ile Arg Arg Arg
        115                 120                 125

Ser His Ser Thr Glu Ser Ser Ser Arg Ser Arg Ser Ser Gly Arg Gly
    130                 135                 140

Ser Ser Lys Arg Val Arg Asp Ser Arg Asp Arg Gly Arg Arg Arg Tyr
145                 150                 155                 160

Ser Asn Gly Glu Pro Arg Ser Arg Tyr Glu Asn Gln Ser Gly Met Ser
                165                 170                 175

Val Arg Ser Ser Ile Arg Arg Val Ser Ser Pro Arg Asn Lys Phe Met
            180                 185                 190

Arg Gly Arg Ala His Ile Gln Val Arg Arg Gly Ile Pro Pro Ala Pro
        195                 200                 205

Arg Arg Arg Ala Gly Thr Pro Glu Lys Arg Tyr Arg Ala Pro Ile Phe
    210                 215                 220

Thr Val Ser Leu Lys His Ser Arg Arg Ser Trp Glu Arg Asn Arg Asp
225                 230                 235                 240

Glu Leu Arg Arg Pro Ile Trp Arg Asp Phe Val Arg Cys Pro Thr Ser
                245                 250                 255

Ser Arg Thr Glu Thr Lys Gly Leu Arg Asn Val Thr Pro Ala Gln Tyr
            260                 265                 270

Phe Glu Lys Ala Ala Thr Ala Phe Gly Gly Leu Gly Lys Cys Ile Thr
        275                 280                 285

Glu Glu Leu Arg Leu Glu Asn Gln Lys Cys Leu Leu Asp Met Val Asn
    290                 295                 300

Arg Ala Val Asp Asp Asp Cys Asp Asp Ile Asp Arg Asp Arg Gly
305                 310                 315                 320

Ile Cys Phe Pro Ala Phe Leu Ser Ser Gly Ser Ser Asp Leu Ala Ala
                325                 330                 335

Asp Ala Ala Phe Thr Ser Trp Lys Gln Phe Cys Gly Arg Ala Ala Ser
            340                 345                 350

Leu Lys Gly Arg Trp Thr Ser Arg Pro Asp Ile Ala Arg Leu Ala Lys
        355                 360                 365

Ile Ser Arg Ala Val Tyr Leu Ala Asn Cys Ser Phe Glu Glu Leu Leu
    370                 375                 380
```

-continued

```
Phe Ala Cys Asp Glu Thr Leu Val Trp Met Leu Trp His Gln Phe Glu
385                 390                 395                 400

Asp Glu Arg Ile Tyr Pro His Asp Pro Ile Phe Ser Asn Ile Tyr Cys
                405                 410                 415

Ala Cys Gln Ser Leu Ala Met His Leu Gly Pro Ile Leu Pro Cys Tyr
            420                 425                 430

Leu Ser Ser Ile Gly Ser Gln Leu Arg Asp Thr Thr Arg Ser Gln Glu
        435                 440                 445

Leu Ser Leu Ser Ser Ala Lys Cys Pro Leu Thr Leu Leu Leu Thr Phe
    450                 455                 460

Phe Asp Arg Phe Ser Arg Ile Val Tyr Pro Arg Pro Glu Ala Met Val
465                 470                 475                 480

Met Asn His Lys Ala Ile Asp Pro Ala Arg Thr Leu Trp Asp Met Tyr
                485                 490                 495

Tyr Pro Gly Thr Cys Ser Lys Lys Ile Pro Leu Val Leu Ala Gln His
            500                 505                 510

Ala Asn Val Cys Arg Lys Glu Glu Cys Arg Val Val Cys Ala Gln Leu
        515                 520                 525

Leu Ser Arg Gln Tyr Thr Val Gly Lys Phe Phe Ser Cys Asp Leu Phe
    530                 535                 540

<210> SEQ ID NO 7
<211> LENGTH: 286
<212> TYPE: PRT
<213> ORGANISM: Infectious Laryngotracheitis Virus

<400> SEQUENCE: 7

Glu Phe Asn Pro Val His Gln Pro Pro Ala Thr Phe Asn Ser Ser Leu
  1               5                  10                  15

Val Tyr Val Leu Thr Lys Tyr Thr Gln Arg Leu Asn Asn Tyr Glu Asn
            20                  25                  30

His Gln Thr Arg Cys Val Lys Gly Ala Tyr Phe Glu Asn Glu Thr Val
        35                  40                  45

Leu Ile Ser Arg Leu Asp Pro Thr Gly Gln Arg Thr Val Phe Val Met
     50                  55                  60

Glu Val Ala Asp Cys Leu Leu Tyr Ile Trp Phe Ser Gln Ile Arg Val
 65                  70                  75                  80

Ala Phe Ile Ser Thr Val Leu Tyr Ile Cys Tyr Leu Leu Thr Arg Arg
                 85                  90                  95

Gln Arg Arg Met Phe Gly Leu Cys Leu Pro Arg Glu Arg Ile Ala Met
            100                 105                 110

Asp Ala Tyr His Leu Asn Tyr Trp Thr Ala Phe Thr Ser Arg Leu Ile
        115                 120                 125

Leu Arg Val Pro Tyr Thr Lys Met Gln Arg Phe Leu Arg Glu Phe Glu
    130                 135                 140

His Leu Arg Asp Cys Lys Ser Leu Asn Tyr Val Ala Asp Pro Leu Gly
145                 150                 155                 160

Phe Cys Val Cys Asn Pro Gly Val Leu Leu Leu Lys Thr Leu Glu Ile
                165                 170                 175

Gly Leu Tyr Leu Ala Ser Leu Ile Met Ser Thr Met Thr Leu Arg Ile
            180                 185                 190

Cys Tyr Asp Pro Cys Ala Tyr Ile Leu His Glu His Val Lys Ile Ser
        195                 200                 205

Ala Trp Val Tyr Val Ile Val Ser Ala Val Leu Glu Leu Leu Ser Leu
    210                 215                 220
```

Met Gly Tyr Thr Thr Pro Ala Lys Thr Lys Val Ser Ala Ser Lys Pro
225                 230                 235                 240

Pro Ser Ile Leu Thr Ser Cys Leu Ala Asn Ile Ala Ser Ser Leu Val
            245                 250                 255

Leu Arg Ala Leu Cys Val Ala Ala Ile Ala Ser Ile Val Ile Ile Ala
            260                 265                 270

Phe Lys Tyr Glu Gln Lys Ile Gln Asn Lys Leu Phe Gly Pro
            275                 280                 285

<210> SEQ ID NO 8
<211> LENGTH: 2521
<212> TYPE: DNA
<213> ORGANISM: Newcastle Disease Virus HN

<400> SEQUENCE: 8

| | | | | |
|---|---|---|---|---|
| tgctacctga | tgtacaagca | aaaggcacaa | caaaagacct | tgttatggct | tgggaataat | 60 |
| acccttgatc | agatgagagc | cactacaaaa | atatgaatac | aaacgagagg | cggaggtatc | 120 |
| cccaatagca | atttgcgtgt | aaattctggc | aacctgttaa | ttagaagaat | taagaaaaaa | 180 |
| ccactggatg | taagtgacaa | caagcaata | cacgggtaga | acggtcggag | aagccacccc | 240 |
| tcaatcggga | atcaggcctc | acaacgtcct | ttctaccgca | tcatcaatag | cagacttcgg | 300 |
| tcatggaccg | tgcagttagc | agagttgcgc | tagagaatga | agaaagagaa | gcaaagaata | 360 |
| catggcgctt | tgtattccgg | attgcaatct | tacttttaat | agtaacaacc | ttagccatct | 420 |
| ctgcaaccgc | cctggtatat | agcatggagg | ctagcacgcc | tggcgacctt | gttggcatac | 480 |
| cgactatgat | ctcaaggca | gaagaaaaga | ttacatctgc | actcagttct | aatcaagatg | 540 |
| tagtagatag | gatatataag | caggtggccc | ttgagtctcc | attggcgttg | ctaaacactg | 600 |
| aatctgtaat | tatgaatgca | ataacgtctc | tctcttatca | aatcaatgga | gctgcaaata | 660 |
| atagcgggtg | tggggcacct | gttcatgacc | cagattatat | cgggggata | ggcaaagaac | 720 |
| ttattgtgga | tgacgctagt | gatgtcacat | cattctatcc | ctctgcgttc | caagaacacc | 780 |
| tgaactttat | cccggcacct | actacaggat | caggttgcac | tcggataccc | tcattcgaca | 840 |
| taagcgctac | ccactactgt | tacactcaca | atgtgatatt | atctggttgc | agagatcact | 900 |
| cacactcata | tcagtactta | gcacttggcg | tgcttcggac | atctgcaaca | gggagggtat | 960 |
| tcttttctac | tctgcgttcc | atcaatttgg | atgacagcca | aaatcggaag | tcttgcagtg | 1020 |
| tgagtgcaac | tcccttaggt | tgtgatatgc | tgtgctctaa | aatcacagag | actgaggaag | 1080 |
| aggattatag | ttcaattacg | cctacatcga | tggtgcacgg | aaggttaggg | tttgacggtc | 1140 |
| aataccatga | gaaggactta | gacgtcataa | ctttatttaa | ggattgggtg | gcaaattacc | 1200 |
| caggagtggg | gggtgggtct | tttattaaca | accgcgtatg | gttcccagtc | tacggagggc | 1260 |
| taaaacccaa | ttcgcctagt | gacaccgcac | aagaagggag | atatgtaata | tacaagcgct | 1320 |
| acaatgacac | atgcccagat | gaacaagatt | accagattcg | gatggctaag | tcttcatata | 1380 |
| agcctgggcg | gtttggtgga | aaacgcgtac | agcaggccat | cttatctatc | aaggtgtcaa | 1440 |
| catctttggg | cgaggacccg | gtgctgactg | taccgcctaa | tacaatcaca | ctcatggggg | 1500 |
| ccgaaggcag | agttctcaca | gtagggacat | ctcatttctt | gtaccagcga | gggtcttcat | 1560 |
| acttctctcc | tgctttatta | taccctatga | cagtcaacaa | caaaacggct | actcttcata | 1620 |
| gtccttacac | attcaatgct | ttcactaggc | caggtagtgt | cccttgtcag | gcatcagcaa | 1680 |
| gatgccccaa | ctcatgtgtc | actggagttt | atactgatcc | gtatccctta | gtcttccata | 1740 |

```
ggaaccatac cttgcggggg gtattcggga caatgcttga tgatgaacaa gcaagactta    1800
accctgtatc tgcagtattt gataacatat cccgcagtcg cataacccgg gtaagttcaa    1860
gccgtactaa ggcagcatac acgacatcga catgttttaa agttgtcaag accaataaaa    1920
catattgcct cagcattgca gaaatatcca ataccctctt cggggaattc aggatcgttc    1980
ctttactagt tgagattctc aaggatgatg ggatttaaga agcttggtct ggccagttga    2040
gtcaactgcg agagggtcgg aaagatgaca ttgtgtcacc ttttttttgt aatgccaagg    2100
atcaaactgg ataccggcgc gagcccgaat cctatgctgc cagtcagcca taatcagata    2160
gtactaatat gattagtctt aatcttgtcg atagtaactt ggttaagaaa aaatatgagt    2220
ggtagtgaga tacacagcta acaaactcac gagagatagc acgggtagga catggcgagc    2280
tccggtcccg aaagggcaga gcatcagatt atcctaccag agtcacatct gtcctcacca    2340
ttggtcaagc acaaactgct ctattactgg aaattaactg gcgtaccgct tcctgacgaa    2400
tgtgacttcg accacctcat tatcagccga caatggaaga aaatacttga atcggccact    2460
cctgacactg agaggatgat aaagctcggg cgggcagtac accagactct cgaccaccgc    2520
c                                                                    2521

<210> SEQ ID NO 9
<211> LENGTH: 569
<212> TYPE: PRT
<213> ORGANISM: Newcastle Disease Virus HN

<400> SEQUENCE: 9

Met Asp Arg Ala Val Ser Arg Val Ala Leu Glu Asn Glu Glu Arg Glu
 1               5                  10                  15

Ala Lys Asn Thr Trp Arg Phe Val Phe Arg Ile Ala Ile Leu Leu Leu
             20                  25                  30

Ile Val Thr Thr Leu Ala Ile Ser Ala Thr Ala Leu Val Tyr Ser Met
         35                  40                  45

Glu Ala Ser Thr Pro Gly Asp Leu Val Gly Ile Pro Thr Met Ile Ser
     50                  55                  60

Lys Ala Glu Glu Lys Ile Thr Ser Ala Leu Ser Ser Asn Gln Asp Val
 65                  70                  75                  80

Val Asp Arg Ile Tyr Lys Gln Val Ala Leu Glu Ser Pro Leu Ala Leu
                 85                  90                  95

Leu Asn Thr Glu Ser Val Ile Met Asn Ala Ile Thr Ser Leu Ser Tyr
            100                 105                 110

Gln Ile Asn Gly Ala Ala Asn Asn Ser Gly Cys Gly Ala Pro Val His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Ile Ser Ala Thr His Tyr Cys Tyr Thr His Asn Val Ile
            180                 185                 190

Leu Ser Gly Cys Arg Asp His Ser His Ser Tyr Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Ser Gln Asn Arg Lys Ser Cys Ser Val
```

```
225                 230                 235                 240
Ser Ala Thr Pro Leu Gly Cys Asp Met Leu Cys Ser Lys Ile Thr Glu
                245                 250                 255

Thr Glu Glu Asp Tyr Ser Ser Ile Thr Pro Thr Ser Met Val His
            260                 265                 270

Gly Arg Leu Gly Phe Asp Gly Gln Tyr His Glu Lys Asp Leu Asp Val
        275                 280                 285

Ile Thr Leu Phe Lys Asp Trp Val Ala Asn Tyr Pro Gly Val Gly Gly
    290                 295                 300

Gly Ser Phe Ile Asn Asn Arg Val Trp Phe Pro Val Tyr Gly Gly Leu
305                 310                 315                 320

Lys Pro Asn Ser Pro Ser Asp Thr Ala Gln Glu Gly Arg Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Glu
    370                 375                 380

Asp Pro Val Leu Thr Val Pro Pro Asn Thr Ile Thr Leu Met Gly Ala
385                 390                 395                 400

Glu Arg Arg Val Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Asn
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Val Thr Gly Val Tyr Thr Asp Pro Tyr Pro Leu Val Phe His Arg
465                 470                 475                 480

Asn His Thr Leu Arg Gly Val Phe Gly Thr Met Leu Asp Asp Glu Gln
                485                 490                 495

Ala Arg Leu Asn Pro Val Ser Ala Val Phe Asp Asn Ile Ser Arg Ser
            500                 505                 510

Arg Ile Thr Arg Val Ser Ser Arg Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Asp Ile Leu Lys Asp
                565

<210> SEQ ID NO 10
<211> LENGTH: 3116
<212> TYPE: DNA
<213> ORGANISM: Infectious Laryngotracheitis Virus

<400> SEQUENCE: 10
gaattcaatc ctgttcacca accccccgct acatttaatt cttcactagt ttatgtcctc      60
acaaaatata cacagcgtct aaacaactac gagaaccacc agacgagatg tgttaaagga     120
gcttattttg aaaatgagac tgtactcatt tctcgtctga tcccactggc caaagaacag     180
```

```
tattcgtcat ggaagtggca gactgtctct ttacatatgg ttttcccaga tcagagttgc    240
atttccacgg ttattgtaca tatgttactt gctgacccgt gccagaggcg aatgttcggc    300
tctgtctgcc gcgagaacgc attgcgattg gatgcatatc atctaaacta ctggacagcg    360
tttacttcga ggctgatatt acgggtgcca tacacaaaga tgcaacggtt tttgagggaa    420
tttgaacatg tccgagattg caaaagcttg aactacgtag cagaccctct aggcttttgc    480
atctgtaatc caggggtctt agtactgaaa acactcgaga tcggtttata tttagcatcg    540
cttattatgt ccaccatgac attgcggatt tgctatgatc cgtgtgcata tattttacat    600
gaacacgtaa aaattagtgc ttgggtatat gtaattgtct cagcggttct agaactctta    660
tcactgatgg gttacacgac tccggcaaag actaaagtct ccgcatcgaa acctcccagt    720
atcttgactt catgccttgc caatattgct tcgagcttag tcttgcgtgc attgtgcgtg    780
gctgcgattg cgagcattgt aataattgca tttaaatacg aacagaagat acaaaacaaa    840
ttgttcgggc cttaacggc aataaaatgt taaaacacgt tgtgcggtgt tgtgtctgaa    900
tttggtccat ttgaagacag ccctagttct aacggctgag tatcattgtt tgaaaggagt    960
aacatctggc ggtcagaatg tacaaagtat actcgtgggt gattttaggg cgtgttctac   1020
taagcggatg tttgcggttt agacggcatg ccgcactaca ttcgggatt aagttacatg    1080 tcggatccgc agaagttctc gcagattatt atgtctgcgt gaatatttcg caccaactac   1140
tggatcgcaa ttgtagtttg tgggttccag tgtatgtgtt atgacgtata ctgggagtgg   1200
cccagaccat tcaaaagcca agtggattag ctcgcaaaca gcgtgccaga ttactgtcag   1260 cttaccttc agcacctgct ccgagcttga cacctgttct gagtccgtag aagtctcaac    1320
cgttgtgtat gcggtttcat ttttttttgac gtgcacgcgg tacatcaacc cactgactgc   1380
gatggagacc ggagaaatct ggaagaaata agatagcgt gagacacgtt cagagcatct    1440
tcaatacaag tactcatagc gaagcgagat cagcaacggc ccggacaaaa gatcgccctg   1500
gatggccgtt cacgctgagg tcagaatccc gccacgaagc acattgtatt cgccgcagat   1560
ctcattctac agaaagtagc tccagatccc ggttcatctg ggcgcggtac gtccaaacga   1620
gtccgtgatt caagtgacag ggggcgccgt cgctgttcga atggcgaggc ctcgttcccg   1680
ttacgagaac cagtcaggta tgagcgtacg gtcttccata aggcgggtca gtagccctcg   1740
aaataagttt atgagaggcc gtgcgcatat ccaagtccga agaggcatcc ccctagacc    1800 caggcgccgt gcaggtacac cagaaaagcg atatagggcg cctatctta ctgtttcgtt    1860 gaagcattcg cgcaggtctt gggaaagaaa tcgggatgaa cttcgaagac cgatttggag   1920
agactttgtc cgatgcccaa cgtcatcacg gaccgaaacg aaggagttgc gaaacgtaac   1980
accggcccaa tattttgaaa aggccgcaac tgcatttggc ggtctcggaa agtgcattac   2040
tgaagagtta agattagaaa atcagaaatg tcttttagac atggtaaacc gggcagtgga   2100
tgatgatgat tgtgatgata tcgatcgtga tagaggaatc tgctttccag cattttttgtc   2160 ttcgggatca tctgaccttg cagccgatgc tgcattcact tcgtggaagc agttttgtgg   2220
gcgcgcagct tcactgaaag gccgctggac atcgcgtccg gatatagcca ggttggcaaa   2280
aatttcacga gctgtatatt tggcgaactg ctcatttgaa gagctacttt ttgcatgcga   2340
tgagacactt gtatggatgc tttggcatca gttcgaagat gaaaggattt accccacga    2400 tcctatcttc tctaacatct actgcgcatg tcaatctcta gccatgcatc tggggccaat   2460
cctgccgtgt tatctctcta gcattggcag tcaactaaga gataccacta gatctcagga   2520
gctatcactg agtagcgcaa aatgtccttt aactttatta ctgaccttct tcgaccggtt   2580
```

-continued

```
ctcaagaatt gtgtatccgc gatcagaggc catagtcatg aatcataaag caatagaccc      2640
ggccagaaca ttgtgggaca tgtactatcc tgggacctgt tctaaaaaaa tcccactcgt      2700
tctgcgcagc acgcaaatgt gtgccgcaaa gaggaatgca gagtggtttg tgcgcagctc      2760
taagccgcag tatacagtag ggaaattttc tcttgcgact tgtttgacag ttctatacac      2820
ctatcgacac atggcggtat tgtattggaa ttggtgccat cctacgtttc tgaagattgc      2880
catctctgtg actggtcagc agatggcgcc gcgagctcaa tgatgtaagc gttcactgtt      2940
gcaatccggc cttgtaaata cactgtagta ttagcacggt tgaaaatttt tagaatgttc      3000
cccgactctc gaaaattaac ggaggtataa taaagaacac aatacaacgg acaccgacaa      3060
cgtggagcat ttttatttag tctgcaaatc cttggttgat gaacgtggtg ccctgg         3116
```

<210> SEQ ID NO 11
<211> LENGTH: 284
<212> TYPE: PRT
<213> ORGANISM: Newcastle Disease Virus HN

<400> SEQUENCE: 11

```
Glu Phe Asn Pro Val His Gln Pro Pro Ala Thr Phe Asn Ser Ser Leu
  1               5                  10                  15

Val Tyr Val Leu Thr Lys Tyr Thr Gln Arg Leu Asn Asn Tyr Glu Asn
             20                  25                  30

His Gln Thr Arg Cys Val Lys Gly Ala Tyr Phe Glu Asn Glu Thr Val
         35                  40                  45

Leu Ile Ser Arg Leu Ile Pro Leu Ala Lys Glu Gln Tyr Ser Ser Trp
     50                  55                  60

Lys Trp Gln Thr Val Ser Leu His Met Val Phe Pro Asp Gln Ser Cys
 65                  70                  75                  80

Ile Ser Thr Val Ile Val His Met Leu Leu Ala Asp Pro Cys Gln Arg
                 85                  90                  95

Arg Met Phe Gly Ser Val Cys Arg Glu Asn Ala Leu Arg Leu Asp Ala
            100                 105                 110

Tyr His Leu Asn Tyr Trp Thr Ala Phe Thr Ser Arg Leu Ile Leu Arg
        115                 120                 125

Val Asp Tyr Thr Lys Met Gln Arg Phe Leu Arg Glu Phe Glu His Val
    130                 135                 140

Arg Asp Cys Lys Ser Leu Asn Tyr Val Ala Asp Pro Leu Gly Phe Cys
145                 150                 155                 160

Ile Cys Asn Pro Gly Val Leu Val Leu Lys Thr Leu Glu Ile Gly Leu
                165                 170                 175

Tyr Leu Ala Ser Leu Ile Met Ser Thr Met Thr Leu Arg Ile Cys Tyr
            180                 185                 190

Asp Pro Cys Ala Tyr Ile Leu His Glu His Val Lys Ile Ser Ala Trp
        195                 200                 205

Val Tyr Val Ile Val Ser Ala Val Leu Glu Leu Leu Ser Leu Met Gly
    210                 215                 220

Tyr Thr Thr Pro Ala Lys Thr Lys Val Ser Ala Ser Lys Pro Pro Ser
225                 230                 235                 240

Ile Leu Thr Ser Cys Leu Ala Asn Ile Ala Ser Ser Leu Val Leu Arg
                245                 250                 255

Ala Leu Cys Val Ala Ala Ile Ser Ile Val Ile Ala Phe Lys
            260                 265                 270

Tyr Glu Gln Lys Ile Gln Asn Lys Leu Phe Gly Pro
```

```
            275                 280

<210> SEQ ID NO 12
<211> LENGTH: 420
<212> TYPE: PRT
<213> ORGANISM: Newcastle Disease Virus HN

<400> SEQUENCE: 12

Met Ala Arg Pro Arg Ser Arg Tyr Glu Asn Gln Ser Gly Met Ser Val
  1               5                  10                  15

Arg Ser Ser Ile Arg Arg Val Ser Ser Pro Arg Asn Lys Pro Met Arg
             20                  25                  30

Gly Arg Ala His Ile Gln Val Arg Arg Gly Ile Pro Pro Arg Pro Arg
         35                  40                  45

Arg Arg Ala Gly Thr Pro Glu Lys Arg Tyr Arg Ala Pro Ile Phe Thr
     50                  55                  60

Val Ser Leu Lys His Ser Arg Arg Ser Trp Glu Arg Asn Arg Asp Glu
 65                  70                  75                  80

Leu Arg Arg Pro Ile Trp Arg Asp Phe Val Arg Cys Pro Thr Ser Ser
                 85                  90                  95

Arg Thr Glu Thr Lys Glu Leu Arg Asn Val Thr Pro Ala Gln Tyr Phe
            100                 105                 110

Glu Lys Ala Ala Thr Ala Phe Gly Gly Leu Gly Lys Cys Ile Thr Glu
        115                 120                 125

Glu Leu Arg Leu Glu Asn Gln Lys Cys Leu Leu Asp Met Val Asn Arg
    130                 135                 140

Ala Val Asp Asp Asp Cys Asp Asp Ile Asp Arg Asp Arg Gly Ile
145                 150                 155                 160

Cys Phe Pro Ala Phe Leu Ser Ser Gly Ser Ser Asp Leu Ala Ala Asp
                165                 170                 175

Ala Ala Phe Thr Ser Trp Lys Gln Phe Cys Gly Arg Ala Ala Ser Leu
            180                 185                 190

Lys Gly Arg Trp Thr Ser Arg Pro Asp Ile Ala Arg Leu Ala Lys Ile
        195                 200                 205

Ser Arg Ala Val Tyr Leu Ala Asn Cys Ser Phe Glu Glu Leu Leu Phe
    210                 215                 220

Ala Cys Asp Glu Thr Leu Val Trp Met Leu Trp His Gln Phe Glu Asp
225                 230                 235                 240

Glu Arg Ile Tyr Pro His Asp Pro Ile Phe Ser Asn Ile Tyr Cys Ala
                245                 250                 255

Cys Gln Ser Leu Ala Met His Leu Gly Pro Ile Leu Pro Cys Tyr Leu
            260                 265                 270

Ser Ser Ile Gly Ser Gln Leu Arg Asp Thr Thr Arg Ser Gln Glu Leu
        275                 280                 285

Ser Leu Ser Ser Ala Lys Cys Pro Leu Thr Leu Leu Thr Phe Phe
    290                 295                 300

Asp Arg Phe Ser Arg Ile Val Tyr Pro Arg Ser Glu Ala Ile Val Met
305                 310                 315                 320

Asn His Lys Ala Ile Asp Pro Ala Arg Thr Leu Trp Asp Met Tyr Tyr
                325                 330                 335

Pro Gly Thr Cys Ser Lys Lys Ile Pro Leu Val Leu Arg Ser Thr Gln
            340                 345                 350

Met Cys Ala Ala Lys Arg Asn Ala Glu Trp Phe Val Arg Ser Ser Lys
        355                 360                 365
```

```
Pro Gln Tyr Thr Val Gly Lys Phe Ser Leu Ala Thr Cys Leu Thr Val
    370                 375                 380

Leu Tyr Thr Tyr Arg His Met Ala Val Leu Tyr Trp Asn Trp Cys His
385                 390                 395                 400

Pro Thr Phe Leu Lys Ile Ala Ile Ser Val Thr Gly Gln Gln Met Ala
                405                 410                 415

Pro Arg Ala Gln
        420
```

<210> SEQ ID NO 13
<211> LENGTH: 21
<212> TYPE: DNA
<213> ORGANISM: Infectious Laryngotracheitis Virus

<400> SEQUENCE: 13
tgccggagcg caaccgcatg g                                         21

<210> SEQ ID NO 14
<211> LENGTH: 59
<212> TYPE: DNA
<213> ORGANISM: Infectious Laryngotracheitis Virus

<400> SEQUENCE: 14
gacaccgaat tcgtaagctt tccccgggca gtcgacaacg tggagcattt ttatttatc    59

<210> SEQ ID NO 15
<211> LENGTH: 22
<212> TYPE: DNA
<213> ORGANISM: Infectious Laryngotracheitis Virus

<400> SEQUENCE: 15
gtgttatctc tctagcattg gc                                        22

<210> SEQ ID NO 16
<211> LENGTH: 32
<212> TYPE: DNA
<213> ORGANISM: Infectious Laryngotracheitis Virus

<400> SEQUENCE: 16
agttctgaat tcgtgtccgt tgtattgtat tc                             32

<210> SEQ ID NO 17
<211> LENGTH: 50
<212> TYPE: DNA
<213> ORGANISM: Infectious Laryngotracheitis Virus

<400> SEQUENCE: 17
cgaattcact agtgtgtgtc tgcaggcggc cgcgtgtgtg tcgacggtac            50

<210> SEQ ID NO 18
<211> LENGTH: 50
<212> TYPE: DNA
<213> ORGANISM: Infectious Laryngotracheitis Virus

<400> SEQUENCE: 18
cgtcgacaca cacgcggccg cctgcagaca cacactagtg aattcgagct            50

<210> SEQ ID NO 19
<211> LENGTH: 22
<212> TYPE: DNA
<213> ORGANISM: Newcastle Disease Virus HN

<400> SEQUENCE: 19

```
cagaccaagc ttcttaaatc cc                                              22

<210> SEQ ID NO 20
<211> LENGTH: 16
<212> TYPE: DNA
<213> ORGANISM: Newcastle Disease Virus HN

<400> SEQUENCE: 20
gtattcggga caatgc                                                     16

<210> SEQ ID NO 21
<211> LENGTH: 21
<212> TYPE: DNA
<213> ORGANISM: Newcastle Disease Virus HN

<400> SEQUENCE: 21
gtgacatcac tagcgtcatc c                                               21

<210> SEQ ID NO 22
<211> LENGTH: 36
<212> TYPE: DNA
<213> ORGANISM: Newcastle Disease Virus HN

<400> SEQUENCE: 22
ccgcatcatc agcggccgcg atcggtcatg gacagt                               36

<210> SEQ ID NO 23
<211> LENGTH: 18
<212> TYPE: DNA
<213> ORGANISM: Newcastle Disease Virus HN

<400> SEQUENCE: 23
tgaccctgtc tgggatga                                                   18

<210> SEQ ID NO 24
<211> LENGTH: 36
<212> TYPE: DNA
<213> ORGANISM: Newcastle Disease Virus HN

<400> SEQUENCE: 24
ggatcccggt cgacacattg cggccgcaag atgggc                               36

<210> SEQ ID NO 25
<211> LENGTH: 40
<212> TYPE: DNA
<213> ORGANISM: Newcastle Disease Virus HN

<400> SEQUENCE: 25
gactggtacc gcggccgcat gcactttta ggcggaattg                            40

<210> SEQ ID NO 26
<211> LENGTH: 18
<212> TYPE: DNA
<213> ORGANISM: Newcastle Disease Virus HN

<400> SEQUENCE: 26
ttcgggacat tttcgcgg                                                   18

<210> SEQ ID NO 27
<211> LENGTH: 18
<212> TYPE: DNA
<213> ORGANISM: Newcastle Disease Virus HN
```

-continued

```
<400> SEQUENCE: 27
tatatggcgt tagtctcc                                              18

<210> SEQ ID NO 28
<211> LENGTH: 41
<212> TYPE: DNA
<213> ORGANISM: Newcastle Disease Virus HN

<400> SEQUENCE: 28
ttgcgagctc gcggccgctt attacacagc atcatcttct g                    41
```